(12) United States Patent
Soto et al.

(10) Patent No.: US 11,426,390 B2
(45) Date of Patent: Aug. 30, 2022

(54) METHODS OF TREATING GASTROINTESTINAL STROMAL TUMORS

(71) Applicant: Deciphera Pharmaceuticals, LLC, Waltham, MA (US)

(72) Inventors: Rodrigo Ruiz Soto, Waltham, MA (US); Oliver Rosen, Waltham, MA (US); Jama Pitman, Waltham, MA (US)

(73) Assignee: Deciphera Pharmaceuticals, LLC, Waltham, MA (US)

( * ) Notice: Subject to any disclaimer, the term of this patent is extended or adjusted under 35 U.S.C. 154(b) by 0 days.

(21) Appl. No.: 17/583,977

(22) Filed: Jan. 25, 2022

(65) Prior Publication Data

US 2022/0142997 A1  May 12, 2022

Related U.S. Application Data

(60) Continuation of application No. 17/180,218, filed on Feb. 19, 2021, now Pat. No. 11,266,635, which is a division of application No. 17/028,640, filed on Sep. 22, 2020, now Pat. No. 10,966,966, which is a continuation of application No. PCT/US2020/045876, filed on Aug. 12, 2020.

(60) Provisional application No. 63/023,921, filed on May 13, 2020, provisional application No. 63/023,936, filed on May 13, 2020, provisional application No. 62/968,927, filed on Jan. 31, 2020, provisional application No. 62/968,945, filed on Jan. 31, 2020, provisional application No. 62/936,018, filed on Nov. 15, 2019, provisional application No. 62/926,981, filed on Oct. 25, 2019, provisional application No. 62/904,198, filed on Sep. 23, 2019, provisional application No. 62/885,797, filed on Aug. 12, 2019.

(51) Int. Cl.
| | |
|---|---|
| *A61K 31/4375* | (2006.01) |
| *A61K 31/4745* | (2006.01) |
| *A61P 9/12* | (2006.01) |
| *A61P 35/00* | (2006.01) |

(52) U.S. Cl.
CPC ...... *A61K 31/4375* (2013.01); *A61K 31/4745* (2013.01); *A61P 9/12* (2018.01); *A61P 35/00* (2018.01)

(58) Field of Classification Search
CPC ............................ A61K 31/4375; A61P 35/00
See application file for complete search history.

(56) References Cited

U.S. PATENT DOCUMENTS

| | | |
|---|---|---|
| 3,528,980 A | 9/1970 | Islip |
| 3,818,024 A | 6/1974 | Krenzer |
| 3,939,122 A | 2/1976 | Merten et al. |
| 3,949,002 A | 4/1976 | Feasey et al. |
| 4,093,624 A | 6/1978 | Revankar et al. |
| 4,296,237 A | 10/1981 | Cragoe, Jr. et al. |
| 4,366,189 A | 12/1982 | Burdeska et al. |
| 4,432,992 A | 2/1984 | Cragoe, Jr. et al. |
| 4,525,450 A | 6/1985 | Itoh et al. |
| 4,816,454 A | 3/1989 | Zoller et al. |
| 5,103,014 A | 4/1992 | Musser et al. |
| 5,162,360 A | 11/1992 | Creswell et al. |
| 5,189,045 A | 2/1993 | Peglion et al. |
| 5,319,099 A | 6/1994 | Kamata et al. |
| 5,494,925 A | 2/1996 | Court et al. |
| 5,514,691 A | 5/1996 | Chan et al. |
| 5,614,532 A | 3/1997 | Carling et al. |
| 5,621,010 A | 4/1997 | Sueda et al. |
| 5,658,924 A | 8/1997 | Matsuura et al. |
| 5,721,231 A | 2/1998 | Moriwaki et al. |
| 5,811,456 A | 9/1998 | Seman et al. |
| 6,020,357 A | 2/2000 | Pinto et al. |
| 6,028,085 A | 2/2000 | Bromidge |
| 6,080,763 A | 6/2000 | Regan et al. |
| 6,123,964 A | 9/2000 | Asgharnejad et al. |
| 6,147,088 A | 11/2000 | Goulet et al. |
| 6,197,599 B1 | 3/2001 | Chin et al. |
| 6,235,786 B1 | 5/2001 | Dai et al. |
| 6,294,573 B1 | 9/2001 | Curtin et al. |
| 6,319,921 B1 | 11/2001 | Cirillo et al. |
| 6,410,254 B1 | 6/2002 | Finer et al. |
| 6,500,628 B1 | 12/2002 | Robison |
| 6,525,046 B1 | 2/2003 | Cirillo et al. |
| 6,645,990 B2 | 11/2003 | Askew et al. |
| 6,763,607 B2 | 7/2004 | Beyerinck et al. |
| 6,916,924 B2 | 7/2005 | Tan et al. |
| 6,973,741 B2 | 12/2005 | Beyerinck et al. |
| 7,071,199 B1 | 7/2006 | Hirst et al. |
| 7,135,550 B2 | 11/2006 | Come et al. |

(Continued)

FOREIGN PATENT DOCUMENTS

| | | |
|---|---|---|
| CN | 101528744 A | 9/2009 |
| CN | 101553232 A | 10/2009 |

(Continued)

OTHER PUBLICATIONS

U.S. Appl. No. 11/963,740, filed Dec. 21, 2007, Patented, U.S. Pat. No. 8,163,756.

(Continued)

*Primary Examiner* — Erich A Leeser
(74) *Attorney, Agent, or Firm* — Goodwin Procter LLP

(57) ABSTRACT

The present disclosure relates to methods of treating gastrointestinal stromal tumors to a subject in need thereof, comprising administering to the subject a therapeutically effective amount of ripretinib or a pharmaceutically acceptable salt thereof.

6 Claims, 37 Drawing Sheets

(56) References Cited

U.S. PATENT DOCUMENTS

| | | |
|---|---|---|
| 7,144,911 B2 | 12/2006 | Flynn et al. |
| 7,202,257 B2 | 4/2007 | Flynn et al. |
| 7,211,575 B2 | 5/2007 | Moss et al. |
| 7,279,576 B2 | 10/2007 | Flynn et al. |
| 7,342,037 B2 | 3/2008 | Flynn et al. |
| 7,531,566 B2 | 5/2009 | Flynn et al. |
| 7,666,895 B2 | 2/2010 | Flynn et al. |
| 7,737,283 B2 | 6/2010 | Flynn et al. |
| 7,790,756 B2 | 9/2010 | Flynn et al. |
| 7,897,762 B2 | 3/2011 | Flynn et al. |
| 8,143,293 B2 | 3/2012 | Flynn et al. |
| 8,163,756 B2 | 4/2012 | Flynn et al. |
| 8,188,113 B2 | 5/2012 | Flynn et al. |
| 8,278,331 B2 | 10/2012 | Flynn et al. |
| 8,343,550 B2 | 1/2013 | Beyerinck et al. |
| 8,461,179 B1 | 6/2013 | Flynn et al. |
| 8,486,951 B2 | 7/2013 | Flynn et al. |
| 8,569,319 B2 | 10/2013 | Flynn et al. |
| 8,586,565 B2 | 11/2013 | Flynn et al. |
| 8,637,672 B2 | 1/2014 | Flynn et al. |
| 8,669,289 B2 | 3/2014 | Li |
| 8,741,911 B2 | 6/2014 | Allgeier et al. |
| 8,828,443 B2 | 9/2014 | Beyerinck et al. |
| 8,921,565 B2 | 12/2014 | Flynn et al. |
| 8,940,756 B2 | 1/2015 | Flynn et al. |
| 9,012,635 B2 | 4/2015 | Flynn et al. |
| 9,133,183 B2 | 9/2015 | Flynn et al. |
| 9,181,223 B2 | 11/2015 | Kaufman et al. |
| 9,187,474 B2 | 11/2015 | Flynn et al. |
| 9,193,719 B2 | 11/2015 | Flynn et al. |
| 9,248,584 B2 | 2/2016 | Friesen et al. |
| 9,265,731 B2 | 2/2016 | Ray et al. |
| 9,309,224 B2 | 4/2016 | Flynn et al. |
| 9,334,267 B2 | 5/2016 | Flynn et al. |
| 9,339,467 B2 | 5/2016 | Beyerinck et al. |
| 9,382,228 B2 | 7/2016 | Flynn et al. |
| 9,387,202 B2 | 7/2016 | Flynn et al. |
| 9,457,019 B2 | 10/2016 | Flynn et al. |
| 9,724,664 B2 | 8/2017 | Friesen et al. |
| 10,300,443 B2 | 5/2019 | Friesen et al. |
| 10,383,941 B2 | 8/2019 | Beyerinck et al. |
| 10,675,602 B2 | 6/2020 | Friesen et al. |
| 10,966,966 B2 | 4/2021 | Soto et al. |
| 11,185,535 B2 | 11/2021 | Kaufman et al. |
| 2002/0058678 A1 | 5/2002 | Cirillo et al. |
| 2002/0077486 A1 | 6/2002 | Scarborough et al. |
| 2002/0165394 A1 | 11/2002 | Dumas et al. |
| 2002/0193405 A1 | 12/2002 | Askew et al. |
| 2003/0060455 A1 | 3/2003 | Moss et al. |
| 2003/0105139 A1 | 6/2003 | Gaster et al. |
| 2003/0144278 A1 | 7/2003 | Riedl et al. |
| 2003/0181442 A1 | 9/2003 | Riedl et al. |
| 2003/0207870 A1 | 11/2003 | Dumas et al. |
| 2003/0216396 A1 | 11/2003 | Dumas et al. |
| 2003/0232865 A1 | 12/2003 | Cirillo et al. |
| 2004/0043388 A1 | 3/2004 | Come et al. |
| 2004/0067938 A1 | 4/2004 | Zhang et al. |
| 2004/0102636 A1 | 5/2004 | Miller et al. |
| 2004/0157827 A1 | 8/2004 | Pevarello et al. |
| 2004/0167224 A1 | 8/2004 | Ozaki et al. |
| 2004/0171075 A1 | 9/2004 | Flynn et al. |
| 2004/0180906 A1 | 9/2004 | Flynn et al. |
| 2004/0229937 A1 | 11/2004 | Dumas et al. |
| 2005/0014753 A1 | 1/2005 | Ding et al. |
| 2005/0148605 A1 | 7/2005 | Grotzfeld et al. |
| 2005/0165024 A1 | 7/2005 | Milanov et al. |
| 2005/0165031 A1 | 7/2005 | Grotzfeld et al. |
| 2005/0165074 A1 | 7/2005 | Grotzfeld et al. |
| 2005/0171171 A1 | 8/2005 | Mehta et al. |
| 2005/0171172 A1 | 8/2005 | Lai et al. |
| 2005/0192314 A1 | 9/2005 | Mehta et al. |
| 2005/0197371 A1 | 9/2005 | Milanov et al. |
| 2005/0256174 A1 | 11/2005 | Wood et al. |
| 2005/0261315 A1 | 11/2005 | Mehta et al. |
| 2005/0267182 A1 | 12/2005 | Milanov et al. |
| 2005/0288286 A1 | 12/2005 | Flynn et al. |
| 2006/0229337 A1 | 10/2006 | Brittelli et al. |
| 2006/0247186 A1 | 11/2006 | Carter et al. |
| 2007/0037794 A1 | 2/2007 | Ungashe et al. |
| 2007/0078121 A1 | 4/2007 | Flynn et al. |
| 2007/0155764 A1 | 7/2007 | Lang et al. |
| 2007/0179130 A1 | 8/2007 | Bannen |
| 2007/0191336 A1 | 8/2007 | Flynn et al. |
| 2007/0244120 A1 | 10/2007 | Dumas et al. |
| 2007/0293685 A1 | 12/2007 | Fritch et al. |
| 2008/0009527 A1 | 1/2008 | Dumas et al. |
| 2008/0045531 A1 | 2/2008 | Flynn et al. |
| 2008/0045706 A1 | 2/2008 | Flynn et al. |
| 2008/0064717 A1 | 3/2008 | Iyengar et al. |
| 2008/0090856 A1 | 4/2008 | Flynn et al. |
| 2008/0113967 A1 | 5/2008 | Flynn et al. |
| 2008/0114006 A1 | 5/2008 | Flynn et al. |
| 2008/0132506 A1 | 6/2008 | Flynn et al. |
| 2008/0176846 A1 | 7/2008 | Chianelli et al. |
| 2008/0187978 A1 | 8/2008 | Flynn et al. |
| 2008/0194836 A1 | 8/2008 | Gharbaoui et al. |
| 2008/0200530 A1 | 8/2008 | Unett et al. |
| 2008/0207699 A1 | 8/2008 | Hoelzemann et al. |
| 2008/0214545 A1 | 9/2008 | Lee et al. |
| 2008/0220497 A1 | 9/2008 | Flynn et al. |
| 2008/0221192 A1 | 9/2008 | Wan et al. |
| 2008/0248487 A1 | 10/2008 | Flynn et al. |
| 2008/0248548 A1 | 10/2008 | Flynn et al. |
| 2008/0300281 A1 | 12/2008 | Dumas et al. |
| 2009/0069310 A1 | 3/2009 | Flynn et al. |
| 2009/0075986 A1 | 3/2009 | Flynn et al. |
| 2009/0093526 A1 | 4/2009 | Miller et al. |
| 2009/0099190 A1 | 4/2009 | Flynn et al. |
| 2009/0105230 A1 | 4/2009 | Flynn et al. |
| 2009/0124633 A1 | 5/2009 | Jonczyk et al. |
| 2009/0137021 A1 | 5/2009 | Flynn et al. |
| 2009/0192307 A1 | 7/2009 | Michelotti et al. |
| 2009/0215799 A1 | 8/2009 | Stieber et al. |
| 2009/0281089 A1 | 11/2009 | Gunzner et al. |
| 2009/0312349 A1 | 12/2009 | Flynn et al. |
| 2009/0325945 A1 | 12/2009 | Niculescu-Duvaz et al. |
| 2010/0075971 A1 | 3/2010 | Dumas et al. |
| 2010/0160292 A1 | 6/2010 | Whitney et al. |
| 2010/0209420 A1 | 8/2010 | Lamb et al. |
| 2010/0286215 A1 | 11/2010 | Pelcman et al. |
| 2010/0298290 A1 | 11/2010 | Anand et al. |
| 2011/0077240 A1 | 3/2011 | Mannion et al. |
| 2011/0092461 A1 | 4/2011 | Gunzner et al. |
| 2011/0098293 A1 | 4/2011 | Mannion et al. |
| 2011/0112193 A1 | 5/2011 | Nilsson et al. |
| 2011/0124640 A1 | 5/2011 | Liu et al. |
| 2011/0136760 A1 | 6/2011 | Flynn et al. |
| 2011/0136809 A1 | 6/2011 | Lee et al. |
| 2011/0183997 A1 | 7/2011 | Chianelli et al. |
| 2011/0195110 A1 | 8/2011 | Smith et al. |
| 2012/0094980 A1 | 4/2012 | Gunzner et al. |
| 2012/0114605 A1 | 5/2012 | Li |
| 2012/0214808 A1 | 8/2012 | Bloxham et al. |
| 2012/0225057 A1 | 9/2012 | Flynn et al. |
| 2012/0270878 A1 | 10/2012 | Miller et al. |
| 2012/0289540 A1 | 11/2012 | Flynn et al. |
| 2013/0071403 A1 | 3/2013 | Rolland et al. |
| 2013/0225581 A1 | 8/2013 | Furuta et al. |
| 2013/0296326 A1 | 11/2013 | Pollock |
| 2014/0088075 A1 | 3/2014 | Flynn et al. |
| 2014/0107100 A1 | 4/2014 | Rice et al. |
| 2014/0147415 A1 | 5/2014 | Moussy et al. |
| 2014/0179632 A1 | 6/2014 | Mannion et al. |
| 2014/0296248 A1 | 10/2014 | Bernards et al. |
| 2014/0296267 A1 | 10/2014 | Fry et al. |
| 2014/0336210 A1 | 11/2014 | Christopher et al. |
| 2015/0031648 A1 | 1/2015 | Le Tiran et al. |
| 2015/0073141 A1 | 3/2015 | Teegarden et al. |
| 2015/0105550 A1 | 4/2015 | Gunzner et al. |
| 2015/0111879 A1 | 4/2015 | Gunzner et al. |
| 2015/0133462 A1 | 5/2015 | Singh et al. |
| 2015/0218652 A1 | 8/2015 | Doebele et al. |
| 2015/0225369 A1 | 8/2015 | Wucherer-Plietker et al. |
| 2015/0246033 A1 | 9/2015 | Flynn et al. |

(56) References Cited

U.S. PATENT DOCUMENTS

| | | | |
|---|---|---|---|
| 2015/0275306 A1 | 10/2015 | Bernards et al. |
| 2015/0320759 A1 | 11/2015 | Flynn et al. |
| 2016/0009709 A1 | 1/2016 | Cheve et al. |
| 2016/0045532 A1 | 2/2016 | Roberts et al. |
| 2016/0152569 A1 | 6/2016 | Gunzner-Toste et al. |
| 2016/0166679 A1 | 6/2016 | Low et al. |
| 2016/0222012 A1 | 8/2016 | Ruan |
| 2016/0289663 A1 | 10/2016 | Kiyokawa et al. |
| 2016/0374990 A1 | 12/2016 | Teegarden et al. |
| 2017/0015627 A1 | 1/2017 | Gunzner-Toste et al. |
| 2017/0121321 A1 | 5/2017 | Crews et al. |
| 2017/0174750 A1 | 6/2017 | Lim et al. |
| 2017/0349880 A1 | 12/2017 | Doucey et al. |
| 2017/0360791 A1 | 12/2017 | Joshi-Hangal et al. |
| 2018/0000771 A1 | 1/2018 | Inoue et al. |
| 2018/0071302 A1 | 3/2018 | Abella et al. |
| 2018/0071303 A1 | 3/2018 | Abella et al. |
| 2019/0091217 A1 | 3/2019 | Flynn et al. |
| 2020/0129489 A1 | 4/2020 | Flynn et al. |
| 2020/0253973 A1 | 8/2020 | Flynn et al. |
| 2020/0352920 A1 | 11/2020 | Flynn et al. |
| 2020/0354346 A1 | 11/2020 | Flynn et al. |
| 2020/0354352 A1 | 11/2020 | Flynn et al. |
| 2021/0015801 A1 | 1/2021 | Flynn et al. |

FOREIGN PATENT DOCUMENTS

| | | | |
|---|---|---|---|
| CN | 102731385 A | 10/2012 |
| CN | 105461699 A | 4/2016 |
| CN | 106822128 A | 6/2017 |
| CN | 108379591 A | 8/2018 |
| DE | 1115350 B | 10/1961 |
| DE | 4343831 A1 | 6/1995 |
| EP | 0021228 A1 | 1/1981 |
| EP | 0025232 A1 | 3/1981 |
| EP | 0154190 A1 | 9/1985 |
| EP | 0661276 A1 | 7/1995 |
| EP | 0692483 A4 | 11/1995 |
| EP | 0739884 A2 | 10/1996 |
| EP | 0867435 A1 | 9/1998 |
| EP | 0927555 A1 | 7/1999 |
| EP | 928790-A 1 | 7/1999 |
| EP | 0956855 A1 | 11/1999 |
| EP | 1281399 A2 | 2/2003 |
| EP | 2858646 A1 | 4/2015 |
| FR | 2337554 A1 | 8/1977 |
| FR | 2396549 A2 | 2/1979 |
| GB | 971307 A | 9/1964 |
| GB | 1410279 A | 10/1975 |
| GB | 2220206 A | 1/1990 |
| JP | 59-177557 A | 8/1984 |
| JP | 9-221476 | 8/1997 |
| JP | 2000275886 A | 10/2000 |
| JP | 2001-2687 A | 1/2001 |
| JP | 59-15247 B2 | 5/2016 |
| KR | 20130065368 A | 6/2013 |
| WO | WO-1991/19708 A1 | 12/1991 |
| WO | WO-1992/08693 A1 | 5/1992 |
| WO | WO-1994/18176 A1 | 8/1994 |
| WO | WO-1994/21617 | 9/1994 |
| WO | WO-1994/24095 A1 | 10/1994 |
| WO | WO-1995/006044 A1 | 3/1995 |
| WO | WO-1995/15954 A1 | 6/1995 |
| WO | WO-1995/29902 A1 | 11/1995 |
| WO | WO-1995/34540 A1 | 12/1995 |
| WO | WO-1996/16046 A2 | 5/1996 |
| WO | WO-1996/19477 A1 | 6/1996 |
| WO | WO-1996/023783 A1 | 8/1996 |
| WO | WO-1997/34900 A1 | 9/1997 |
| WO | WO-1997/037989 A2 | 10/1997 |
| WO | WO-1997/40028 A1 | 10/1997 |
| WO | WO-1997/045400 A1 | 12/1997 |
| WO | WO-1998/22103 A1 | 5/1998 |
| WO | WO-1998/52558 A1 | 11/1998 |
| WO | WO-1999/15164 A1 | 4/1999 |
| WO | WO-1999/23091 A1 | 5/1999 |
| WO | WO-1999/23093 A1 | 5/1999 |
| WO | WO-1999/32106 | 7/1999 |
| WO | WO-1999/32110 A1 | 7/1999 |
| WO | WO-1999/32111 | 7/1999 |
| WO | WO-1999/32455 | 7/1999 |
| WO | WO-1999/37622 A1 | 7/1999 |
| WO | WO-1999/59959 A1 | 11/1999 |
| WO | WO-2000/06550 A1 | 2/2000 |
| WO | WO-2000/07980 A1 | 2/2000 |
| WO | WO-2000/18738 A1 | 4/2000 |
| WO | WO-2000/21927 A2 | 4/2000 |
| WO | WO-2000/41698 A1 | 7/2000 |
| WO | WO-2000/042012 A1 | 7/2000 |
| WO | WO-2000/43384 A1 | 7/2000 |
| WO | WO-2000/55139 A2 | 9/2000 |
| WO | WO-2000/59506 A1 | 10/2000 |
| WO | WO-2000/071515 A2 | 11/2000 |
| WO | WO-2001/12621 A1 | 2/2001 |
| WO | WO-2001/14372 A2 | 3/2001 |
| WO | WO-2001/74771 A1 | 10/2001 |
| WO | WO-2001/96298 A1 | 12/2001 |
| WO | WO-2002/00647 A1 | 1/2002 |
| WO | WO-2002/14291 A1 | 2/2002 |
| WO | WO-2002/14311 A2 | 2/2002 |
| WO | WO-2002/026712 A2 | 4/2002 |
| WO | WO-2002/28835 A1 | 4/2002 |
| WO | WO-2002/34727 A2 | 5/2002 |
| WO | WO-2002/060869 A2 | 8/2002 |
| WO | WO-2002/060876 A1 | 8/2002 |
| WO | WO-2002/062763 A2 | 8/2002 |
| WO | WO-2002/070662 A2 | 9/2002 |
| WO | WO-2003/005999 A2 | 1/2003 |
| WO | WO-2003/047579 A1 | 6/2003 |
| WO | WO-2003/053368 A2 | 7/2003 |
| WO | WO-2003/059373 A2 | 7/2003 |
| WO | WO-2003/068223 A1 | 8/2003 |
| WO | WO-2003/068229 A1 | 8/2003 |
| WO | WO-2003/072577 A1 | 9/2003 |
| WO | WO-2003/084539 A2 | 10/2003 |
| WO | WO-2004/004720 A1 | 1/2004 |
| WO | WO-2004/056783 A1 | 7/2004 |
| WO | WO-2004/060305 A2 | 7/2004 |
| WO | WO-2004/060306 A2 | 7/2004 |
| WO | WO-2004/061084 A2 | 7/2004 |
| WO | WO-2004/078128 A2 | 9/2004 |
| WO | WO-2004/078746 A2 | 9/2004 |
| WO | WO-2004/113352 A1 | 12/2004 |
| WO | WO-2005/002673 A1 | 1/2005 |
| WO | WO-2005/012254 A1 | 2/2005 |
| WO | WO-2005/024755 A2 | 3/2005 |
| WO | WO-2005/034869 A2 | 4/2005 |
| WO | WO-2005/048948 A2 | 6/2005 |
| WO | WO-2005/103011 A1 | 11/2005 |
| WO | WO-2005/110994 A2 | 11/2005 |
| WO | WO-2006/014290 A2 | 2/2006 |
| WO | WO-2006/014325 A2 | 2/2006 |
| WO | WO-2006/018662 A2 | 2/2006 |
| WO | WO-2006/028958 A2 | 3/2006 |
| WO | WO-2006/039718 A2 | 4/2006 |
| WO | WO-2006/040056 A1 | 4/2006 |
| WO | WO-2006/046552 A1 | 5/2006 |
| WO | WO-2006/052936 A2 | 5/2006 |
| WO | WO-2006/062984 A2 | 6/2006 |
| WO | WO-2006/071940 A2 | 7/2006 |
| WO | WO-2006/072589 A2 | 7/2006 |
| WO | WO-2006/078610 A1 | 7/2006 |
| WO | WO-2006/081034 A2 | 8/2006 |
| WO | WO-2006/081335 A2 | 8/2006 |
| WO | WO-2006/099075 A2 | 9/2006 |
| WO | WO-2006/105844 A1 | 10/2006 |
| WO | WO-2007/008917 A2 | 1/2007 |
| WO | WO-2007/042321 A2 | 4/2007 |
| WO | WO-2007/064872 A2 | 6/2007 |
| WO | WO-2007/076473 A2 | 7/2007 |
| WO | WO-2007/081690 A2 | 7/2007 |
| WO | WO-2007/115670 A1 | 10/2007 |
| WO | WO-2007/125330 A1 | 11/2007 |
| WO | WO-2007/136465 A2 | 11/2007 |

(56) References Cited

FOREIGN PATENT DOCUMENTS

| | | |
|---|---|---|
| WO | WO-2007/137107 A2 | 11/2007 |
| WO | WO-2008/033858 A2 | 3/2008 |
| WO | WO-2008/033999 A2 | 3/2008 |
| WO | WO-2008/034008 A2 | 3/2008 |
| WO | WO-2008/046003 A2 | 4/2008 |
| WO | WO-2008/051757 A1 | 5/2008 |
| WO | WO-2008/131227 A1 | 10/2008 |
| WO | WO-2008/131253 A1 | 10/2008 |
| WO | WO-2008/140895 A1 | 11/2008 |
| WO | WO-2009/030887 A2 | 3/2009 |
| WO | WO-2009/076454 A2 | 6/2009 |
| WO | WO-2009/109035 A1 | 9/2009 |
| WO | WO-2009/126863 A2 | 10/2009 |
| WO | WO-2009/127822 A2 | 10/2009 |
| WO | WO-2009/138758 A2 | 11/2009 |
| WO | WO-2010/011837 A1 | 1/2010 |
| WO | WO-2010/051373 A1 | 5/2010 |
| WO | WO-2010/124283 A2 | 10/2010 |
| WO | WO-2010/135524 A1 | 11/2010 |
| WO | WO-2011/067306 A1 | 6/2011 |
| WO | WO-2011/123788 A1 | 10/2011 |
| WO | WO-2011/137342 A1 | 11/2011 |
| WO | WO-2011/139891 A1 | 11/2011 |
| WO | WO-2011/150198 A1 | 12/2011 |
| WO | WO-2012/008563 A1 | 1/2012 |
| WO | WO-2012/019015 A2 | 2/2012 |
| WO | WO-2012/035131 A1 | 3/2012 |
| WO | WO-2012/071519 A1 | 5/2012 |
| WO | WO-2012/097021 A1 | 7/2012 |
| WO | WO-2012/138783 A2 | 10/2012 |
| WO | WO-2013/036232 A2 | 3/2013 |
| WO | WO-2013/043569 A1 | 3/2013 |
| WO | WO-2013/066440 A1 | 5/2013 |
| WO | WO-2013/078295 A2 | 5/2013 |
| WO | WO-2013/134243 A1 | 9/2013 |
| WO | WO-2013/134252 A1 | 9/2013 |
| WO | WO-2013/134298 A1 | 9/2013 |
| WO | WO-2013/177420 A2 | 11/2013 |
| WO | WO-2013/184119 A1 | 12/2013 |
| WO | WO-2014/015056 A2 | 1/2014 |
| WO | WO-2014/032755 A2 | 3/2014 |
| WO | WO-2014/036387 A2 | 3/2014 |
| WO | WO-2014/037480 A1 | 3/2014 |
| WO | WO-2014/040242 A1 | 3/2014 |
| WO | WO-2014/040549 A1 | 3/2014 |
| WO | WO-2014/058317 A1 | 4/2014 |
| WO | WO-2014/102376 A1 | 7/2014 |
| WO | WO-2014/102377 A1 | 7/2014 |
| WO | WO-2014/139458 A1 | 9/2014 |
| WO | WO-2014/145004 A1 | 9/2014 |
| WO | WO-2014/145015 A2 | 9/2014 |
| WO | WO-2014/145023 A1 | 9/2014 |
| WO | WO-2014/145025 A2 | 9/2014 |
| WO | WO-2014/145028 A2 | 9/2014 |
| WO | WO-2014/145029 A2 | 9/2014 |
| WO | WO-2014/160183 A1 | 10/2014 |
| WO | WO-2014/182643 A2 | 11/2014 |
| WO | WO-2015/011399 A1 | 1/2015 |
| WO | WO-2015/069217 A1 | 5/2015 |
| WO | WO-2015/069266 A1 | 5/2015 |
| WO | WO-2015/076213 A1 | 5/2015 |
| WO | WO-2015/092423 A1 | 6/2015 |
| WO | WO-2015/106292 A1 | 7/2015 |
| WO | WO-2015/106294 A1 | 7/2015 |
| WO | WO-2015/148620 A2 | 10/2015 |
| WO | WO-2015/184443 A1 | 12/2015 |
| WO | WO-2016/061228 A1 | 4/2016 |
| WO | WO-2016/061231 A1 | 4/2016 |
| WO | WO-2016/096903 A1 | 6/2016 |
| WO | WO-2016/103223 A1 | 6/2016 |
| WO | WO-2016/114322 A1 | 7/2016 |
| WO | WO-2016/135046 A1 | 9/2016 |
| WO | WO-2016/154524 A1 | 9/2016 |
| WO | WO-2016/196141 A1 | 12/2016 |
| WO | WO-2017/013160 A1 | 1/2017 |
| WO | WO-2017/042944 A1 | 3/2017 |
| WO | WO-2017/079267 A1 | 5/2017 |
| WO | WO-2017/117182 A1 | 7/2017 |
| WO | WO-2017/146794 A1 | 8/2017 |
| WO | WO-2017/146795 A1 | 8/2017 |
| WO | WO-2017/214514 A1 | 12/2017 |
| WO | WO-2018/005737 A1 | 1/2018 |
| WO | WO-2018/052053 A1 | 3/2018 |
| WO | WO-2018/053189 A2 | 3/2018 |
| WO | WO-2018/106595 A1 | 6/2018 |
| WO | WO-2018/195450 A1 | 10/2018 |
| WO | WO-2018/222173 A1 | 12/2018 |
| WO | WO-2018/222644 A1 | 12/2018 |
| WO | WO 2020/185812 * 9/2020 | ........... C07D 471/04 |
| WO | WO-2020/185812 A1 | 9/2020 |

OTHER PUBLICATIONS

U.S. Appl. No. 11/870,388, filed Oct. 10, 2007, Patented, U.S. Pat. No. 7,790,756.
U.S. Appl. No. 12/829,561, filed Jul. 2, 2010, Patented, U.S. Pat. No. 8,586,565.
U.S. Appl. No. 11/854,354, filed Sep. 12, 2007, Patented, U.S. Pat. No. 8,188,113.
U.S. Appl. No. 10/746,460, filed Dec. 24, 2003, Patented, U.S. Pat. No. 7,144,911.
U.S. Appl. No. 10/886,329, filed Jul. 6, 2004, Patented, U.S. Pat. No. 7,202,257.
U.S. Appl. No. 11/450,840, filed Jun. 9, 2006, Patented, U.S. Pat. No. 7,342,037.
U.S. Appl. No. 11/336,708, filed Jan. 20, 2006, Patented, U.S. Pat. No. 7,531,566.
U.S. Appl. No. 11/450,850, filed Jun. 9, 2006, Patented, U.S. Pat. No. 7,666,895.
U.S. Appl. No. 10/746,607, filed Dec. 24, 2003, Patented, U.S. Pat. No. 7,279,576.
U.S. Appl. No. 11/854,293, filed Sep. 12, 2007, Patented, U.S. Pat. No. 7,897,762.
U.S. Appl. No. 12/105,408, filed Apr. 18, 2008, Patented, U.S. Pat. No. 8,143,293.
U.S. Appl. No. 13/590,955, filed Aug. 21, 2012, Patented, U.S. Pat. No. 8,486,951.
U.S. Appl. No. 11/450,849, filed Jun. 9, 2006, Patented, U.S. Pat. No. 7,737,283.
U.S. Appl. No. 13/785,575, filed Mar. 5, 2013, Patented, U.S. Pat. No. 8,741,911.
U.S. Appl. No. 12/608,578, filed Oct. 29, 2009, Patented, U.S. Pat. No. 8,278,331.
U.S. Appl. No. 13/098,247, filed Apr. 29, 2011, Patented, U.S. Pat. No. 8,569,319.
U.S. Appl. No. 13/559,170, filed Jul. 26, 2012, Patented, U.S. Pat. No. 8,637,672.
U.S. Appl. No. 14/214,134, filed Mar. 14, 2014, Patented, U.S. Pat. No. 9,133,183.
U.S. Appl. No. 14/383,803, filed Mar. 5, 2013, Patented, U.S. Pat. No. 9,187,474.
U.S. Appl. No. 13/491,394, filed Jun. 7, 2012, Patented, U.S. Pat. No. 8,461,179.
U.S. Appl. No. 13/801,753, filed Mar. 13, 2013, Patented, U.S. Pat. No. 8,940,756.
U.S. Appl. No. 16/387,315, filed Apr. 17, 2019, Pending.
U.S. Appl. No. 14/214,127, filed Mar. 14, 2014, Patented, U.S. Pat. No. 9,012,635.
U.S. Appl. No. 13/683,277, filed Nov. 21, 2012, Patented, U.S. Pat. No. 8,921,565.
U.S. Appl. No. 14/549,125, filed Nov. 20, 2014, Patented, U.S. Pat. No. 9,387,202.
U.S. Appl. No. 14/214,160, filed Mar. 14, 2014, Patented, U.S. Pat. No. 9,193,719.
U.S. Appl. No. 14/214,717, filed Mar. 14, 2014, Patented, U.S. Pat. No. 9,181,223.
U.S. Appl. No. 14/214,185, filed Mar. 14, 2014, Patented, U.S. Pat. No. 9,382,228.

(56) References Cited

OTHER PUBLICATIONS

U.S. Appl. No. 14/214,179, filed Mar. 14, 2014, Patented, U.S. Pat. No. 9,309,224.
U.S. Appl. No. 14/383,799, filed Mar. 5, 2013, Patented, U.S. Pat. No. 9,334,267.
U.S. Appl. No. 14/535,900, filed Nov. 7, 2014, Patented, U.S. Pat. No. 9,457,019.
U.S. Appl. No. 15/957,888, filed Apr. 19, 2018, Pending, U.S. 2019-0091217 A1.
U.S. Appl. No. 16/617,721, filed Nov. 27, 2019, Pending, U.S. 2020-0129489 A1.
U.S. Appl. No. 17/028,591, filed Sep. 22, 2020, Pending, U.S. 2021-0015801 A1.
U.S. Appl. No. 16/943,821, filed Jul. 30, 2020, Pending.
U.S. Appl. No. 16/943,871, filed Jul. 30, 2020, Pending, U.S. 2020-0352920 A1.
U.S. Appl. No. 16/725,282, filed Dec. 23, 2019, Pending, U.S. 2020-0253973 A1.
U.S. Appl. No. 16/870,384, filed May. 8, 2020, Pending, U.S. 2020-0354352 A1.
U.S. Appl. No. 16/870,418, filed May 8, 2020, Pending, U.S. 2020-0354346 A1.
U.S. Appl. No. 16/902,989, filed Jun. 16, 2020, Pending.
U.S. Appl. No. 16/991,644, filed Aug. 12, 2020, Pending.
U.S. Appl. No. 17/028,640, filed Sep. 22, 2020, Pending, U.S. Pat. No. 10,966,966.
U.S. Appl. No. 17/180,234, filed Feb. 19, 2021, Patented, U.S. Pat. No. 11,185,535.
U.S. Appl. No. 17/180,241, filed Feb. 19, 2021, Pending.
U.S. Appl. No. 17/504,133, filed Oct. 18, 2021, Pending.
U.S. Appl. No. 17/583,985, filed Jan. 25, 2022, Pending.
"A Safety, Tolerability and PK Study of DCC-2618 in Patients With Advanced Malignancies," ClinicalTrials.gov, Jan. 12, 2018, pp. 1-11. Retrieved from the Internet: URL: <https://clinicaltrials.gov/ct2/show/NC>.
"Additions and Corrections", Journal of Medicinal Chemistry, 32(12):2583 (1989).
"NHLBI LBC Computational Biophysics Scetion", CHARMM Documentation Index, http://www.lobos.nih.gov/Charmm/chmdoc.html, printed Mar. 4, 2005.
"Trilateral Project WM4—Comparative Studies in New Technologies: Report on Comparative Study on Protein 3-Dimensional Structure Related Claims—ANNEX 3: Comments of the USPTO", Vienna, Austria, Nov. 4-8, pp. 58-79 (2002).
Aklilu, et al., "Increased PTHRP Production by a Tyrosine Kinase Oncogene, Tpr-Met: Rose of the Ras Signaling Pathway", The American Physiological Society, pp. E277-E283 (1996).
Albericio, et al., "Synthesis of a Sulfaydantion Library", J. Comb. Chem., 3:290-300 (2001).
Almerico, et al., "On the Preparation of 1-aryl-2-heteroaryl- and 2-aryl-1-heteroaryl-pyrroles as Useful Building Blocks for Biologically Interesting Heterocycles", Arkivoc, Rudy Abramovitch Issue, pp. 129-142 (2001).
Antonescu, et al., "Acquired Resistance to Imatinib in Gastrointestinal Stromal Tumor Occurs Through Secondary Gene Mutation," Clinical cancer research : an official journal of the American Association for Cancer Research, 11(11):4182-4190 (2005).
Anzai, et al., "Alkyl- and Arylthiation of Uracil and Indole", J. Heterocyclic Chem., 16:567-569 (1979).
Askew, et al., "Molecular Recognition with Convergent Functional Groups: 6. Synthetic and Structural Studies with a Model Receptor for Nucleic Acid Components", J. Am. Chem., 111:1082-1090 (1989).
Avruch, J. et al., "Ras Activation of the Raf Kinase: Tyrosine Kinase Recmitment of the MAP Kinase Cascade," Recent Prag Harm. Res. (2001) 56: 127-155.
Bai et al., "Targeting the KITactivating switch control pocket: a novel mechanism to inhibit neoplastic mast cell proliferation and mast cell activation," Leukemia (2013), vol. 27, pp. 278-285.

Bais, et al., "Inhibition of Endogenous Wxalate Production: Biochemical Consideration of the Roles of Glycollate Oxidase and Lactate Dehydrogenase", Clinical Science, 76:303-309 (1989).
Baker, et al., "Irreversible Enzyme Inhibitors. 188. Inhibition of Mammalian Thymidine Phosphorylase", Journal of Medicinal Chemistry, 14:612-616 (1971).
Barker, et al., "Characterization of pp60c-src Tyrosine Kinase Activities Using a Continuous Assay: Autoactivation of the Enzyme is an Intermolecular Autophosphorylation Process", Biochemist , 35:14843-14851 (1995).
Barvian, et al, "Pyrido[2,3-d]pyrimidin-7-one Inhibitors of Cyclin-Dependent Kinases," J Med Chem. (2000) 43: 4606-4616.
Bausch, et al., "Proton-Transfer Chemistry of Urazoles and Related Imides, and Diacyl H drazides", J. Org. Chem., 56:5643-5651 (1991).
Beghini, et al., "C-kit mutations in core binding factor leukemias," Blood Journal, 95(2):726-727 (2000).
Benvenuti, et al., "Crystallization of Soluble Proteins in Vapor Diffusion for X-Ray Crystallography", Nature Protocols, 2(7):1633-1651 (2007).
Blay, et al., "Ripretinib in patients with advanced gastrointestinal stromal tumours (INVICTUS): a double-blind, randomised, placebo-controlled, phase 3 trial", Lancet Oncology, 21:923-934 (2020).
Bolton, et al, "Chapter 17. Ras Oncogene Directed Approaches in Cancer Chemotherapy," Ann. Rep. Med. Chem. (1994) 29: 165-174.
Bosca, et al., "Circular Dichroism Analysis of Ligand-Induced Conformational Changes in Protein Kinase C", Biochem. J., 290:827-832 (1993).
Boschelli, et al., "4-Anilino-3-quinolinecarbonitriles: An Emerging Class of Kinase Inhibitors", Current Topics in Medicinal Chemist, 2:1051-1063 (2002).
Bourdon NEC, et al., "Synthesis and Pharmacological Evaluation of New Pyrazolidine-3,5-diones as AT 1 Angiotensin II Receptor Antagonists", J. Med. Chem., 43:2685-2697 (2000).
Boyer, "Small Molecule Inhibitors of KDR (VEGFR-2) Kinase: An Overview of Structure Activit Relationships", Current Topics in Medicinal Chemist , 2:973-1000 (2002).
Brady, et al., "Fast Prediction and Visualization of Protein Binding Pockets with PASS". Journal of Computer-Aided Molecular Desi n, 14:383-401 (2000).
Branford, et al., "High Frequency of Point Mutations Clustered Within the Adenosine Triphosphate-binding Region of BCR/ABL in Patients With Chronic Myeloid Leukemia or Ph-positive Acute Lymphoblastic Leukemia Who Develop Imatinib (ST1571)resistance," Blood (2002) vol. 99, pp. 3472-3475.
Brasher, et al., "C-Abul has High Intrinsic Tyrosine Kinase Activity that is Stimulated by Mutation of the Src Homology 3 Domain and by Autophosphorylation at Two Distinct Re ulator T rosines", Journal of Biolo ical Chemistr , 275:35631-35637 (2000).
Bullock, et al., "Prospects for Kinase Activity Modulators in the Treatment of Diabetes and Diabetic Complications", Current Topics in Medicinal Chemistr , 2:915-938 (2002).
Byron, et al., "The Synthesis of some Substituted Biphenyl-4-carboxylic Acids, 4-Biphenylylacetic Acids, and 4-Aminobiphenyls", J. Chem. Soc. (C), Organic, pp. 840-845 (1966).
Cardillo, et al., "Su lie 1,2-difenil-3.5-dichetopirazolidine", Gazz. Chim., Ital., 9:973-985 (1966).
Carr, J. B., et al., "Isoxazolc Anthelmintics," J /'vied. Chem (1977) vol. 20, No. 7, pp. 934-939.
Chan et al., "Copper promoted C-N and C-O bond cross-coupling with phenyl and pyridylboronates," Tetrahedron Letters (2003) vol. 44, pp. 3863-3865.
Chan, "Promotion of Reaction of N-H Bonds with Triarylbismuth and Cupric Acetate," Tetrahedron Letters (1996) vol. 37, No. 50, pp. 9013-9016.
Chan, et al, "New N- and O-Arylations with Phenylboronic Acids and Cupric Acetate," Tetrahedron Lett. (1998) 39: 2933-2936.
Chen, et al., "Biochemical Evidence for the Autophosphorylation and Transphosphorylation of Transforming Growth Factor 13 Receptor Kinases", Proc. Natl. Acad. Sci. USA, 92:1565-1569 (1995).
Cheng, et al., "Novel Solution Phase Strategy for the Synthesis of Chemical Libraries Containinq Small Orqanic Molecules", J. Am. Chem. Soc., 118:2567-2573 (1996).

(56) References Cited

OTHER PUBLICATIONS

Cheng, et al., "Synthesis and SAR of Heteroaryl-phenyl-substituted Pyrazole Derivatives as Highly Selective and Potent Canine COX-2 Inhibitors", Bioorganic & Medicinal Chemistry Letters, 16:2076-2080 (2006).
Chu, et al., "Using Affinity Capillary Electrophoresis to Determine Binding Stoichiometries of Protein-Ligand Interactions", Biochemistry, 33:10616-10621 (1994).
Cirillo, et al. "The Non-Diaryl Heterocycle Classes of p38 MAP Kinase Inhibitors", Current Topics in Medicinal Chemistry, 2:1021-1035 (2002).
Clinical trial NCT03353753 Phase 3 Study of DCC-2618 vs Placebo in Advanced GIST Patients Who Have Been Treated With Prior Anticancer Therapies (invictus)—clinicaltrials.gov—Nov. 27, 2017.
Clinical trial NCT02571036—A Safety, Tolerability and PK Study of DCC-2618 in Patients With Advanced Malignancies—clinicaltrials. gov—Dec. 16, 2015.
Clinical trial NCT02571036—A Safety, Tolerability and PK Study of DCC-2618 in Patients With Advanced Malignancies—clinicaltrials. gov—Feb. 10, 2016.
Clinical trial NCT02571036—A Safety, Tolerability and PK Study of DCC-2618 in Patients With Advanced Malignancies—clinicaltrials. gov—May 25, 2017.
Clinical trial NCT02571036—A Safety, Tolerability and PK Study of DCC-2618 in Patients With Advanced Malignancies—clinicaltrials. gov—Nov. 3, 2015.
Clinical trial NCT02571036—A Safety, Tolerability and PK Study of DCC-2618 in Patients With Advanced Malignancies—clinicaltrials. gov—Oct. 29, 2015.
Clinical trial NCT02571036—A Safety, Tolerability and PK Study of DCC-2618 in Patients With Advanced Malignancies—clinicaltrials. gov—Oct. 8, 2015.
Clinical trial NCT02571036—A Safety, Tolerability and PK Study of DCC-2618 in Patients With Advanced Malignancies—clinicaltrials. gov—Sep. 17, 2018.
Clinical trial NCT03353753 Phase 3 Study of DCC-2618 vs Placebo in Advanced GIST Patients Who Have Been Treated With Prior Anticancer Therapies (invictus)—clinicaltrials.gov—Nov. 21, 2018.
Closier, et al., "Nitrofuryl Heterocyclics. 1", Journal of Medicinal Chemistry, 13(4):638-640 (1970).
Cockerill, et al., "Small Molecule Inhibitors of the Class 1 Receptor Tyrosine Kinase Family", Current Topics in Medicinal Chemistry, 2:1001-1010 (2002).
Colton, et al., "Affinity Capillary Electrophoresis: A Physical-Organic Tool for Studying Interactions in Biomolecular Recognition", Electrophoresis, 19:367-382 (1998).
Corless, et al., "Biology of Gastrointestinal Stromal Tumors," Journal of Clinical Oncology, 22(18):3813-3825 (2004).
Cortes, et al., "Results of Imatinib Mesylate Therapy in Patients with Refractory or Recurrent Acute Myeloid Leukemia, High-Risk Myelodysplastic Syndrime, and Mveloproliferative Disorders", Cancer, 97(11):2760-2766 (2003).
Cortes, Javier, et al., "Eribulin Monotherapy Versus Treatment of Physician's Choice in Patients With Metastatic Breast Cancer (Embrace): A Phase 3 Open-label Randomised Study", The Lancet, vol. 377, No. 9769, Mar. 1, 2011 (Mar. 1, 2011), pp. 914-923, ISSN: 0140-6736, DOI: 10.1016/S0140-6736(11)60070-6.
Cross, et al., "Inhibition of Glycogen Synthase Kinase-3 by Insulin Mediated by Protein Kinase B", Nature, 378:785-789 (1995).
Cudney, "Preface: Protein Crystallization and Dumb Luck", The Rigaku Journal, 16(1):1-7 (1999).
Dajani, et al. "Crystal Structur of Glycogen Synthase Kinas 3j3: Structural Basis for Phosphate-Primed Substrate Specificity and Autoinhibition", Cell, 105:721-732 (2001).
Dajani, et al., "Structural Basis for Recruitment of Glycogen Synthase Kinase 313 to the Axin-APC Scaffold Complex", EMBO, 22(3):494-501 (2003).

Daley, et al., "Induction of Chronic Myelogenous Leukemia in Mice by the P21 otcriat, Gene of the Philadelphia Chromosome," Science (Feb. 16, 1990) vol. 247, pp. 824-830.
Database Registry [Online] Chemical Abstracts Service, Columbus, Ohio, US; May 27, 2010, XP002777425, retrieved from STN accession No. 1225278-16-9 RN (2 pages).
Dies, H. et al, "Mutations of the BRAF gene in human cancer," Nature (Jun. 2002) 41 7: 949-954.
Davis, et al., "Iterative Size-Exclusion Chromatography Coupled with Liquid Chromatographic Mass Spectrometry to Enrich and Identify Tight-Binding Ligands from Complex Mixtures", Tetrahedron, 55:11653-11667 (1999).
De Boer, et al., "Synthesis and Characterization of Conjugated Mono- and Dithiol Oligomers and Characterization of Their Self-Assembled Monolayers", Langmuir, 19:4272-4284 (2003).
De Palma et al., "Angiopoietin-2 TIEs Up Macrophages in Tumor Angiogenesis" Clin Cancer Res; 17(16) Aug. 15, 2011.
De Silva, et al., "Gastrointestinal Stromal Tumors (GIST): C-kin Mutations, CD117 Expression, Differential Diagnosis and Targeted Cancer Therapy with Imatinib", Pathology Oncology Research, 9(1):13-19 (2003).
Debiec-Rychter, et al., "Mechanisms of Resistance to Imatinib Mesylate in Gastrointestinal Stromal Tumors and Activity of the PKC412 Inhibitor Against Imatinib-Resistant Mutants," Gastroenterology, 128(2):270-279 (2005).
Deciphera Pharmaceuticals LLC, "DCC-2618, a small molecule inhibitor of normal and mutant KIT kinase for treatment of refractory gastrointestinal stromal tumors (GIST)" (Presented on Sep. 24, 2011 at GIST Summit 2011 on "Gastrointestinal stromal tumors.").
Deciphera Pharmaceuticals LLC, "Deciphera Pharmaceuticals announces positive top-line results from INVICTUS pivotal phase 3 clinical study of Ripretinib in patients with advanced gastrointestinal stromal tumors", 1-3 (2019).
Deciphera Pharmaceuticals LLC, "Deciphera Pharmaceuticals Initiates Pivotal Phase 3 Clinical Study of Ripretinib (DCC-2618) in Second-line Patients with Gastrointestinal Stromal Tumors ("Intrigue" Study)", 1-2 (2018).
Deciphera Pharmaceuticals LLC, "Qinlock Full Prescribing Information", 1-18 (2020).
Deng, et al., "Expression, Characterization, and Crystallization of the Pyrophosphate-Dependent Phosphofructo-1-Kinase of Borrelia Burgdorferi", Archives of Biochemistry and Biophvsics, 371(2):326-331 (1999).
Dess, et al., "A Useful 12-1-5 Triacetoxyperiodiane (the Dess-Martin Periodiane) for Selective Oxidation of Primary or Secondary Alcohols and a Variety of Related 12-1-5 Species", J. Am. Chem., Soc., 113:7277-7287 (1991).
Dong, J., Overcoming Resistance TO BRAF and MEK inhibitors by Simultaneous Suppression of CDK4. InTech. Jan. 30, 2013. Melanoma—From Early Detection to Treatment, Chapter 1; abstract; p. 7, second paragraph; p. 9, figure 4; DOI: 10.5772/53620.
Dumas, "Preface", Current Topics in Medicinal Chemistry (2002).
Dumas, "Protein Kinase Inhibitors: Emerging Pharmacophores", Exp. Opin. Ther. Patent, 11:405-429 (2001).
Dumas, et al., "Discovery of a New Class of p38 Kinase Inhibitors", Bioorganic & Medicinal Chemistry Letters, 10:204 7-2050 (2000).
Dumas, et al., "Recent Developments in the Discovery of Protein Kinase Inhibitors From the Urea Ciass," Current Opinion in Drug Discovery & Development (2004) vol. 7, No. 5, pp. 600-616.
Ettmayer, et al., "Lessons Learned from Marketed and Investigational Prodrugs," Journal of Medicinal Chemistry (May 6, 2004) vol. 47, No. 10, pp. 2393-2404.
Ewing, "Critical Evaluation of Search Algorithms for Automated Molecular Docking and Database Screeninq", Journal of Computational Chemistry, 18(9):1175-1189 (1997).
Examination Report in Indian Patent App. No. 11241/DELNP/2014 dated Apr. 1, 2019.
Faderl et al., "The Biology of Chronic Myeloid Leukemia," *The New England Journal of Medicine* (Jul. 15, 1999) vol. 341. No. 3. pp. 164-172.

(56) References Cited

OTHER PUBLICATIONS

Farooqui, et al., "Interactions Between Neural Membrane Glycerophospholipid and Sphingolipid Mediators: A Recipe for Neural Cell Survival or Suicide", Journal of Neuroscience Research, 85:1834-1850 (2007).
Fathalla, "Synthesis of New Pyrazolo[1,5-a]pyrimidine Derivative Using 5-Aminouracil and Ketene Dithiacetal", Arch Pharm Res, 22(6):571-574 (1999).
Fathalla, et al., "Synthesis of New Uracil-5-Sulfonamide Derivatives and Immuno-Stimulatory Effect of a Chemically Modified Hemolymph of Biomphalaria Alexandrina on Schistosoma Manosi Infected Mice", Arch Pharm Res., 26(5):358-366 (2003).
Fathalla, et al., "Synthesis of New Uracil-5-Sulphonamide-p-Phenyl Derivatives and Their Effect on *Biomphalaria alexandrina* Snail's Nucleoproteins", Arch. Pharm. Res., 23(2):128-138 (2000).
Flatt, et al., "Synthesis of Thiol Substituted Oligoanilines for Molecular Device Candidates", Tetrahedron Letters, 44:6699-6702 (2003).
Fletcher, et al., "Diagnosis of Gastrointestinal Stromal Tumors: A Consensus Approach", 33(5):459-465 (2002).
Fletcher, et al., "KIT Mutations in GIS, Current Opinion in Genetics & Development," Science Direct, p. 3-7 (2007).
Frame, et al., "A Common Phosphate Binding Site Explains the Unique Substrate Specificity of GSK3 and Its Inactivation by Phosphorylation", Molecular Cell, 7:1321-1327 (2001).
Furyua, et al., "Addition of 4-Ethoxyimidazoles to Dimethyl Acetylenedicarboxylate and Transformation of the Adducts to Pyrimidian-5-yl Acetates", Chem. Pharm. Bull., 36(5):1669-1675 (1988).
Gajiwala, et al., "KIT kinase mutants show unique mechanisms of drug resistance to imatinib and sunitinib in gastrointestinal stromal tumor patients," Proceedings of the National Academy of Sciences of the USA 106(5):1542-1547 (2009).
Garcia-Tellado, et al., "Molecular Recognition in the Solid Waste State: Controlled Assembly of Hydrogen-Bonded Molecular Sheets", J. Am. Chem. Soc., 113:9265-9269 (1991).
George, et al., "Initial Results of Phase 1 Study of DCC-2618, a Broad-Spectrum Kit and PDGFRA Inhibitor, in Patients (PTS) with Gastrointestinal Stromal Tumor (GIST) by Number of Prior Regimes", European Society for Medical Oncology, 1-13 (2018).
Gishizky, et al., "Efficient transplantation of BCR-ABL-induced Chronic Myelogenous Leukemia-like Syndrome in Mice," Proc. Natl. Acad. Sci. (Apr. 1993) vol. 90, pp. 3755-3759.
Gorre et al, "Clinical Resistance to STI-571Cancer Therapy Caused by BCR-ABL Gene Mutation or Amplification," *Science* (Aug. 3, 2001) vol. 293, pp. 876-880.
Greene, et al., "Chapter 7: Protection for the Amino Group", in Protective Groups in Organic Synthesis, Third Edition, pp. 494-653 (1999).
Griffith, et al., "TPAP: Tetra-n-propylammonium Perruthenate, A Mild and Convenient Oxidant for Alcohols", Aldrichimica Acta, 23(1):13-19 (1990).
Guzel, "Investigation of the Relationship Between the Inhibitory Activity of Glycolic Acid Oxidase (GAO) and its Chemical Structure: Electron-Topological Approach", Journal of Molecular Structure, 366:131-137 (1996).
Haar, et al., "Structure of GSK313 Reveals a Primed Phosphorylation Mechanism", Nature Structural Bioloav, 8(7):593-596 (2001).
Hackler, et al., "The Syntheses of 5-Amino-3- t-butylisothiazole and 3-Amino-5- t-butylisothiazole," J. Heterocyc/ic Chem. (Nov.-Dec. 1989) vol. 26, pp. 1575-1578.
Haesslein, et al., "Recent Advances in Cyclin-Dependent Kinase Inhibition. Purine-Based Derivatives as Anti-Cancer Agents. Roles and Perspectives for the Future", Current Topics in Medicinal Chemistry, 2:1037-1050 (2002).
Hearing Notice in Indian Patent App. No. 11241/DELNP/2014 dated Jan. 24, 2020.
Heegaard, et al., "Affinity Capillary Electrophoresis: Important Application Areas and Some Recent Developments", Journal ofChromatoqraphy B, 715:29-54 (1998).

Heinrich, et al., "Molecular Correlates of Imatinib Resistance in Gastrointestinal Stromal Tumors," Journal of Clinical Oncology, 24(29):4764-4774 (2006).
Heinrich, et al., "Primary and Secondary Kinase Genotypes Correlate With the Biological and Clinical Activity of Sunitinib in Imatinib-Resistant Gastrointestinal Stromal Tumor," Journal of Clinical Oncology, 26(33):5352-5359 (2008).
Honda, et al., "Determination of the Association Constant of Monovalent Mode Protein-Sugar Interaction by Capillary Zone Electrophoresis", Journal of Chromatography, 597:377-382 (1992).
Hu, et al., "Capillary Electrophoresis for the Analysis of Biopolymers", Anal., Chem., 74:2833-2850 (2002).
Huang, et al., "Inhibition of Nucleoside Transport by Protein Kinase Inhibitors", The Journal of Pharmacolo and Experimental Therapeutics, 304 2 :753-760 (2003).
Hubbard, "Crystal Structure of the Activated Insulin Receptor Tyrosine Kinase in Complex with Peptide Substrate and ATP Analo", EMBO, 16(18):5573-5581 (1997).
Hubbard, et al., "Crystal Structure of the Tyrosine Kinase Domain of the Human Insulin Receptor", Nature, 374:746-754 (1994).
Hughes, et al., "Modulation of the Glycogen Synthase Kinase-3 Family by Tyrosine Phosphor lation", EMBO, 12 2 :803-808 (1993).
Huse et al, "The Conformational Plasticity of Protein Kinases," *Cell* (May 3, 2002) vol. 109, pp. 275-282.
Huse, et al., "Crystal Structure of the Cytoplasmic Domain of the Type I TGFl3 Receptor in Complex with FKBP12", Cell, 96:425-436 (1999).
Huse, et al., "The TGFl3 Receptor Activation Process: An Inhibitor-to Substrate-Binding Switch", Molecular Cell, 8:671-682 (2001).
Igarashi, et al., "Antimicrobial Activities of 2-arylthio-N-alkylmaleimides", Journal of Industrial Microbiolo, 9:91-96 (1992).
International Human Genome Sequencing Consortium, "Initial Sequencing and Analysis of the Human Genome", Nature, 409:860-921 (2001).
International Search Report and Written Opinion from PCT/US2012/041378, dated Sep. 17, 2012.
International Search Report and Written Opinion from PCT/US2017/035005, dated Feb. 22, 2018.
International Search Report and Written Opinion from PCT/US2019/016148, dated Apr. 17, 2019.
International Search Report and Written Opinion from PCT/US2019/016161, dated Apr. 23, 2019.
International Search Report and Written Opinion from PCT/US2020/045876, dated Oct. 22, 2020.
International Search Report and Written Opinion from PCT/US2020/067557, dated Apr. 23, 2021.
International Search Report and Written Opinion from PCT/US2020/067560, dated Apr. 23, 2021.
International Search Report and Written Opinion from WO2008/034008 A3, dated Apr. 11, 2008.
International Search Report issued for PCT/US2008/060833, dated Sep. 30, 2008.
International Search Report issued for PCT/US2008/060867, dated Sep. 29, 2008.
International Search Report issued for PCT/US2008/060896, dated Sep. 29, 2008.
Ishida, et al., "Molecular Arrangement and Electrical Conduction of Self-Assembled Monola ers Made from Terphen I Thiols", Surface Sciences, 514:187-193 (2002).
Islip, et al., "Nitrofuryl Heterocyclics 3", Journal of Medicinal Chemistry, 16(11):1309-1310 (1973).
Jackson, et al., "N-Terminal Mutations Activate the Leukemogenic Potential of the M risto lated form of c-abl", EMBO, 8(2):449-456 (1989).
Jackson, et al., "Pyridinylimidazole Based p38 MAP Kinase Inhibitors", Current Topics in Medicinal Chemist, 2:1011-1020 (2002).
Janku Filip et al., "Pharmacokinetic-driven phase I study of DCC-2618 a pan-KIT and PDGFR inhibitor in patients (pts) with gastrointestinal stromal tumor (GIST) and other solid tumors," *J. Clin. Oncol.* (2017) No. 15, Suppl 2515.
Janku, et al., "Abstract CT058: Ripretinib (DCC-2618) pharmacokinetics (PK) in a Phase I study in patients with gastrointestinal stromal

(56) References Cited

OTHER PUBLICATIONS tumors (GIST) and other advanced malignancies: A retrospective evaluation of the PK effects of proton pump inhibitors (PPIs)", American Association for Cancer Research, 79(13):1-4 (2019).
Jiang, et al., ""Soft Docking": Matching of Molecular Surface Cubes", J. Mol. Biol., 219:79-102 (1991).
Jiang, et al., "Synthesis and SAR Investigations for Novel Melanin-Concentrating Hormone 1 Receptor (MCH1) Antagonists Part 1. The Discovery of Arylacetamides as Viable Replacements for the Dihydropyrimidione Moiety of an HTS Hit", J. Med. Chem., 50:3870-3882 (2007).
Johnson, "Circular Dichroism Spectroscopy and the Vacuum Ultraviolet Region", Ann. Rev. Phys. Chem., 29:93-114 (1978).
Johnson, "Protein Secondary Structure and Circular Dichroism: A Practical Guide", Proteins: Structure, Function, and Genetics, 7:205-214 (1990).
Johnson, et al., "An Evaluation of the Effect of Light Stabilisers on the Exterior Durability of Polyester Powder Coatings for the Architectural Market", Surface Coatings International, 3:134-141 (1999).
Johnson, et al., "The Stereochemistry of Oxidation at Sulfur Oxidation of 2-Thiabicyclo[2.2.1]Hpetane", Tetrahedron, 25:5649-5653 (1969).
Katritzky, et al., "Novel Chromophoric Heterocycles Based on Maleimide and Naphthoquinone", J. Heterocyclic Chem., 26:885-892 (1989).
Kern, et al., "Synthese von Makromolekeln einheitlicher Brol3e. II Mitt: Syntheses neuer Diololigo-urethane nach dem Duplikationsverfahren", Makromolekulara Chemie, 16:89-107 (1955).
Kettle et al., "Discovery of N-(4-{[5-Fluoro-7-(2-methoxyethoxy)quinazolin-4-yl]amino}phenyl)-2-[4-(propan-2-yl)-1H-1,2,3-triazol-1-yl]acetamide (AZD3229), a Potent Pan-KIT Mutant Inhibitor for the Treatment of Gastrointestinal Stromal Tumors" Journal of Medicinal Chemistry (2018), 61(19), 8797-8810.
Kim, et al., "Solid Phase Synthesis of Benzamidine and Butylamine-Derived Hydantoin Libraries", Molecular Diversity, 3:129-132 (1998).
Klayman, et al., "The Reaction of S-Methiodide Derivatives of Activated Thioureas with Hydroxylic Compounds. A Novel Synthesis of Mercaptans", J. Org. Chem., 37(10):1532-1537 (1972).
Kleywegt, et al., "Detection, Delineation, Measurement and Display of Cavities in Macromolecular Structures", Acta Cryst, D50:178-185 (1994).
Koch, et al., "QSAR and Molecular Modelling for a Series of Isomeric X-Sulfanilamido-1-phenylpyrazoles", Quant. Struct. Act. Relat., 12:373-382 (1993).
Kolch, W., "Meaningful relationships: the regulation of the Ras/Raf/MEKJERK pathway by protein interactions," Biochern. J (2000) 351: 289-305.
Konopka, et al., "Cell Lines and Clinical Isolates Derived From Ph-positive Chronic Myelogenous Leukemia Patients Express c-abl Proteins With a Common Structural Alteration," Proc. Natl. Acad. Sci. (Mar. 1985) vol. 82, pp. 1810-1814.
Krasovitskii, et al., "Synthesis and Spectral-Luminescence Properties of Hetarylethylene Derivatives of 2,5-Diphenyloxazole and 2,5-Diphenyl-1,3,4-Oxadiazole", Khimiya Geterotsiklicheskikh Soedinenii, 5:617-621 (1982).
Kuhn, et al., "The Genesis of High-Throughput Structure-Based Drug Discovery using Protein Crystallography", Analytical Techniques, Current Opinion in Chemical Biology, 6:704-710 (2002).
Kumar, et al., "P38 Map Kinases: Key Signalling Molecules as Therapeutic Targets for Inflammatory Diseases", Nature Reviews Drug Discovery, 2:717-726 (2003).
Kundrot, "Which Strategy for a Protein Crystallization Project", CMLS, Cell. Mol. Life Sci., 61:525-536 (2004).
Kundu, et al., "Depropargylation Under Palladium-Copper Catatlysis: Synthesis of Diaryl Sulfides", Tetrahedron, 57:5885-5895 (2001).
Kurogi, et al., "Discovery of Novel Mesangial Cell Proliferation Inhibitors Using a Three-Dimensional Database Searching Method", J. Med. Chem., 44:2304-2307 (2001).

Kuse, et al., Synthesis of azide-fluoro-dehydrocoelentcrazine analog as a photoaffinitylabeling probe and photolysis of azide-fluoro-coelenterazine; Tetrahedron Lett. (2005) 61: 5754-5762.
Kwong, et al., "A General, Efficient, and Inexpensive Catalyst System for the Coupling Aryl Iodides and Thiols", Organic Letters, 4(20):3517-3520 (2002).
Laskowski, "Surfnet: A Program for Visualizing Molecular Surfaces, Cavities, and Intermolecular Interactions", Journal of Molecular Graphics, 13:323-330 (1995).
Leca, et al., "A New Practical One-Pot Access to Sulfonimidates", Organic Letters, 4(23):4093-4095 (2002).
Lefevre, et al., "Roles of Stem Cell Factor/c-Kit and Effects of Glivec®/STI571 in Human Uveal Melanoma Cell Turmorigenesis", Journal of Biological Chemistry, 279(30):31769-31779 (2004).
Lesort, et al., "Insulin Transiently Increases Tau Phosphorylation: Involvement of Glycogen Synthase Kinase-3f3 and Fyn Tyrosine Kinase", Journal of Neurochemistry, 72(2):576-584 (1999).
Leung, et al., "The Difluoromethylensulfonic Acid Groups as a Monoanionic Phosphate Surrogate for Obtaining PTP1 B Inhibitors", Bioorganic & Medicinal Chemistry, 10:2309-2323 (2002).
Li, et al., "Targeting Serine/Threonine Protein Kinase B/Akt and Cell-cycle Checkpoint Kinases for Treating Cancer", Current Topics in Medicinal Chemistry, 2:939-971 (2002).
Li, et al., "The P190, {210, and P230 Forms of the BCR/ABL Oncogene Induce a Similar Chronic Myeloid Leukemia-like Syndrome in Mice but Have Different Lymphoid Leukemogenic Activity", J. Exp. Med., 189(9):1399-1412 (1999).
Lim et al., "Current research and treatment for gastrointestinal stromal tumors" World Journal of Gastroenterology (2017), 23(27), 4856-4866, Publisher: Baishideng Publishing Group Inc.
Link, et al., "Synthesis of 8-Substituted 5-Deazaflavins", J. Heterocyclic Chem, 22:841-848 (1985).
Lipinski, et al., "Experimental and Computational Approaches to Estimate Solubility and Permeability in Drug Discovery and Development Settings", Advanced Drug Delivery Reviews, 23:3-25 (1997).
Longley et al., "Somatic c-Kit activating mutation in urticaria pigmentosa and aggressive mastocytosis: establishment of clonality in a human mast cell neoplasm," Nature Genetics, 12(3):312-314 (1996).
Loren, et al., "NH-1,2,3-Triazoles from Azidomethyl Pivalate and Carbamates: Base-Labile N-Protecting Groups", Synlett, 18:2847-2850 (2005).
Lorenzi, et al., "Amino Acid Ester Prodrugs of 2-Bromo-5, 6-dichloro-1-([3-D-ribofuranosyl)benzimidazole Enhance Metabolic Stability In Vitro and In Vivo," The Journal of Phannaco/ogy and Experimental Therapeutics (2005) vol. 314, No. 2 pp. 883-890.
Lowinger, et al., "Design and Discovery of Small Molecules Targeting Raf-1 Kinase", Current Pharmaceutical Design, 8:2269-2278 (2002).
Ma, et al., "c-Met Mutational Analysis in Small Cell Lung Cancer: Novel Juxtamembrane Domain Mutations Regulating Cytoskeletal Functions", Cancer Research, 63:6272-6281 (2003).
Ma, et al., "c-Met: Structure, Functions and Potential for Therapeutic Inhibition", Cancer and Metastasis Reviews, 22:309-325 (2003).
Magnuson, et al, "The Raf-I serine/threonine protein kinase," Seminars in Cancer Biology. (1994) 5: 247-253.
Mallakpour, et al., "Uncatalyzed Polymerization of Bistriazolinediones with Electron-Rich Aromatic Compounds via Electrophilic Aromatic Substitution", Journal of Polymer Science: Part A: Polymer Chemistry, 27:217-235 (1989).
Mamaev, et al., "Synthesis of 2,5'—Bipyrimidines from Substituted 5-Cyanopyrimidines", Khimiya Geterotsiklicheskikh Soedinenni, 24(3):371-375- (1988).
March's Advanced Organic Chemisto.::: Reactions Mechanisms and Structure Fifth Edition, Smith and March Editors, Wiley-Interscience Publication (2001).
March, et al., "Tautomerism", from March's Advanced Organic Chemisto.::, 4th Edition, WileyInterscience, pp. 69-74.
Martinez, et al., "First Non-ATP Competitive Glycogen Synthase Kinase 313 (GSK-313) Inhibitors: Thiadizolidinones (TDZD) as Potential Drugs for the Treatment of Alzheimers Disease", J. Med. Chem., 45(2002)1292-1299 (2002).

(56) References Cited

OTHER PUBLICATIONS

Mattsson, et al., "Six X-Linked Agammaglobulinemia-Causing Missense Mutations in the Src Homology 2 Domain of Bruton's Tyrosine Kinase: Phosphotyrosine-Binding and Circular Dichroism Analysis", Journal of Immunoloav, pp. 4170- 4177 (2000).
Mazzieri, R et al., Targeting the ANG2/TIE2 Axis Inhibits Tumor Growth and Metastasis by impairing Angiogenesis and Disabling Rebounds of Proangiogenic Myelid Cells. Cell. Apr. 12, 2001, vol. 19, pp. 512-526; DOI: 10.1016/j.ccr.2001.02.005.
McPherson, "Current Approaches to Macromolecular Crystallization", Eur. J. Biochem., 189:1-23 (1990).
Medebielle, et al., "A Convenient Synthesis of Perfluoroalkylated and Fluorinated-Aryl Nitrogen Bases by Electrochemically Induced SRN1 Substitution", J. Org. Chem., 61:1331-1340 (1996).
Medebielle, et al., "A New Convenient Synthesis of 5-Aryl Uracils Using SRN1 Aromatic Nucleophilic Substitution", Tetrahedron Letters, 34(21):3409-3412 (1993).
Mikhaleva, et al., "Relative Reactivities of the Chlorine Atoms of 2,2',4-Trichloro-4',5-Dipyrimidinyl in its Reaction with Piperidine", Khimiya Geterotsiklicheskikh Soedinenii, 6:821-826 (1979).
Mol, "Structural Basis for the Autoinhibition and STI-571 Inhibition of c-Kit Tyrosine Kinase," The Journal of Biological Chemistry, 279(30):31655-31663 (2004).
Morris, et al., "Automated Docking of Flexible Ligands to Macromolecules", AutoDock Website, www.scripps.edu/mb/olson/doc/autodock/, printed Mar. 3, (2005).
Morris, et al., "Automated Docking Using a Lamarckian Genetic Algorithm and an Empirical Binding Free Energy Function", Journal of Computational Chemistry, 19(14):1639-1662 (1998).
Morstyn, et al., "Stem Cell Factor is a Potent Synergistic Factor in Hematopoiesis", Oncology, 51:205-214 (1994).
Moss, et al., Basic Terminology of Stereochemistry, Pure & Appl. Chem., 6812):2193-2222 (1996).
Muller, "Glossary of Terms Used in Physical Organic Chemistry", Pure & Appl. Chem., 66(5):1077-1184 (1994).
Muller, et al., "A General Synthesis of 4-Substituted 1,1-Dioxo-1,2,5-thiadiazolidin-3-ones Derived from α-Amino Acids", J. Org. Chem., 54:4471-473 (1989).
Murayama, et al., "JNK (c-Jun NH2 Terminal Kinase) and p38 During Ischemia Reperfusion Injury in the Small Intestine" Transplantation, 81(9):1325-1330 (2006).
Mutlib, et al., "Disposition of 1[3-(Aminomethyl)phenyl]-N-[3-fluoro-2'-(methylsulfonyl)-[1, 1 '-biphenyl]-4-yl]-3(trifluomethyl)-1 H-pyrazole-5-carboxamide (DPC 423) by Novel Metabolic Pathways. Characterization of Unusual Metabolites by Liquid Chromatography/Mass Spectrometrv and NMR", Chem. Res. Toxicol., 15:48-62 (2002).
Mutlib, et al., "P450-Mediated Metabolism of 1-[3-(Aminomethyl)phenyl]-N-[3-fluoro-2'-(methylsulfonyl)-[1, 1 '-biphenyl]-4-yl]-3(trifluomethyl)-1 H-pyrazole-5-carboxamide (DCP 423) and Its Analogues to Aldoximes. Characterization of Glutathione Conjugates of Postulated Intermediates Derived from Aloximes", Chem. Res. Toxicol., 15:63-75 (2002).
Nagano, M. et al. "Studies on Organic Sulfur Compounds. XIV. The Reaction of N-alkoxy-carbonyl-N'-(2-thiazolyl)thioureas with some oxidants." Chemical and Pharmaceutical Bulletin. vol. 21, No. 11, pp. 2408-2416. ISSN: 0009-2363. Nov. 1973.
Nagar, et al., "Crystal Structures of the Kinase Domain of c-Abl in Complex with the Small Molecule Inhibitors PD173955 and Imatinib (STI-571)", Cancer Research, 62:4236-4243 (2002).
Nagata, et al., "Identification of a point mutation in the catalytic domain of the protooncogene c-kit in peripheral blood mononuclear cells of patients who have mastocytosis with an associated hematologic disorder," Proc. Natl. Acad. Sci. USA, 92(23):10560-10564 (1995).
Nager, et al., "Structural Basis for the Autoinhibition of c-Abl Tyrosine Kinase," Cell (Mar. 21, 2003) vol. 112, pp. 859-871.

Nakopoulou, et al., "c-Met Tyrosine Kinase Receptor Expression is Associated with Abnormal !3-catenin Expression and Favourable Prognostic Factors in Invasive Breast Carcinoma", Histopatholoav, 36:313-325 (2000).
Nantaka-Namirski, et al., "Condensation Reaction of Ethyl (4-Uracil)— Acetate with Ethyl Orthoformate", ACTA Polon. Pharm XXVII, 28(5):455-463 (1971).
National Academy of Sciences, "Abstracts of Papers Presented at the Autumn Meetinq, Nov. 14-16, 1960", Science, 132:1488-1501 (1960).
Nicolaou, et al., "Molecular Design and Chemical Synthesis of a Highly Potent Epothilone", ChemMedChem, 1:41-44 (2006).
Nikolaev, et al., "Solubility Polytherm in the System HNO3-H2O-(C4H9O)PO(C4H9)2", Dokladv Akademii Nauk SSSR, 160(4):841-844 (1965).
Ning, et al., "Activating Mutations of c-Kit at Codon 816 Confer Drug Resistance in Human Leukemia Cells," Leukemia and Lymphoma, 41(5-6):513-522 (2001).
Nofal, et al., "Synthesis of Novel Uracil-5-Sulphonamide Derivatives of Possible Biological Activity", Egypt J. Chem., 33(4):375-380 (1990).
Nowell et al., "A Minute Chromosome in Human Chronic Granulocytic Leukemia," Science (Nov. 18, 1960) vol. 132, p. 1497.
O'Dell, et al., "Treatment of Rheumatoid Arthritis with Methotrexate Alone, Sulfasalazine and Hydroxychloroquine, or a Combination of All Three Medications", New England J. Med., 334(20):1287-1291(1996).
O'Neill, "Targeting Signal Transduction as a Strategy to Treat Inflammatory Diseases", Nature Review Drug Discovery, Published Online 9 Jun. 2006, www.nature.com/reviews/druqdisc.
Okano, et al., "o-Bromophenylzinc Compound: A Readily Available and Efficient Synthetic Equivalent of o-Phenylene 1-Anion 2-Cation", Tetrahedron Letters 39:3001-3004 (1998).
Okishio, et al., "Differential Ligand Recognition by the Src and Phosphatidylinositol 3-Kinase Src Homology 3 Domains: Circular Dichroism and Ultraviolet Resonance Raman Studies", Biochemistrv, 42:208-216 (2003).
Okishio, et al., "Identification of Tyrosine Residues Involved in Ligand Recognition by the Phosphatidylinositol 3-Kinase Src Homology 3 Domain: Circular Dichroism and UV Resonance Raman Studies", Biochemistrv, 40:15797-15804 (2001).
Okishio, et al., "Role of the Conserved Acidic Residue Asp21 in the Structure of Phosphatidylinositol 3-Kinase Src Homlgy 3 Domain: Circular Dichroism and Nuclear Maqnetic Resonance Studies", Biochemistrv 40:119-129 (2001).
Okram, Barun et al: "A General Strategy for Creating "Inactive-Conformation" Abl Inhibitors" Chemistry&Biology (Cambridge, MA, US), 13(7), 779-786 CODEN: CBOLE2; ISSN: 1074-5521, 2006, XP002469183 table 1 the whole document.
Palmer, Brian, D. et al: "Structure-Activity Relationships for 2-Anilino-6-Phenylpyrido[2,3-d]Pyrimidin-7(8H)-Ones as Inhibitors of the Cellular Checkpoint Kinase Wee1" Bioorganic & Medicinal Chemistry Letters, 15(7), 1931-1935 CODEN: BMCLE8; ISSN: 0960-894X, 2005, XP004789411 p. 1933.
Parang, et al., "Mechanism-based Design of a Protein Kinase Inhibitor", Nature Structural Bioloav, 8(1):37-41 (2001).
Pargellis, et al., "Inhibition of p38 MAP Kinase by Utilizing a Novel Allosteric Binding Site", Nature Structural Bioloav, 9(4):268-272 (2002).
Park, et al., "Mechanism of *met* Oncogene Activation", Cell, 45:895-904 (1986).
Pearlman, et al., "Assisted Model Building with Energy Refinement", Amber Home Page, amber.scripts.edu.
Pedersen, "The Preparation of Some N-Methyl-1,2,3-Triazoles", Acta Chimica Scandinavica, 13(5):888-892 (1959).
Peng, et al., "Identification of Novel Inhibitors of BCR-ABL Tyrosine Kinase via Virtual Screening", Bioorganic & Medicinal Chemistry Letters, 13:3693-3699 (2003).
Pereira, et al., "The Role of c-kit and Imatinib Mesylate in Uveal Melanoma", Journal of Carcinogenesis, 4:19 (2005), downloaded from www.carcinogenesis.com/content/4/1/19, Sep. 3, 2008.
Peyssonnaux, C. et al, "The RaflMEK/ERK pathway: new concepts of activation," Biol. Cell (2001) 93: 53-62.

(56) References Cited

OTHER PUBLICATIONS

Picard, et al., Inhibitors of Acyl-CoA: Cholesterol O-Acyltrasferase. 17. Structure-Activity Relationships of Several Series of Compounds.

Pierrat, et al, "Solid Phase Synthesis of Pyridine-Based Derivatives from a 2-Chloro-5-Bromopyridine Scaffold," J Comb. Chem. (2005) 7 (6): 879-886.

Pluk et al., "Autoinhibition of c-Abl," *Cell* (Jan. 25, 2002) vol. 108, pp. 247-259.

Ponzetto, et al., "A Novel Recognition Motif for Phosphatidylinositol 3-Kinase Binding Mediates its Association with the Hepatocyte Growth Factor/Scatter Factor Receptor", Molecular and Cellular Bioloav, 13(8):4600-4608 (1993).

Raimbaul T, et al., "Effects of pH and KCl on the Conformations of Creatine Kinase from Rabbit Muscle", Eur. J. Biochem., 234:570-578 (1995).

Ranatunge, et al, "Synthesis and Selective Cyclooxygenase-2 Inhibitory Activity of a Series of Novel, Nitric Oxide Donor-Containing Pyrazoles," J Med Chem. (2004) 47: 2180-2193.

Reardon, D. et al., "Effect of CYP3A—inducing anti-epileptics on sorafenib exposure: results of a phase II study of sorafenib plus daily temozolomide in adults with recurrent gliosblastoma", J. Neurooncol. (2011), 101: pp. 57-66.

Rebek, et al. "Convergent Functional Groups: Synthetic and Structural Studies", J. Am. Chem. Soc., 107:7476-7481 (1985).

Rebek, et al., "Convergent Functional Groups. 2. Structure and Selectivity in Olefin Epoxidation with Peracids", J. Org. Chem., 51:1649-1653 (1986).

Reed, et al., "Circular Dichroic Evidence for an Ordered Sequence Ligand/Binding Site Interactions in the Catalytic Reaction of the cAMP-Dependent Protein Kinase", Biochemistry, 24:2967-2973 (1985).

Regan, et al., "Pyrazole Urea-Based Inhibitors of p38 MAP Kinase: From Lead Compound to Clinical Candidate", J. Med. Chem., 45:2994-3008 (2002).

Regan, et al., "Structure-Activity Relationships of the p38a MAP Kinase Inhibitor 1-(5-tert-Butyl-2-p-tolyl-2H-pyrazol-3-yl)-3-[4-(2-morpholi n-4-yl-ethoxy)naph-thalen-1-yl]urea (BI RB 796)", J. Med. Chem., 46:4676-4686 (2003).

Reis, R. et al., "Molecular characterization of PDGFR-α/PDGF-A and c-KIT/SCF in gliosarcomas", Cellular Oncology, 2005; 27: pp. 319-326.

Rooney, et al., "Inhibitors of Gylcolic Acid Oxidase. 4-Substituted 3-Hydroxy-1 H-pyrrole-2,5-dione Derivatives", J. Med. Chem., 26(5):700-714 (1983).

Roux, et al., "ERK and p38 MAPK—Activated Protein Kinases: a Family of Protein Kinases with Diverse Biological Functions", Microbiology and Molecular Biology Reviews, 68(2):320-344 (2004).

Rowley, "A New Consistent Chromosomal Abnormality in Chronic Myelogenous Leukaemia identified by Quinacrine Flourescence and Giemsa Staining," Nature (Jun. 1, 1973) vol. 243, pp. 290-293.

Rubin, et al., "Gastrointestinal stromal tumour," The Lancet Oncology, 369(9574):1731-1741 (2007).

Russell, et al., "3[3-(Piperdin-1-yl)propyl]indoles as Highly Selective h5-HT1D Receptor", J. Med. Chem., 42:4981-5001 (1999).

Rutkowski, et al., "Gastrointestinal stromal tumours (GIST)—2018", Oncology in Clinical Practice, 14(6):399-407 (2019).

Saiga, et al.,"Consecutive Cross-Coupling of o-Phenylenedizinc Compound with Acyl and/or Aryl Halides in the Presence of Pd(0)—tris(2,4,6-trimethoxyphenyl)phosphine", Tetrahedron Letters, 41:4629-4632 (2000).

Sakamoto, et al., "Condensed Heteroaromatic Ring Systems. XIX. Synthesis and Reactions of 5-(Tributylstannyl)Isoxazoles", Tetrahedron, 4 7(28):5111-5118 (1991).

Sakuma, et al., "c-*kit* Gene Mutations in Intracranial Germinomas", Cancer Sci, 95(9):716-720 (2004).

Salgia, "Studies on c-Kit and c-Met in Lung Cancer with Similarities to Stem Cells," Microscopy Society of America, 11(2):1-30 (2005).

Satsangi, et al., "1-(4-Substituted-thiazol-2-yl)hydatoins as Anti-inflammatory and CNS—Active Agents", Pharmazie, 38:341-342 (1983).

Sawyers, "Chronic Myeloid Leukemia," *The New England Journal of Medicine* (Apr. 29, 1999) vol. 340, No. 17, pp. 1330-1340.

Schindler et al., "Structural Mechanism for STI-571 Inhibition of Abelson Tyrosine Kinase," *Science* (Sep. 15, 2000) vol. 289, pp. 1938-1942.

Schlosser, et al., "Regiochemically Flexible Substitutions of Di-, Tri-, and Tetrahalopy:ridines: The Trialkylsily Trick," J Org. Chem. (2005) 70: 2494-2502.

Schmidt, et al., "Germline and Somatic Mutations in the Tyrosine Kinase Domain of the MET proto-oncogene in Papillary Renal Carcinomas", Nature Genetics, 16:68-73 (1997).

Schmidt, et al., "Novel Mutations of the MET Proto-oncogene in Papillary Renal Carcinomas", Oncogene, 18:2343-2350 (1999).

Schneeweiss Mathias, et al., "The KIT and PDGFRA switch-control inhibitor DCC-2618 blocks growth and survival of multiple neoplastic cell types in advanced mastocytosis," *Haematologica* (2018) vol. 103, No. 5, pp. 799-809.

Schneeweiss Mathias, et al., "The Multi-Kinase Inhibitor DCC-2618 Inhibits Proliferation and Survival of Neoplastic Mast Cells and Other Cell Types Involved in Systemic Mastocytosis," *Blood* (2016) vol. 128, No. 22, pp. 1965.

Seimiya, et al., "Telomere Shortening and Growth Inhibition of Human Cancer Cells by Novel Synthetic Telomerase Inhibitors MST-312, MST-295, and MST-199", Molecular Cancer Therapeutics, 1:657-665 (2002).

Seminario, et al., "Theoretical Study of a Molecular Resonant Tunneling Diode", J. Am. Chem. Soc., 122:3015-3020 (2000).

Seto, et al. "2-Substituted-4-aryl-6, 7 ,8,9-tetrahydro-5/ 1-p)'Timido [4, 5-b] [1,5 Joxazocin-5-oneasastrncturallynewNK1 antagonist," Biorg Nied Chem. Tea. (2005) 15: 1485-1488.

Shah et al., "Overriding Imatinib Resistance with a Novel ABL Kinase Inhibitor," *Science* (Jul. 16, 2004) vol. 305, pp. 399-401.

Shah, et al., "Circular Dichroic Studies of Protein Kinase C and its Interactions with Calcium and Lipid Vesicles", Biochimica et Biophvsica Acta, 1119:19-26 (1992).

Shi et al., "Abnormal Diels-Alder Reaction of 5-Alkoxythiazoles with Highly Reactive Dienophiles; 4-Phenyl-3H-1,2,4-triazole-3,5(4H)-dione, Diethyl Azodicarboxylate, and Diethyl Oxomalonate", Bull. Chem. Soc. Jpn., 65:3315-3321 (1992).

Shinkai, et al., "Coenzyme Models, Part 45. Synthesis of Atropisomeric Flavins and their Novel Redox-induced Racemisation", J. Chem. Soc. Perkin Trans., pp. 313-319 (1988).

Shiozaki, et al., "Impaired Differentiation of Endocrine and Exocrine Cells of the Pancreas in Transgenic Mouse Expressing the Truncated Type II Activin Receptor", Biochimica et Biophysica Acta, 1450:1-11 (1999).

Sihto, et al., "KIT and Platelet-Derived Growth Factor Receptor Alpha Tyrosine Kinase Gene 1—30 Mutations and KIT Amplifications in Human Solid Tumors," Journal of Clinical Oncology, 23(1):49-57 (2005).

Sircar et al., "Synthesis of 4-Hydroxy-N-[5-(hydroxymethyl)-3-isoxazolyl]2-methyl-2H-1,2-bsnzo-thiazine-3- carboxamide 1,1-Dioxide and [(5-Methyl-3-isoxazolyl)amino]oxoacetic Acid. Major Metabolites of Isoxicam", *J. Org. Chem.* (1985) vol. 50, pp. 5723-5727.

Smith et al., "Ripretinib (DCC-2618) is a switch control kinase inhibitor of a broad spectrum of oncogenic and drug-resistant KIT and PDGFRA variants," *Cancer Cell* (2019), vol. 35, No. 5, pp. 738-759.

STN Registry Database RN 1225278-16-9.

Stout, et al., "High-Throughput Structural Biology in Drug Discovery: Protein Kinases", Current Pharmaceutical Design, 10:1069-1082 (2004).

Sugden, et al., ""Stress-Responsive" Mitogen-Activated Protein Kinases (c-Jun N-Terminal Kinases and p38 Mitogen-Activated Protein Kinases) in the Myocardium", Circulation Research—Journal of the American Heart Association, 83:345-352 (1998).

Tanis, et al., "Two Distinct Phosphorylation Pathways Have Additive Effects on Abl Family Kinase Activation", Molecular and Cellular Bioloav, 23(11):3884-3896 (2003).

(56) References Cited

OTHER PUBLICATIONS

Tanno, F. et al., "Evaluation of Hypromellose Acetate Succinate (HPMCAS) as a Carrier in Solid Dispersions", Journal of Drug Development and Industrial Pharmacy, vol. 30, No. 1, pp. 9-17 (2004).

Tarn, et al., "Analysis of KIT Mutations in Sporadic and Familial Gastrointestinal Stromal Tumors: Therapeutic Implications through Protein Modeling," Clinical cancer research : an official journal of the American Association for Cancer Research, 11(10):3668-3677 (2005).

Teague, "Implications of Protein Flexibility for Drug Discovery", Nature Reviews, 2:527-541 (2003).

Tian, et al., "Activating c-kit Gene Mutations in Human Germ Cell Tumors," American Journal of Pathology, 154(6):1643-1647 (1999).

Tominaga, et al., "General model for Estimation of the Inhibition of Protein Kinases Using Monte Carlo Simulations", J. Med. Chem., 47:2534-2549 (2004).

Tremblay, et al., "Efficient Solid-Phase Synthesis of Sulfahydantoins", J. Comb. Chem., 4:429-435 (2002)

Tsuzuki, et al., "Synthesis and Structure-Activity Relationships of Novel ?-Substituted 1,4-Dihydro-4-oxo-1-(2-thiazolyl)-1,8-napthyridine-3-carboxylic Acids as Antitumor Agents. Part 2", J. Med. Chem., 47:2097-2109 (2004).

Van Etten, "Cycling, Stressed-out and Nervous: Ceiiuiar Functions of c-Abi," Trends in Cell Biology (May 1999) vol. 9, pp. 179-186.

Venter, et al., "The Sequence of the Human Genome", Science, 291:1304-1351, Feb. 16, 2001; Erratum, Jun. 8, 2001.

Von Bubnoff, et al., "BCR-ABL gene mutations in relation to clinical resistance of Philadelphia-chromosome-positive leukemia to ST1571. a prospective study," The Lancet (Feb. 9, 2002) vol. 359, pp. 487-491.

Waetzig, et al., "Review Article: Mitogen-Activated Protein Kinases in Chronic Intestinal Inflammation—Targeting Ancient Pathways to Treat Modern Diseases", Aliment Pharmacol Ther, 18:17-32 (2003).

Wan et al., "Mechanism of Activation of the RAF-ERK Signaling Pathway by Oncogenic Mutations of B-RAF," Cell (Mar. 19, 2004) vol. 116. pp. 855-867.

Wardelmann, "Acquired resistance to imatinib in gastrointestinal stromal tumours caused by multiple KIT mutations," The Lancet Oncology, 6(4):249-251 (2005).

Welker, et al., "Glucocorticoid-Induced Modulation of Cytokine Secretion from Normal and Leukemic Human Myelomonocytic Cells", Int. Arch. Allergy Immunol, 109:110-115 (1996).

Wentland, et al., "3-Quinolinecarboxamides. A Series of Novel Orally-Active Antiherpetic Agents", J. Med. Chem., 36:1580-1596 (1993).

Wilson, et al., "The Structural Basis for the Specificity of Pyridinylimidazole Inhibitors of p38 MAP Kinase", Chemistry & Biology, 4(6):423-431 (1997).

Wilson, et el., "Laser-Jet Delayed Trapping: Electron-Transfer Trapping of the Photoenol from 2-Methylbenzophenone", J. Am. Chem. Soc., 109:4743-4745 (1987).

Wolter, et al., "Copper-Catalyzed Coupling of Aryl Iodides with Aliphatic Alcohols", Organic Letters, 4(6):973-976 (2002).

Wrana, et al., "Mechanism of Activation of the TGF-B Receptor", Nature, 370:341-347 (1994).

Wu, et al., "Discovery of a Novel Family of CDK Inhibitors with the Program LIDAEUS:Structual Basis for Ligand-Induced Disordering of the Acivation Loop", Structure, 11:399-410 (2003).

Yang, et al., "Molecular Mechanism for the Regulation of Protein Kinase B/Akt by Hvdrophobic Motif Phosphorylation", Molecular Cell, 9:1227-1240 (2002).

Yang, et al., "Palladium-Catalyzed Amination of Arly Halides and Sulfonates", Journal of Organometallic Chemistry, 576:125-146 (1999).

Yarden, et al., "Human Proto-oncogene c-kit: a New Cell Surface Receptor Tyrosine Kinase for an Unidentified Ligand", The EMBO Journal, 6(11):3341-3351 (1987).

Yoneda, et al., "A New Synthesis of Purines", J.C.S. Chem. Comm., p. 551 (1974).

Yonezawa, et al., "Synthesis of Sequentially Controlled Isomeric, Wholly aromatic Polyketones Composed of 2-trifluoromethylbiphenylene and 2,2'-dimethoxybiphenylene Units", Reactive & Functional Polymers, 52:19-30 (2002).

Yoshimoto, et al., "Correlation Analysis of Baker's Studies on Enzyme Inhibition. 2. Chymotrypsin, Trypsin, Thymidine Phosphorylase, Uridine Phosphorylase, Thimidylate Synthetase, Cytosine Nucleoside Deaminase, Dihodrofolate Dehydrogenase, Glutamate Dehydrogenase, Lactate Dehydrogenase, and Glyceraldehydephosphate Reductase, Malate Dehydroqenase", Journal of Medicinal Chemistrv, 19(1):71-98 (1976).

Yoshino, et al., "Organic Phosphorous Compounds. 2. Synthesis and Coronary Vasodilator Activity of (Benzothiazolybenzyl) Phosphonate Derivatives", J. Med. Chem., 32:1528-1532 (1989).

Yu, et al., "Frequency of TPR-MET Rearrangement in Patients with Gastric Carcinoma and in First-Degree Relatives", Cancer, 88(8):1801-1806 (2000).

Zaidi, et al., "New Anti-Mycobacterial Hydantoins", Pharmazie, 35:755-756 (1980).

Zhen, et al., "Structural and Functional Domains Critical for Constitutive Activation of the HGF-Receptor (MET)", Oncoqene, 9(6):1691-1697 (1994).

Zinner, et al., "Zur Weiteren Kenntnis Bicyclischer 3.5-Dioxopyrazolidine", Die Pharmazie, 25(5):309-312 (1970).

Zustovich, F. et al., "Sorafenib plus Daily Low-dose Temozolomide for Relapsed Glioblastoma: A Phase II Study", Anticancer Research (2013), 33: pp. 3487-3494.

Zvilichovsky, et al., "Aminolysis and Polymerization of 3-(p-Toluenesulfonoxy) Hydantoin", Israel Journal of Chemistry, 7:547-554 (1969).

\* cited by examiner

| Treatment | Change from Baseline | Percentage of Patients |
|---|---|---|
| Ripretinib | Improvement and No Change | 67 |
| | Deterioration > MCID | 33 |
| Placebo | Improvement and No Change | 41 |
| | Deterioration > MCID | 59 |

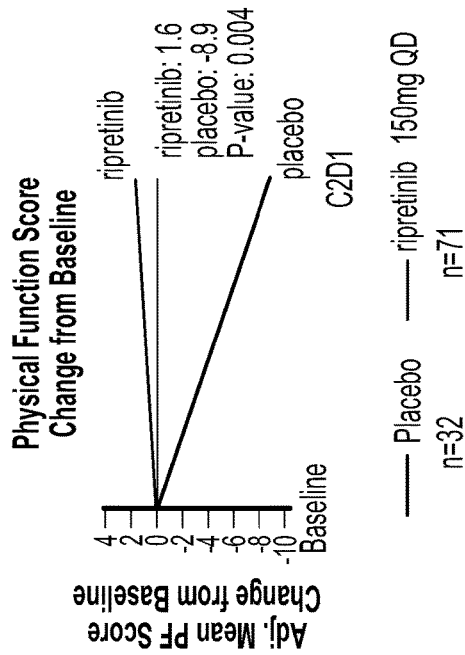
FIG. 6A
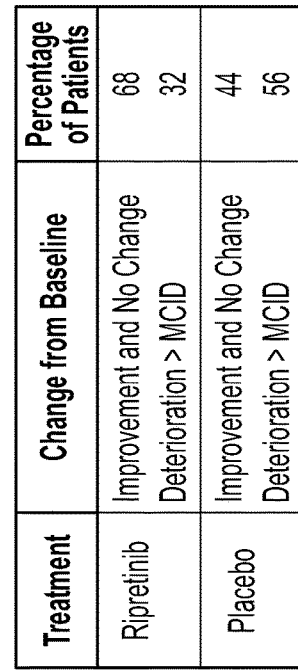
FIG. 6B
| Treatment | Change from Baseline | Percentage of Patients |
|---|---|---|
| Ripretinib | Improvement and No Change | 68 |
| | Deterioration > MCID | 32 |
| Placebo | Improvement and No Change | 44 |
| | Deterioration > MCID | 56 |
FIG. 6C

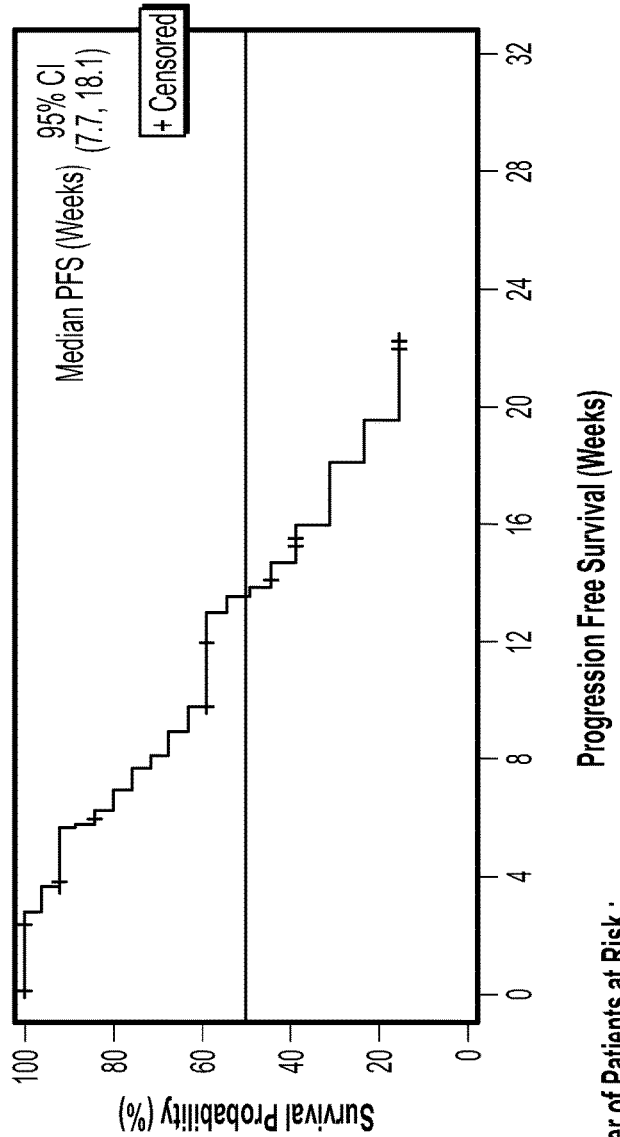

| Gene | Subj ID | Arm | PFS (Weeks) | Censored? | Mutation |
|---|---|---|---|---|---|
| Wild Type | 1 | DCC-2618 150 mg QD | 11.1429 | Yes | None |
| Wild Type | 2 | DCC-2618 150 mg QD | 52.1429 | Yes | SDHC/TP53 |
| Wild Type | 3 | DCC-2618 150 mg QD | 24.7143 | Yes | None |
| Wild Type | 4 | DCC-2618 150 mg QD | 8.7143 | No | SDHC/ATRX |
| Wild Type | 5 | DCC-2618 150 mg QD | 36.4286 | Yes | KRAS |
| Wild Type | 6 | DCC-2618 150 mg QD | 8.7143 | No | MCL1 Amplification |
| Wild Type | 7 | DCC-2618 150 mg QD | 26 | No | NF1 |
| Wild Type | 8 | Placebo | 4 | No | CDKN2A/CDKN2B/PTEN |
| Wild Type | 9 | Placebo | 36 | Yes | SDHA/TP53 |
| Wild Type | 10 | Placebo | 9 | No | NF1 |

FIG. 15

| Gene | Subj ID | Arm | PFS (Weeks) | Censored? |
|---|---|---|---|---|
| KIT Other Exons | 11 | DCC-2618 150 mg QD | 3.0 | Yes |
| KIT Other Exons | 12 | DCC-2618 150 mg QD | 12.9 | No |
| KIT Other Exons | 13 | Placebo | 3.9 | No |
| KIT Other Exons | 14 | Placebo | 7.3 | No |
| PDGFRA | 15 | DCC-2618 150 mg QD | 4.1 | No |
| PDGFRA | 16 | DCC-2618 150 mg QD | 7.6 | No |
| PDGFRA | 17 | DCC-2618 150 mg QD | 28.1 | Yes |

FIG. 20

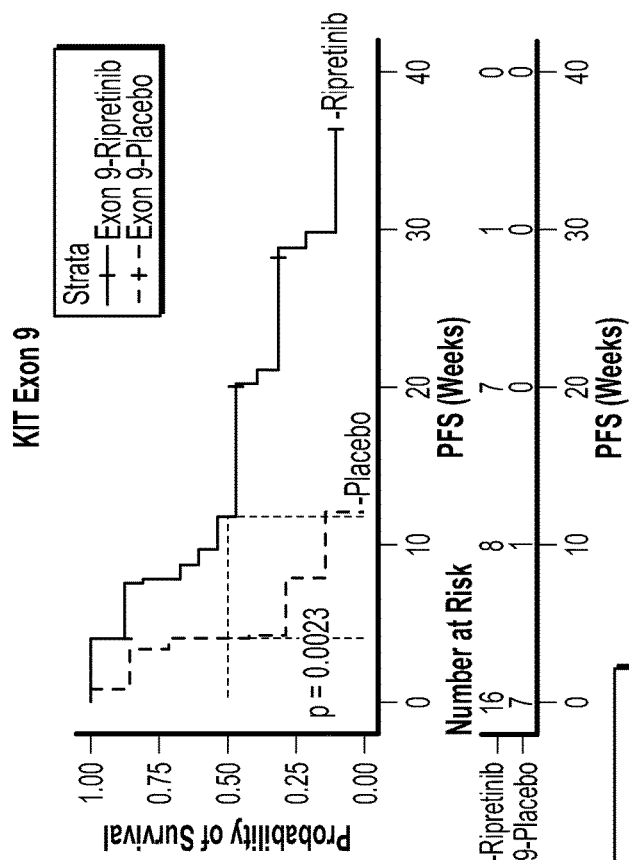
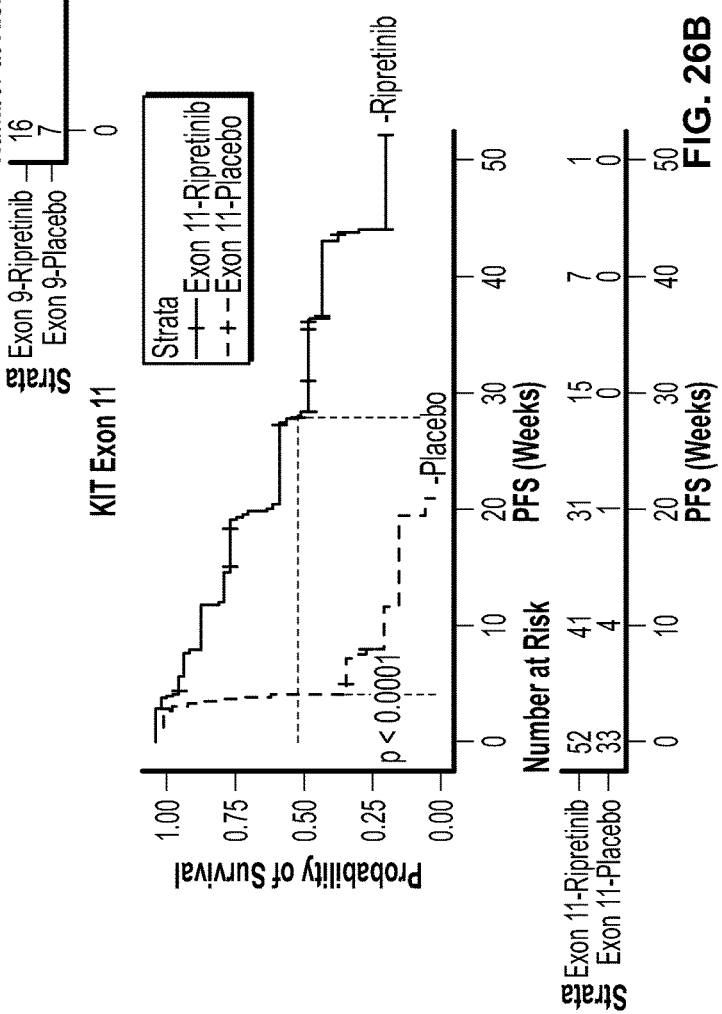
FIG. 26A
FIG. 26B

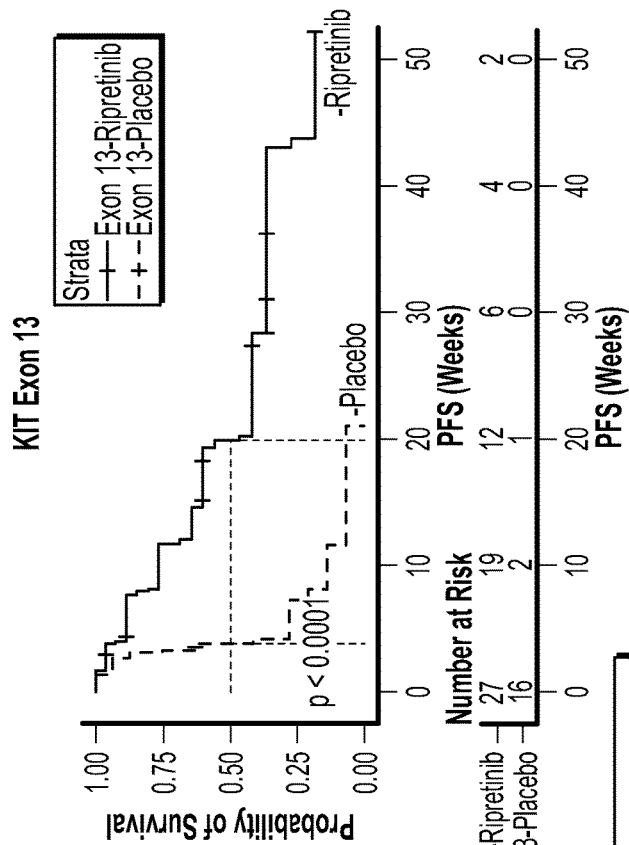
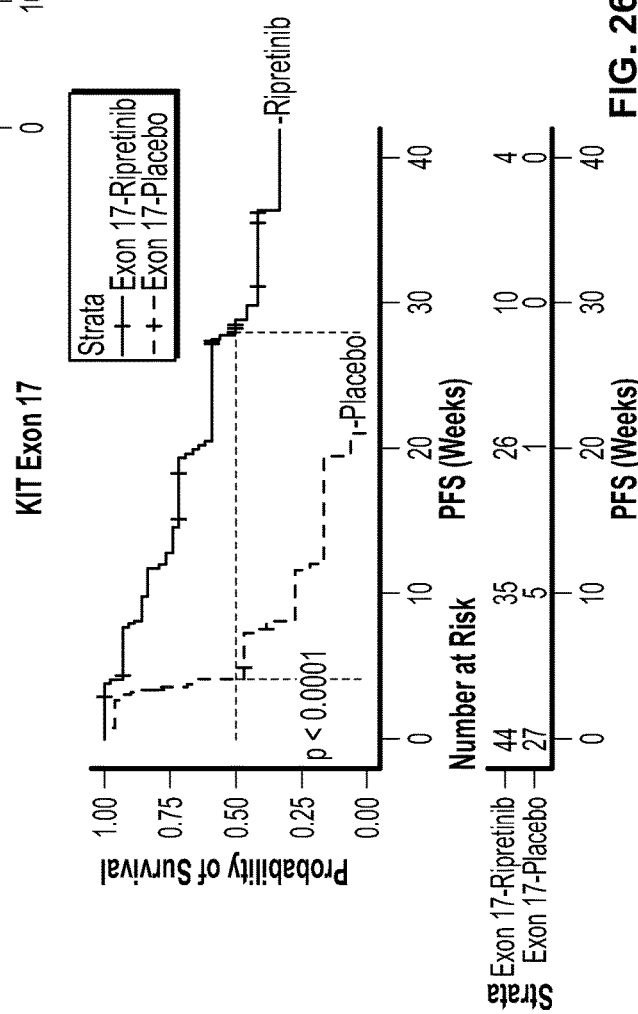
FIG. 26C
FIG. 26D

METHODS OF TREATING GASTROINTESTINAL STROMAL TUMORS

CROSS-REFERENCE TO RELATED APPLICATIONS

This application is a continuation of U.S. Ser. No. 17/180,218 filed Feb. 19, 2021, which is a divisional application of U.S. Ser. No. 17/028,640 filed Sep. 22, 2020, which is a continuation of International Application Number PCT/US2020/045876 filed Aug. 12, 2020, which claims priority to U.S. Ser. No. 62/885,797 filed Aug. 12, 2019, U.S. Ser. No. 62/904,198 filed Sep. 23, 2019, U.S. Ser. No. 62/926,281 filed Oct. 25, 2019, U.S. Ser. No. 62/936,018 filed Nov. 15, 2019, U.S. Ser. No. 62/968,927 Jan. 31, 2020, U.S. Ser. No. 62/968,945 filed Jan. 31, 2020, U.S. Ser. No. 63/023,921 filed May 13, 2020, and U.S. Ser. No. 63/023,936 filed May 13, 2020, the contents of each of which are incorporated herein by reference in their entirety.

BACKGROUND

Gastrointestinal stromal tumors (GIST) comprise less than 1% of all gastrointestinal (GI) tumors, but constitute the most common mesenchymal tumors and soft tissue sarcomas of the GI tract. They occur anywhere along the GI tract but are found most often in the stomach (60%) or small intestine (30%) and less frequently in the rectum, colon, or mesentery. In the United States, around 3300 to 6000 new cases of GIST are diagnosed each year. The vast majority of cases are sporadic, and older age is a recognized risk factor. Mutations in KIT and platelet-derived growth factor receptor-alpha (PDGFRA) are found in over 80% of all primary GISTs. Alterations in neurofibromatosis type 1 gene (NF1) and succinate dehydrogenase (SDH) complex (SDHC) genes as well as altered methylation of SDHC promoter have been described as oncogenic drivers in GIST without activating mutations in KIT or PDGFRA, and they have been linked to familial and heritable syndromes (NF1 and Carney-Stratakis syndrome).

Despite a wide variation in tumor size, location, and histologic subtypes (spindle cell, epithelioid cells, and mixed type), approximately 85% of all GISTs share oncogenic mutations in 1 of 2 receptor tyrosine kinases (TKs): KIT or PDGFRA. Constitutive activation of either of these TKs plays a central role in the oncogenic behavior of GIST. The early characterization of GIST mutational status is important in both the localized and metastatic settings to identify imatinib-resistant mutations (such as some primary KIT exon 17 mutations or PDGFRA D842V) or mutations that require a higher dose of imatinib. Patients with GIST lacking KIT or PDGFRA mutations usually do not benefit from imatinib, and standard treatment algorithms mostly do not apply. However, other mutations may be present in these patients, with the largest group represented by SDH-deficiency frequently associated with Carney or Carney-Stratakis-Syndrome. Other subtypes have mutations in NF1 (usually associated with neurofibromatosis type I) or in BRAF or KRAS. Very recently, casuistic cases of GIST-like tumors harboring NTRK translocations have further expanded the spectrum of molecular subtypes.

In the pre-tyrosine kinase inhibitor (TKI) era, GISTs (often categorized as gastric leiomyosarcomas or leiomyoblastomas) were treated within the subtype of agnostic sarcoma trials and lacked an effective systemic therapy. However, a deeper understanding of the molecular pathogenesis and driving role of the protooncogenes KIT and PDGFRA has transformed the treatment of both localized and metastatic diseases. Localized and resectable tumors are treated surgically which remains the mainstay of curative therapy for localized disease. Resected high-risk GIST is typically treated with adjuvant imatinib, whereas low-risk GIST is managed with surgery alone. Intermediate-risk GIST is managed on a per-case basis. In an advanced/metastatic setting, imatinib 400 mg daily is approved, with dose escalation to 800 mg at the time of progression, and has been shown to yield dramatic results in disease control. Imatinib-refractory patients are treated with sunitinib as a second-line therapy and regorafenib as third-line therapy on resistance or intolerance to sunitinib.

At diagnosis, a mutation in the KIT gene occurs in 80% of GISTs and is usually found in exon 11, and less commonly in exon 9. Both mechanisms cause ligand-independent receptor activation, which leads to uncontrolled cell growth and transformation. Primary mutations affect a loss-of-function mutation in the JM domain and lead to a shift in equilibrium toward a Type I active or on-state conformation of KIT and away from a Type II inactive or off-state conformation of KIT. Exon 11 primary mutations are the most commonly seen in GISTs (around 70% of cases), and derive significant benefit from treatment with imatinib in both the adjuvant and metastatic settings, achieving a 2-year relapse-free survival of ~90% in the adjuvant setting, and a median event-free survival just under 2 years in the metastatic setting. Primary mutations (in treatment-naïve patients) in exon 9 affect the extracellular domain of KIT, mimicking conformational changes induced by ligand binding and triggering KIT receptor homodimerization. This dimerization leads to the activation of specific intracellular signaling pathways which can lead to cancer cell proliferation, survival, and resistance. Although less common than exon 11 mutations, exon 9 mutations (10%-15% of newly diagnosed cases) are most commonly seen in GISTs arising from the small intestine. Unlike exon 11 mutations, they benefit less from imatinib in both the adjuvant and metastatic settings.

Despite significant improvement in outcomes compared with those in the pre-mutation-driven/TKI therapy era, response to imatinib is not experienced by all patients, and most patients with GIST will ultimately develop resistance to imatinib, most commonly due to the development of secondary mutations in KIT. Secondary resistance mutations usually arise in the catalytic domain of the kinase: 1) at the switch pocket, which typically occur in KIT exons 13 and 14 or PDGFRA exons 14 and 15 and sterically disrupt drug binding or conformationally activate KIT, and 2) in the activation loop switch encoded by KIT exons 17 and 18 and PDGFRA 18. Activation loop mutations act by shifting the kinase into an activated Type I or on-state conformation that is less amenable to drug binding by any of the approved Type II TKIs. Although uncommon in primary GIST (1%-2% of newly diagnosed cases), mutations in exons 13, 14 and 17 are often responsible for acquired imatinib resistance, with exon 17 mutations alone accounting for as many as 50% of the acquired resistance cases to imatinib, and later to sunitinib. A need exists for a TKI that can broadly inhibit clinically relevant KIT and PDGFRA mutations.

SUMMARY

Described herein are methods of treating a gastrointestinal stromal tumor in a patient in need thereof comprising administering to the patient a therapeutically effective amount of ripretinib or a pharmaceutically acceptable salt thereof.

For example, in one embodiment described herein is a method of treating a patient suffering from an advanced gastrointestinal stromal tumor, comprising orally administering to the patient 100 mg to 300 mg, e.g., 150 mg, of ripretinib daily, wherein the patient's tumor has progressed from, or the patient was intolerant to, a previous first line administration of imatinib.

For example, in one embodiment described herein is a method of treating a patient suffering from an advanced gastrointestinal stromal tumor, comprising orally administering to the patient 100 mg to 250 mg, e.g., 150 mg, of ripretinib daily, wherein the patient's tumor has progressed from, or the patient was intolerant to, a previous first line administration of imatinib.

In another embodiment, described herein is a method of treating a patient suffering from an advanced gastrointestinal stromal tumor, comprising orally administering to the patient 100 mg to 600 mg, e.g., 100 mg to 250 mg, e.g., 150 mg, of ripretinib daily, wherein the patient's tumor has progressed from, or the patient was intolerant to, a previous first line administration of imatinib.

In another embodiment, described herein is a method of treating a patient suffering from an advanced gastrointestinal stromal tumor, comprising orally administering to the patient one or more tablets comprising ripretinib, e.g., tablets each comprising 50 mg to 100 mg of ripretinib, daily, wherein the patient's tumor has progressed from, or the patient was intolerant to, a previous first line administration of imatinib. In some examples, the tablets comprise 50 mg of ripretinib. In some embodiments, the tablets comprise 75 mg of ripretinib. In some embodiments, the tablets comprise 100 mg of ripretinib.

In another embodiment, described herein is a method of treating a patient suffering from an advanced gastrointestinal stromal tumor, comprising orally administering to the patient one or more tablets comprising ripretinib, e.g., tablets each comprising 50 mg to 100 mg of ripretinib, daily, wherein the patient's tumor has progressed from, or the patient was intolerant to, a previous first line administration of imatinib, a previous second line administration of sunitinib, and a previous third line administration of regorafenib or wherein the patient has a documented intolerance to one or more of imatinib, sunitinib and/or regorafenib. In some embodiments, the tablets comprise 50 mg of ripretinib. In some example, the tablets comprise 75 mg of ripretinib. In some example, the tablets comprise 100 mg of ripretinib. In another embodiment, described herein is a method of treating a patient suffering from an advanced gastrointestinal stromal tumor, comprising orally administering to the patient 100 mg to 250 mg of ripretinib daily, e.g., 150 mg, wherein the patient's tumor has progressed from, or the patient was intolerant to, a first line administration of imatinib, a second line administration of sunitinib, and a third line administration of regorafenib or wherein the patient has a documented intolerance to one or more of imatinib, sunitinib and/or regorafenib.

In another embodiment, described herein is a method of treating a patient suffering from an advanced gastrointestinal stromal tumor, comprising orally administering to the patient 100 mg to 600 mg of ripretinib daily, e.g., 100 mg to 250 mg, e.g., 100 mg to 500 mg, e.g., 100 mg to 250 mg, e.g., 150 mg, wherein the patient's tumor has progressed from, or the patient was intolerant to, a first line administration of imatinib, a second line administration of sunitinib, and a third line administration of regorafenib or wherein the patient has a documented intolerance to one or more of imatinib, sunitinib and/or regorafenib.

In another embodiment, described herein is a method of treating a patient suffering from an advanced gastrointestinal stromal tumor, comprising orally administering to the patient to the patient, on a daily basis, one or more tablets each comprising ripretinib, e.g., tablets each comprising 50 mg to 100 mg of ripretinib, wherein the patient's tumor has progressed from, or the patient was intolerant to, a first line administration of imatinib, a second line administration of sunitinib, and a third line administration of regorafenib or wherein the patient has a documented intolerance to one or more of imatinib, sunitinib and/or regorafenib. In some embodiment, the tablets comprise 50 mg of ripretinib. In some embodiment, the tablets comprise 75 mg of ripretinib. In some embodiment, the tablets comprise 100 mg of ripretinib.

In another embodiment, described herein is a method of treating a patient suffering from an advanced gastrointestinal stromal tumor, comprising orally administering to the patient 100 mg to 600 mg of ripretinib daily, e.g., 100 mg to 250 mg, e.g., 100 mg to 500 mg, e.g., 100 mg to 250 mg, e.g., 150 mg, e.g., 300 mg, wherein the patient was previously administered at least two tyrosine kinase inhibitors before administration of the ripretinib.

In another embodiment, described herein is a method of treating a patient suffering from an advanced gastrointestinal stromal tumor, comprising orally administering to the patient 150 mg of ripretinib once daily, wherein the patient was previously administered at least two tyrosine kinase inhibitors before administration of the ripretinib.

In another embodiment, described herein is a method of treating a patient suffering from an advanced gastrointestinal stromal tumor, comprising orally administering to the patient, on a daily basis, one or more tablets each comprising ripretinib, e.g., tablets each comprising 50 mg to 100 mg of ripretinib, wherein the patient was previously administered at least two tyrosine kinase inhibitors before administration of the ripretinib. In some embodiment, the tablets comprise 50 mg of ripretinib. In some embodiment, the tablets comprise 75 mg of ripretinib. In some embodiment, the tablets comprise 100 mg of ripretinib.

In another embodiment, described herein is a method of treating a patient suffering from an advanced gastrointestinal stromal tumor, comprising orally administering to the patient 150 mg of ripretinib once daily, wherein the patient was previously administered three or more kinase inhibitors before administration of the ripretinib. In some embodiments, after at least 4 weeks of the daily ripretinib administration, the patient has at least a 5-month progression-free survival as measured using mRECIST v1.1. In some embodiments, orally administering to the patient 150 mg of ripretinib once daily comprises administering to the patient three tablets each tablet comprising 50 mg of ripretinib. In some embodiments, one of the three or more kinase inhibitors is imatinib. In some embodiments, the patient was previously administered imatinib, sunitinib and regorafenib.

In another embodiment, described herein is a method of treating a patient suffering from an advanced gastrointestinal stromal tumor, comprising orally administering to the patient 150 mg daily ripretinib, wherein the patient's tumor has progressed from, or the patient was intolerant to, a first line administration of imatinib, a second line administration of sunitinib, and a third line administration of regorafenib.

In another embodiment, described herein is a method of treating a patient suffering from an advanced gastrointestinal stromal tumor, comprising orally administering to the patient 150 mg of ripretinib once or twice daily, wherein the patient's tumor has progressed from, or the patient was intolerant to, a previous first line administration of imatinib.

In another embodiment, described herein is a method for achieving at least 5 months of progression free survival as determined by mRECIST 1.1 in a patient having an advanced gastrointestinal stromal tumor, comprising orally administering to the patient 100, 150 200, or 300 mg of ripretinib daily or twice daily for at least 28 days.

In another embodiment, described herein is a method for achieving at least 5 months of progression free survival as determined by mRECIST 1.1 in a patient having an advanced gastrointestinal stromal tumor, comprising orally administering to the patient 100, 150, or 200 mg of ripretinib daily or twice daily for at least 28 days.

In another embodiment, descried herein is a method of treating a patient suffering from Grade 3 palmer-plantar erythrodysesthesia syndrome while being administered 150 mg ripretinib daily or twice daily, comprising withholding administration of ripretinib for at least 7 days or until the patient has less than or equal to Grade 1 palmer-plantar plantar erythrodysesthesia syndrome, then administering to the patient 100 mg daily (e.g., 100 mg once daily) ripretinib for at least 28 days.

In another embodiment, descried herein is a method of treating a patient suffering from Grade 2 palmer-plantar erythrodysesthesia syndrome upon administration of 150 mg ripretinib daily or twice daily, comprising a) withholding administration of ripretinib until the patient has less than or equal to Grade 1 palmer-plantar erythrodysesthesia syndrome or baseline; b) if the patient recovers from the palmer-plantar erythrodysesthesia syndrome within 7 days of withholding administration, then administering to the patient 150 mg daily ripretinib or c) if the patient has not recovered, then administering to the patient 100 mg daily ripretinib for at least 28 days.

In another embodiment, described herein is a method of treating a gastrointestinal stromal tumor in a patient in need thereof, wherein the patient is being treated concurrently with a CYP3A4 inhibitor, the method comprising: orally administering to the patient 100 mg or 150 mg of ripretinib, or a pharmaceutically acceptable salt thereof, once or twice daily, and wherein upon administration of the ripretinib and the CYP3A4 inhibitor, provides an increased ripretinib area under the plasma concentration curve ($AUC_{0-inf}$) of 80% or more in the patient as compared to administration of ripretinib without concurrent treatment of the CYP3A4 inhibitor, and therefore the patient is at higher risk of an adverse event; and monitoring the patient more frequently, as compared to a patient not being treated with a CYP3A4 inhibitor, for the adverse event.

In another embodiment, described herein is a method of treating a gastrointestinal stromal tumor in a patient in need thereof, wherein the patient is being treated concurrently with a proton pump inhibitor, the method comprising: orally administering to the patient 100 mg or 150 mg of ripretinib, or a pharmaceutically acceptable salt thereof, once or twice daily, and wherein administration of the ripretinib and proton pump inhibitor to the patient provides no clinically significant difference in the plasma exposure of ripretinib in the patient as compared to administration of ripretinib without concurrent treatment of the proton pump inhibitor.

In another embodiment, described herein is a method of treating a gastrointestinal stromal tumor in a patient in need thereof, the method comprising orally administering to the patient 100 mg or 150 mg of ripretinib, or a pharmaceutically acceptable salt thereof, once or twice daily, wherein the ripretinib is administered to the patient with food or without food.

BRIEF DESCRIPTION OF THE DRAWINGS

FIG. 6A, FIG. 6B, and FIG. 6C depict EORTC QLQ-C30 physical function questions (FIG. 6A) and patient score changes (FIG. 6B) from baseline in response and corresponding patient percentage distributions (FIG. 6C) used in the study of Example 2 at 150 mg ripretinib QD. Physical function scores improved on average 1.6 from baseline to C2D1 among patients taking ripretinib in contrast to placebo patients who saw on average, a decline from baseline to C2D1 of 8.9 (p=0.004). In this study, 71 patients were receiving ripretinib and 32 were receiving placebo.

FIG. 14A and FIG. 14B depict progression free survival (PFS) studies in the double-blind and open-label periods in the study of Example 2 for patients who dose escalated from 150 mg ripretinib QD 150 mg ripretinib BID. FIG. 14C depicting median PFS data and other parameters in these PFS studies.

FIG. 15 shows exemplary PFS data among patients with wild-type KIT mutations in the study of Example 2.

FIG. 20 shows exemplary progression free survival data for patients with other KIT mutations and PGDFR mutations in the study of Example 2 at 150 mg ripretinib QD.

FIG. 26A-D depicts an exemplary comparison of PFS of patient subgroups with Exon 9 (FIG. 26A), Exon 11 (FIG. 26B), Exon 13 (FIG. 26C), or Exon 17 (FIG. 26D) KIT mutations. This exemplary data show that ripretinib showed PFS benefit in all assessed patient subgroups compared to placebo.

DETAILED DESCRIPTION

Figure 1:
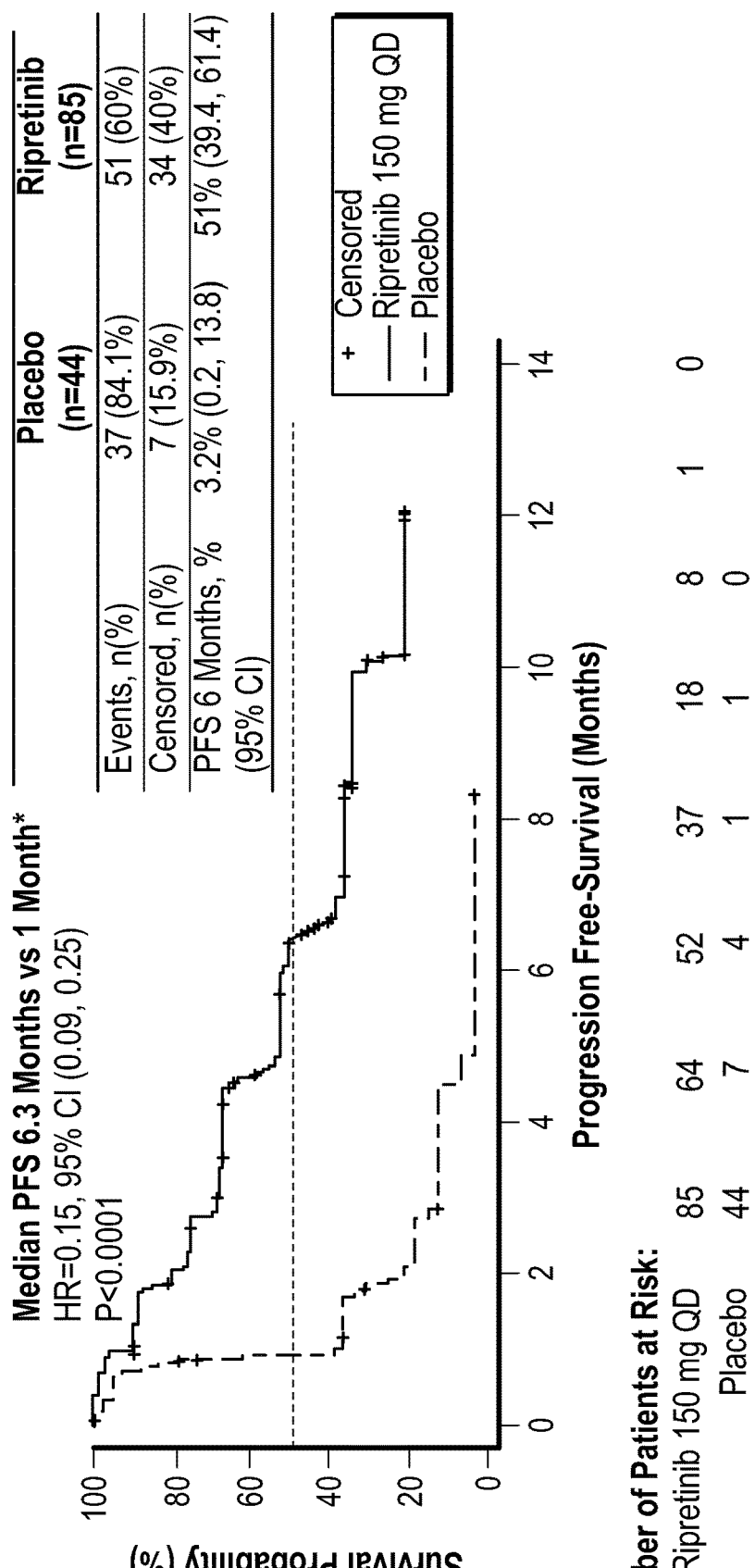
FIG. 1 depicts a plot of survival probability with respect to progression-free survival (PFS) for patients on ripretinib and patients on placebo as described in Example 2.

The features and other details of the disclosure will now be more particularly described. Certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

As used herein, "ripretinib" is a compound represented by the following structure:

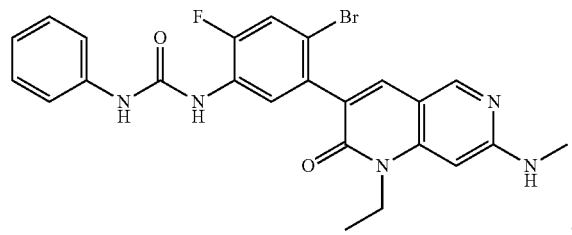

As used herein, "sunitinib" is a compound represented by the following structure:

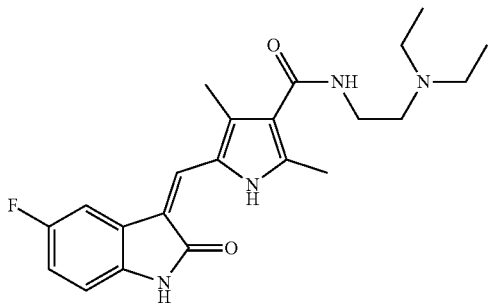 [SMILES: CCN(CC)CCNC(=O)c1c(C)[nH]c(/C=C2\C(=O)Nc3ccc(F)cc32)c1C]

As used herein, "imatinib" is a compound represented by the following structure:

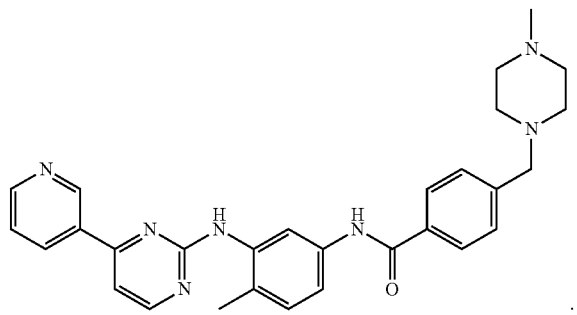 [SMILES: Cc1ccc(NC(=O)c2ccc(CN3CCN(C)CC3)cc2)cc1Nc1nccc(-c2cccnc2)n1]

As used herein, "regorafenib" is a compound represented by the following structure:

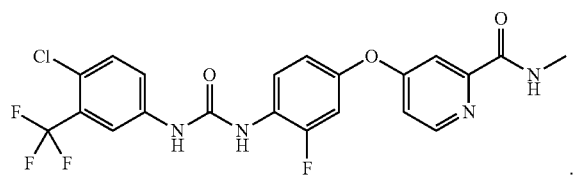 [SMILES: CNC(=O)c1cc(Oc2ccc(NC(=O)Nc3ccc(Cl)c(C(F)(F)F)c3)c(F)c2)ccn1]

As used herein, "Compound A" is a compound represented by the following structure:

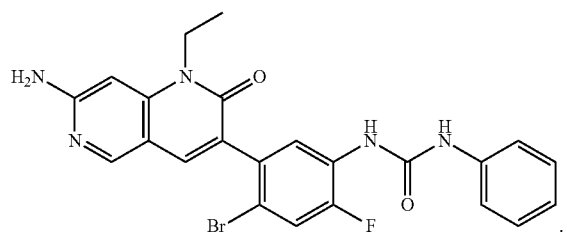 [SMILES: CCn1c(=O)c(-c2cc(NC(=O)Nc3ccccc3)c(F)cc2Br)cc2cnc(N)cc21]

"Individual," "patient," or "subject" are used interchangeably herein and include any animal, including mammals, including mice, rats, other rodents, rabbits, dogs, cats, swine, cattle, sheep, horses, or primates, and humans. The compounds described herein can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods described herein is desirably a mammal in which treatment of a disorder described herein is desired, such as a human.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts.

As used herein, "treating" includes any effect, e.g., lessening, reducing, modulating, or eliminating, that results in the improvement of the condition, disease, disorder and the like.

Therapeutically effective amount" includes the amount of the subject compound that will elicit the biological or medical response of a tissue, system, animal or human that is being sought by the researcher, veterinarian, medical doctor or other clinician. A compound described herein, e.g., ripretinib is administered in therapeutically effective amounts to treat a condition described herein, e.g., gastrointestinal stromal tumors. Alternatively, a therapeutically effective amount of a compound is the quantity required to achieve a desired therapeutic and/or prophylactic effect, such as an amount which results in the prevention of or a decrease in the symptoms associated with the condition.

As used herein, "$AUC_{0-24\ h}$" refers to the area under the plasma concentration-time curve from time zero to 24 hours for a compound described herein. As used herein, "$AUC_{0-inf}$" refers to the area under the plasma concentration-time curve from time zero to infinite time for a compound described herein. As used herein, "$C_{max}$" refers to the maximum plasma concentration of a compound described herein.

A compound described herein, e.g., ripretinib, can be formulated as a pharmaceutical composition using a pharmaceutically acceptable carrier and administered by a variety of routes. In some embodiments, such compositions are for oral administration. In some embodiments, compositions formulated for oral administration are provided as tablets. In some embodiments, such compositions are for parenteral (by injection) administration (e.g., a composition formulated for local injection at the site of a tumor, e.g., a diffuse-type giant cell tumor). In some embodiments, such compositions are for transdermal administration. In some embodiments, such compositions are for topical administration. In some embodiments, such compositions are for intravenous (IV) administration. In some embodiments, such compositions are for intramuscular (IM) administration. Such pharmaceutical compositions and processes for preparing them are well known in the art. See, e.g., REMINGTON: THE SCIENCE AND PRACTICE OF PHARMACY (A. Gennaro, et al., eds., 19th ed., Mack Publishing Co., 1995).

Methods of Treatment

Described herein are methods of treating gastrointestinal stromal tumors in a patient in need thereof. For example, the present disclosure relates to a method of treating a patient suffering from an advanced gastrointestinal stromal tumor, comprising orally administering to the patient 100 mg or more of ripretinib daily, e.g., 100 mg to 5000 mg, e.g., 100 mg to 500 mg, 100 mg to 250 mg, e.g., 150 mg, wherein the patient's tumor has progressed from, or the patient was intolerant to, a previous first line administration of imatinib. In some embodiments, the method comprises administering to the patient 110 mg of ripretinib daily. In some embodiments, the method comprises administering to the patient 120 mg of ripretinib daily. In some embodiments, the method comprises administering to the patient 130 mg of ripretinib daily. In some embodiments, the method comprises administering to the patient 140 mg of ripretinib daily. In some embodiments, the method comprises administering to the patient 150 mg of ripretinib daily. In some embodiments, the method comprises administering to the patient 200 mg of ripretinib daily. In some embodiments, the method comprises administering to the patient 250 mg of ripretinib daily. In some embodiments, the method comprises administering to the patient 300 mg of ripretinib daily. In some embodiments, the method comprises administering to the patient 350 mg of ripretinib daily. In some embodiments, the method comprises administering to the patient 400 mg of ripretinib daily. In some embodiments, the method comprises administering to the patient 450 mg of ripretinib daily. In some embodiments, the method comprises administering to the patient 500 mg of ripretinib daily. In some embodiments, the method comprises administering to the patient 550 mg of ripretinib daily. In some embodiments, the method comprises administering to the patient 600 mg of ripretinib daily. In some embodiments, the method comprises administering to the patient 650 mg of ripretinib daily. In some embodiments, the method comprises administering to the patient 700 mg of ripretinib daily. In some embodiments, the method comprises administering to the patient 750 mg of ripretinib daily. In some embodiments, the method comprises administering to the patient 800 mg of ripretinib daily. In some embodiments, the method comprises administering to the patient 850 mg of ripretinib daily. In some embodiments, the method comprises administering to the patient 900 mg of ripretinib daily. In some embodiments, the method comprises administering to the patient 950 mg of ripretinib daily. In some embodiments, the method comprises administering to the patient 1000 mg of ripretinib daily. In some embodiments, the method comprises administering to the patient 150 mg of ripretinib once daily. In some embodiments, the method comprises administering to the patient 200 mg of ripretinib once daily. In some embodiments, the method comprises administering to the patient 250 mg of ripretinib once daily. In some embodiments, the method comprises administering to the patient 300 mg of ripretinib once daily. In some embodiments, the method comprises administering to the patient 350 mg of ripretinib once daily. In some embodiments, the method comprises administering to the patient 400 mg of ripretinib once daily. In some embodiments, the method comprises administering to the patient 450 mg of ripretinib daily. In some embodiments, the method comprises administering to the patient 500 mg of ripretinib once daily. In some embodiments, the method comprises administering to the patient 550 mg of ripretinib once daily. In some embodiments, the method comprises administering to the patient 600 mg of ripretinib once daily. In some embodiments, the method comprises administering to the patient 650 mg of ripretinib once daily. In some embodiments, the method comprises administering to the patient 700 mg of ripretinib once daily. In some embodiments, the method comprises administering to the patient 750 mg of ripretinib once daily. In some embodiments, the method comprises administering to the patient 800 mg of ripretinib once daily. In some embodiments, the method comprises administering to the patient 850 mg of ripretinib once daily. In some embodiments, the method comprises administering to the patient 900 mg of ripretinib once daily. In some embodiments, the method comprises administering to the patient 950 mg of ripretinib once daily. In some embodiments, the method comprises administering to the patient 1000 mg of ripretinib once daily. In some embodiments, the method comprises administering to the patient 150 mg of ripretinib twice daily. In some embodiments, the method comprises administering to the patient 200 mg of ripretinib twice daily. In some embodiments, the method comprises administering to the patient 250 mg of ripretinib twice daily. In some embodiments, the method comprises administering to the patient 300 mg of ripretinib twice daily. In some embodiments, the method comprises administering to the patient 350 mg of ripretinib twice daily. In some embodiments, the method comprises administering to the patient 400 mg of ripretinib twice daily. In some embodiments, the method comprises administering to the patient 450 mg of ripretinib twice daily. In some embodiments, the method comprises administering to the patient 500 mg of ripretinib twice daily.

In some embodiments, a patient was only previously treated with a first line administration of imatinib, e.g., only imatinib and no other therapeutic compounds had been administered to the patient before administration of ripretinib to the patient. For example, a patient was not previously administered with sunitinib and/or regorafenib, e.g., the patient was not previously given a second line administration of sunitinib therapy and/or a third-line administration of regorafenib therapy.

In some embodiments, the patient has a non-nodal tumor lesion of greater than or equal to 1.0 cm in the long axis or greater than or equal to double the slide thickness in the long axis, within 21 days prior to the first dose of ripretinib. Contemplated methods of treatment include administering ripretinib on a 42-day cycle, comprising daily administrations of ripretinib without administering sunitinib. After at least one 42-day cycle comprising daily administrations of ripretinib, the patient may have progression-free survival as measured using mRECIST v1.1. In some embodiments, the patient treated with daily administrations of ripretinib may have significant progression free survival (e.g., about 3 months progression free survival or more, e.g., about 6 months progression free survival, as compared to a second line daily administration of 50 mg sunitinib for four weeks followed by two weeks without daily administrations on a 42-day cycle, wherein the patient's tumor has progressed from, or the patient was intolerant to, the previous first line administration of imatinib.

Contemplated treatments with ripretinib may treat a broad spectrum of KIT and PDGFRA mutations. For example, a patient's tumor may have a KIT exon 9 mutation, a PDGFRA exon 18 mutation, a PDGFRA exon 12 mutation or a PDGFRA exon 18 activation loop mutation. For example, the patient's tumor mutation is a PDGFRA D842V mutation.

In some embodiments, a patient's tumor has an imatinib resistant mutation selected from the group consisting of a KIT exon 17 activation loop mutation, a KIT exon 18 activation loop mutation, a KIT exon 13 mutation, a KIT exon 14 mutation, a KIT exon 18 mutation, a PDGFRA exon 12 mutation, a PDGFRA exon 14 mutation, a PDGRFA exon 15 mutation, and a PDGFRA exon 18 activation loop mutation. For example, the imatinib resistant mutation is a PDGFRA D842V mutation.

In some embodiments, the patient's tumor has an imatinib resistant mutation selected from the group consisting of KIT exon 13 or 14 mutation, PDGFRA exon 14 or 15 mutation, a KIT 17 or 18 activation loop mutation, and a PDGFRA 18 activation loop mutation. For example, the patient's tumor has an imatinib resistant KIT exon 17 mutation.

Also described herein is a method of treating a patient suffering from an advanced gastrointestinal stromal tumor, comprising orally administering to the patient 100 mg or more, e.g., up to about 600 mg, e.g. up to about 250 mg, e.g., 100 mg or 150 mg, of ripretinib daily, wherein the patient's tumor has progressed from, or the patient was intolerant to, a first line administration of imatinib, a second line administration of sunitinib, and a third line administration of regorafenib or wherein the patient has a documented intolerance to one or more of imatinib, sunitinib and/or regorafenib. Contemplated methods of treatment include orally administering 100 mg, 150 mg or more of ripretinib daily without administering sunitinib on a 42-day cycle. In some embodiments, the method comprises administering to the patient 110 mg of ripretinib daily. In some embodiments, the method comprises administering to the patient 120 mg of ripretinib daily. In some embodiments, the method comprises administering to the patient 130 mg of ripretinib daily. In some embodiments, the method comprises administering to the patient 140 mg of ripretinib daily. In some embodiments, the method comprises administering to the patient 150 mg of ripretinib daily. In some embodiments, the method comprises administering to the patient 200 mg of ripretinib daily. In some embodiments, the method comprises administering to the patient 250 mg of ripretinib daily. In some embodiments, the method comprises administering to the patient 300 mg of ripretinib daily. In some embodiments, the method comprises administering to the patient 350 mg of ripretinib daily. In some embodiments, the method comprises administering to the patient 400 mg of ripretinib daily. In some embodiments, the method comprises administering to the patient 450 mg of ripretinib daily. In some embodiments, the method comprises administering to the patient 500 mg of ripretinib daily. In some embodiments, the method comprises administering to the patient 550 mg of ripretinib daily. In some embodiments, the method comprises administering to the patient 600 mg of ripretinib daily. In some embodiments, the method comprises administering to the patient 650 mg of ripretinib daily. In some embodiments, the method comprises administering to the patient 700 mg of ripretinib daily. In some embodiments, the method comprises administering to the patient 750 mg of ripretinib daily. In some embodiments, the method comprises administering to the patient 800 mg of ripretinib daily. In some embodiments, the method comprises administering to the patient 850 mg of ripretinib daily. In some embodiments, the method comprises administering to the patient 900 mg of ripretinib daily. In some embodiments, the method comprises administering to the patient 950 mg of ripretinib daily. In some embodiments, the method comprises administering to the patient 1000 mg of ripretinib daily. In some embodiments, the method comprises administering to the patient 150 mg of ripretinib once daily. In some embodiments, the method comprises administering to the patient 200 mg of ripretinib once daily. In some embodiments, the method comprises administering to the patient 250 mg of ripretinib once daily. In some embodiments, the method comprises administering to the patient 300 mg of ripretinib once daily. In some embodiments, the method comprises administering to the patient 350 mg of ripretinib once daily. In some embodiments, the method comprises administering to the patient 400 mg of ripretinib once daily. In some embodiments, the method comprises administering to the patient 450 mg of ripretinib daily. In some embodiments, the method comprises administering to the patient 500 mg of ripretinib once daily. In some embodiments, the method comprises administering to the patient 550 mg of ripretinib once daily. In some embodiments, the method comprises administering to the patient 600 mg of ripretinib once daily. In some embodiments, the method comprises administering to the patient 650 mg of ripretinib once daily. In some embodiments, the method comprises administering to the patient 700 mg of ripretinib once daily. In some embodiments, the method comprises administering to the patient 750 mg of ripretinib once daily. In some embodiments, the method comprises administering to the patient 800 mg of ripretinib once daily. In some embodiments, the method comprises administering to the patient 850 mg of ripretinib once daily. In some embodiments, the method comprises administering to the patient 900 mg of ripretinib once daily. In some embodiments, the method comprises administering to the patient 950 mg of ripretinib once daily. In some embodiments, the method comprises administering to the patient 1000 mg of ripretinib once daily. In some embodiments, the method comprises administering to the patient 150 mg of ripretinib twice daily. In some embodiments, the method comprises administering to the patient 200 mg of ripretinib twice daily. In some embodiments, the method comprises administering to the patient 250 mg of ripretinib twice daily. In some embodiments, the method comprises administering to the patient 300 mg of ripretinib twice daily. In some embodiments, the method comprises administering to the patient 350 mg of ripretinib twice daily. In some embodiments, the method comprises administering to the patient 400 mg of ripretinib twice daily. In some embodiments, the method comprises administering to the patient 450 mg of ripretinib twice daily. In some embodiments, the method comprises administering to the patient 500 mg of ripretinib twice daily.

In some embodiments, a method of treating a patient suffering from an advanced gastrointestinal stromal tumor, comprising orally administering to the patient 100 mg or more of ripretinib daily, e.g., up to about 600 mg, e.g., 100 mg to 250 mg, e.g., 100 mg to 500 mg, e.g., 100 mg to 250 mg, e.g., 150 mg, wherein the patient was previously administered at least two tyrosine kinase inhibitors, is contemplated. Contemplated methods of treatment include orally administering 100 mg, 150 mg or more of ripretinib daily without administering sunitinib on a 42-day cycle. In some embodiments, the method comprises administering to the patient 110 mg of ripretinib daily. In some embodiments, the method comprises administering to the patient 120 mg of ripretinib daily. In some embodiments, the method comprises administering to the patient 130 mg of ripretinib daily. In some embodiments, the method comprises administering to the patient 140 mg of ripretinib daily. In some embodiments, the method comprises administering to the patient 150 mg of ripretinib daily. In some embodiments, the method comprises administering to the patient 200 mg of ripretinib daily. In some embodiments, the method comprises administering to the patient 250 mg of ripretinib daily. In some embodiments, the method comprises administering to the patient 300 mg of ripretinib daily. In some embodiments, the method comprises administering to the patient 350 mg of ripretinib daily. In some embodiments, the method comprises administering to the patient 400 mg of ripretinib daily. In some embodiments, the method comprises administering to the patient 450 mg of ripretinib daily. In some embodiments, the method comprises administering to the patient 500 mg of ripretinib daily. In some embodiments, the method comprises administering to the patient 550 mg of ripretinib daily. In some embodiments, the method comprises administering to the patient 600 mg of ripretinib daily. In some embodiments, the method comprises administering to the patient 650 mg of ripretinib daily. In some embodiments, the method comprises administering to the patient 700 mg of ripretinib daily. In some embodiments, the method comprises administering to the patient 750 mg of ripretinib daily. In some embodiments, the method comprises administering to the patient 800 mg of ripretinib daily. In some embodiments, the method comprises administering to the patient 850 mg of ripretinib daily. In some embodiments, the method comprises administering to the patient 900 mg of ripretinib daily. In some embodiments, the method comprises administering to the patient 950 mg of ripretinib daily. In some embodiments, the method comprises administering to the patient 1000 mg of ripretinib daily. In some embodiments, the method comprises administering to the patient 100 mg of ripretinib once daily. In some embodiments, the method comprises administering to the patient 150 mg of ripretinib once daily. In some embodiments, the method comprises administering to the patient 200 mg of ripretinib once daily. In some embodiments, the method comprises administering to the patient 250 mg of ripretinib once daily. In some embodiments, the method comprises administering to the patient 300 mg of ripretinib once daily. In some embodiments, the method comprises administering to the patient 350 mg of ripretinib once daily. In some embodiments, the method comprises administering to the patient 400 mg of ripretinib once daily. In some embodiments, the method comprises administering to the patient 450 mg of ripretinib daily. In some embodiments, the method comprises administering to the patient 500 mg of ripretinib once daily. In some embodiments, the method comprises administering to the patient 550 mg of ripretinib once daily. In some embodiments, the method comprises administering to the patient 600 mg of ripretinib once daily. In some embodiments, the method comprises administering to the patient 650 mg of ripretinib once daily. In some embodiments, the method comprises administering to the patient 700 mg of ripretinib once daily. In some embodiments, the method comprises administering to the patient 750 mg of ripretinib once daily. In some embodiments, the method comprises administering to the patient 800 mg of ripretinib once daily. In some embodiments, the method comprises administering to the patient 850 mg of ripretinib once daily. In some embodiments, the method comprises administering to the patient 900 mg of ripretinib once daily. In some embodiments, the method comprises administering to the patient 950 mg of ripretinib once daily. In some embodiments, the method comprises administering to the patient 1000 mg of ripretinib once daily. In some embodiments, the method comprises administering to the patient 150 mg of ripretinib twice daily. In some embodiments, the method comprises administering to the patient 200 mg of ripretinib twice daily. In some embodiments, the method comprises administering to the patient 250 mg of ripretinib twice daily. In some embodiments, the method comprises administering to the patient 300 mg of ripretinib twice daily. In some embodiments, the method comprises administering to the patient 350 mg of ripretinib twice daily. In some embodiments, the method comprises administering to the patient 400 mg of ripretinib twice daily. In some embodiments, the method comprises administering to the patient 450 mg of ripretinib twice daily. In some embodiments, the method comprises administering to the patient 500 mg of ripretinib twice daily. In some embodiments, the patient has previously been administered two separate tyrosine kinase inhibitors, each selected from the group consisting of imatinib, sunitinib, regorafenib, lapatinib, gefitinib, erlotinib, vatalanib, crenolanib, and pharmaceutically acceptable salts thereof. In some embodiments, each of the tyrosine kinase inhibitors is independently selected from the group consisting of imatinib, sunitinib, and regorafenib. In some embodiments, each of the tyrosine kinase inhibitors is independently selected from the group consisting of imatinib mesylate, sunitinib malate, and regorafenib.

In some embodiments of the methods described herein, the patient is orally administered one or more tablets comprising ripretinib. For example, the disclosed methods include a method of treating a patient suffering from an advanced gastrointestinal stromal tumor, comprising orally administering to the patient one or more tablets comprising ripretinib, e.g., tablets each comprising 50 mg to 100 mg of ripretinib, daily, wherein the patient's tumor has progressed from, or the patient was intolerant to, a previous first line administration of imatinib. In some embodiments, the patient is administered one tablet comprising ripretinib. In some embodiments, the patient is administered one tablet comprising 50 mg of ripretinib. In some embodiments, the patient is administered one tablet comprising 50 mg of ripretinib once daily. In some embodiments, the patient is administered two tablets each comprising 50 mg of ripretinib. In some embodiments, the patient is administered two tablets each comprising 50 mg of ripretinib once daily. In some embodiments, the patient is administered three tablets each comprising 50 mg of ripretinib. In some embodiments, the patient is administered three tablets each comprising 50 mg of ripretinib once daily. In some embodiments, the patient is administered four tablets each comprising 50 mg of ripretinib. In some embodiments, the patient is administered four tablets each comprising 50 mg of ripretinib once daily. In some embodiments, the patient is administered five tablets each comprising 50 mg of ripretinib. In some embodiments, the patient is administered five tablets each comprising 50 mg of ripretinib once daily. In some embodiments, the patient is administered six tablets each comprising 50 mg of ripretinib. In some embodiments, the patient is administered six tablets each comprising 50 mg of ripretinib once daily.

Additionally, the disclosed methods include a method of treating a patient suffering from an advanced gastrointestinal stromal tumor, comprising orally administering to the patient, on a daily basis, one or more tablets each comprising ripretinib, e.g., tablets each comprising 50 mg to 100 mg of ripretinib, wherein the patient's tumor has progressed from, or the patient was intolerant to, a first line administration of imatinib, a second line administration of sunitinib, and a third line administration of regorafenib or wherein the patient has a documented intolerance to one or more of imatinib, sunitinib and/or regorafenib. In some embodiments, the patient is administered one tablet comprising ripretinib. In some embodiments, the patient is administered one tablet comprising 50 mg of ripretinib. In some embodiments, the patient is administered one tablet comprising 50 mg of ripretinib once daily. In some embodiments, the patient is administered two tablets each comprising 50 mg of ripretinib. In some embodiments, the patient is administered, once daily, two tablets each comprising 50 mg of ripretinib. In some embodiments, the patient is administered three tablets each comprising 50 mg of ripretinib. In some embodiments, the patient is administered, once daily, three tablets each comprising 50 mg of ripretinib once daily.

In some embodiments, provided is a method of treating a patient suffering from an advanced gastrointestinal stromal tumor, comprising orally administering to the patient, on a daily basis, one or more tablets each comprising ripretinib, e.g., tablets each comprising 50 mg to 100 mg of ripretinib, wherein the patient was previously administered at least two tyrosine kinase inhibitors before administration of the ripretinib. In some embodiments, the patient is administered one tablet comprising ripretinib. In some embodiments, the patient is administered one tablet comprising 50 mg of ripretinib. In some embodiments, the patient is administered one tablet comprising 50 mg of ripretinib once daily. In some embodiments, the patient is administered two tablets each comprising 50 mg of ripretinib. In some embodiments, the patient is administered, once daily, two tablets each comprising 50 mg of ripretinib. In some embodiments, the patient is administered three tablets each comprising 50 mg of ripretinib. In some embodiments, the patient is administered, once daily, three tablets each comprising 50 mg of ripretinib. In some embodiments, the patient has previously been administered two separate tyrosine kinase inhibitors, each selected from the group consisting of imatinib, sunitinib, regorafenib, lapatinib, gefitinib, erlotinib, vatalanib, crenolanib, and pharmaceutically acceptable salts thereof. In some embodiments, each of the tyrosine kinase inhibitors is independently selected from the group consisting of imatinib, sunitinib, and regorafenib. In some embodiments, each of the tyrosine kinase inhibitors is independently selected from the group consisting of imatinib mesylate, sunitinib malate, and regorafenib.

In another embodiment, described herein is a method of treating a patient suffering from an advanced gastrointestinal stromal tumor, comprising orally administering to the patient 150 mg of ripretinib once daily, wherein the patient was previously administered three or more kinase inhibitors before administration of the ripretinib. In some embodiments, after at least 4 weeks of the daily ripretinib administration, the patient has at least a 5-month progression-free survival as measured using mRECIST v1.1. In some embodiments, orally administering to the patient 150 mg of ripretinib once daily comprises administering to the patient three tablets each tablet comprising 50 mg of ripretinib. In some embodiments, one of the three or more kinase inhibitors is imatinib. In some embodiments, the patient was previously administered imatinib, sunitinib and regorafenib.

In some embodiments, if the patient suffers from a Grade 3 palmer-plantar erythrodysesthesia syndrome upon administration of the ripretinib, the method further comprises a) withholding administration of ripretinib for at least 7 days or until the patient has less than or equal to Grade 1 palmer-plantar erythrodysesthesia syndrome, then administering to the patient 100 mg daily (e.g., 100 mg once daily) ripretinib for at least 28 days.

In some embodiments, if the patient suffers from a Grade 2 palmer-plantar erythrodysesthesia syndrome upon administration of the ripretinib, the method further comprises: a) withholding administration of ripretinib until the patient has less than or equal to Grade 1 palmer-plantar erythrodysesthesia syndrome or baseline; b) if the patient recovers from the palmer-plantar erythrodysesthesia syndrome within 7 days of withholding administration, then administering to the patient 150 mg daily ripretinib or c) if the patient has not recovered, then administering to the patient 100 mg daily ripretinib for at least 28 days.

In another embodiment, described herein is a method of treating a patient suffering from an advanced gastrointestinal stromal tumor, comprising orally administering to the patient 150 mg daily ripretinib, wherein the patient's tumor has progressed from, or the patient was intolerant to, a first line administration of imatinib, a second line administration of sunitinib, and a third line administration of regorafenib.

In some embodiments, if the patient suffers from a Grade 3 palmer-plantar erythrodysesthesia syndrome upon administration of the ripretinib, the method further comprises a) withholding administration of ripretinib for at least 7 days or until the patient has less than or equal to Grade 1 palmer-plantar erythrodysesthesia syndrome, then administering to the patient 100 mg daily (e.g., 100 mg once daily) ripretinib for at least 28 days.

In some embodiments, if the patient suffers from a Grade 2 palmer-plantar erythrodysesthesia syndrome upon administration of the ripretinib, the method further comprises: a) withholding administration of ripretinib until the patient has less than or equal to Grade 1 palmer-plantar erythrodysesthesia syndrome or baseline; b) if the patient recovers from the palmer-plantar erythrodysesthesia syndrome within 7 days of withholding administration, then administering to the patient 150 mg daily ripretinib or c) if the patient has not recovered, then administering to the patient 100 mg daily ripretinib for at least 28 days.

In another embodiment, described herein is a method of treating a patient suffering from an advanced gastrointestinal stromal tumor, comprising orally administering to the patient 150 mg of ripretinib once or twice daily, wherein the patient's tumor has progressed from, or the patient was intolerant to, a previous first line administration of imatinib. In some embodiments, if the patient suffers from Grade 3 palmer-plantar erythrodysesthesia syndrome upon administration of the ripretinib, the method further comprises a) withholding administration of ripretinib for at least 7 days or until the patient has less than or equal to Grade 1 palmer-plantar erythrodysesthesia syndrome, then administering to the patient 100 mg daily (e.g., 100 mg once daily) ripretinib for at least 28 days. In some embodiments, if the patient suffers from Grade 3 palmer-plantar erythrodysesthesia syndrome upon administration of the ripretinib, the method further comprises a) withholding administration of ripretinib for at least 7 days or until the patient has less than or equal to Grade 1 palmer-plantar erythrodysesthesia syndrome, then administering to the patient 100 mg daily (e.g., 100 mg once daily) ripretinib for at least 28 days. In some embodiments, if the patient suffers from Grade 2 palmer-plantar erythrodysesthesia syndrome upon administration of the ripretinib, the method further comprises: a) withholding administration of ripretinib until the patient has less than or equal to Grade 1 palmer-plantar erythrodysesthesia syndrome or baseline; b) if the patient recovers from the palmer-plantar erythrodysesthesia syndrome within 7 days of withholding administration, then administering to the patient 150 mg daily ripretinib or c) if the patient has not recovered, then administering to the patient 100 mg daily ripretinib for at least 28 days. In some embodiments, if the patient suffers from a Grade 3 adverse disorder selected from arthralgia or myalgia upon administration of the ripretinib, the method further comprises: a) withholding administration of ripretinib until the patient has less than or equal to Grade 1 adverse disorder, then administering to the patient 100 mg daily (e.g., 100 mg once daily) ripretinib for at least 28 days.

In some embodiments, if the patient suffers from Grade 3 hypertension upon administration of the ripretinib, the method further comprises withholding administration of ripretinib until the patient's blood pressure is controlled, and if the patient has less than or equal to Grade 1 blood pressure is, administering to the patient 150 mg daily ripretinib, or if the patient has more than Grade 1 blood pressure, administering 100 mg daily (e.g., 100 mg once daily) ripretinib.

In another embodiment, described herein is a method for achieving at least 5 months of progression free survival as determined by mRECIST 1.1 in a patient having an advanced gastrointestinal stromal tumor, comprising orally administering to the patient 100, 150 200, or 300 mg of ripretinib daily or twice daily for at least 28 days. In some embodiments, the patient has been administered at least one previous kinase inhibitor. In some embodiments, the patient has been administered at least three previous kinase inhibitors. In some embodiments, the at least one previous kinase inhibitor is imatinib. In some embodiments, comprising orally administering to the patient 100, 150 or 200 mg of ripretinib daily or twice daily for at least 4 months.

In another embodiment, described herein is a method for achieving at least 5 months of progression free survival as determined by mRECIST 1.1 in a patient having an advanced gastrointestinal stromal tumor, comprising orally administering to the patient 100, 150, or 200 mg of ripretinib daily or twice daily for at least 28 days. In some embodiments, the patient has been administered at least one previous kinase inhibitor. In some embodiments, the patient has been administered at least three previous kinase inhibitors. In some embodiments, the at least one previous kinase inhibitor is imatinib. In some embodiments, comprising orally administering to the patient 100, 150, or 200 mg of ripretinib daily or twice daily for at least 4 months.

In another embodiment, descried herein is a method of treating a patient suffering from Grade 3 palmer-plantar erythrodysesthesia syndrome while being administered 150 mg ripretinib daily or twice daily, comprising withholding administration of ripretinib for at least 7 days or until the patient has less than or equal to Grade 1 palmer-plantar erythrodysesthesia syndrome, then administering to the patient 100 mg daily (e.g., 100 mg once daily) ripretinib for at least 28 days.

In another embodiment, descried herein is a method of treating a patient suffering from Grade 2 palmer-plantar erythrodysesthesia syndrome upon administration of 150 mg ripretinib daily or twice daily, comprising a) withholding administration of ripretinib until the patient has less than or equal to Grade 1 palmer-plantar erythrodysesthesia syndrome or baseline; b) if the patient recovers from the palmer-plantar erythrodysesthesia syndrome within 7 days of withholding administration, then administering to the patient 150 mg daily ripretinib or c) if the patient has not recovered, then administering to the patient 100 mg daily ripretinib for at least 28 days.

In another embodiment, described herein is a method of treating a gastrointestinal stromal tumor in a patient in need thereof, wherein the patient is being treated concurrently with a CYP3A4 inhibitor, the method comprising: orally administering to the patient 100 mg or 150 mg of ripretinib, or a pharmaceutically acceptable salt thereof, once or twice daily, and wherein upon administration of the ripretinib and the CYP3A4 inhibitor, provides an increased ripretinib area under the plasma concentration curve ($AUC_{0-inf}$) of 80% or more in the patient as compared to administration of ripretinib without concurrent treatment of the CYP3A4 inhibitor, and therefore the patient is at higher risk of an adverse event; and monitoring the patient more frequently, as compared to a patient not being treated with a CYP3A4 inhibitor, for the adverse event. In some embodiments, if the patient suffers from a Grade 3 palmer-plantar erythrodysesthesia syndrome adverse event, the method further comprises a) withholding administration of ripretinib for at least 7 days or until the patient has less than or equal to Grade 1 palmer-plantar erythrodysesthesia syndrome, then administering to the patient 100 mg daily ripretinib for at least 28 days. In some embodiments, if the patient suffers from Grade 2 palmer-plantar erythrodysesthesia syndrome upon administration of the ripretinib, the method further comprises: a) withholding administration of ripretinib until the patient has less than or equal to Grade 1 palmer-plantar erythrodysesthesia syndrome or baseline; b) if the patient recovers from the palmer-plantar erythrodysesthesia syndrome within 7 days of withholding administration, then administering to the patient 150 mg daily ripretinib or c) if the patient has not recovered, then administering to the patient 100 mg daily ripretinib for at least 28 days. In some embodiments, the CYP3A4 inhibitor is selected from the group consisting of itraconazole, ketoconazole, clarithromycin, and indinavir. In some embodiments, the CYP3A4 inhibitor is itraconazole. In some embodiments, the patient has previously been administered one or more tyrosine kinase inhibitors, each selected from the group consisting of imatinib, sunitinib, regorafenib, lapatinib, gefitinib, erlotinib, vatalanib, crenolanib, and pharmaceutically acceptable salts thereof.

In another embodiment, described herein is a method of treating a gastrointestinal stromal tumor in a patient in need thereof, wherein the patient is being treated concurrently with a proton pump inhibitor, the method comprising: orally administering to the patient 100 mg or 150 mg of ripretinib, or a pharmaceutically acceptable salt thereof, once or twice daily, and wherein administration of the ripretinib and proton pump inhibitor to the patient provides no clinically significant difference in the plasma exposure of ripretinib in the patient as compared to administration of ripretinib without concurrent treatment of the proton pump inhibitor. In some embodiments, the proton pump inhibitor is selected from the group consisting of pantoprazole, omeprazole, lansoprazole, rabeprazole, esomeprazole, and dexlansoprazole. In some embodiments, the proton pump inhibitor is pantoprazole. In some embodiments, the patient is being treated concurrently with 40 mg of the proton pump inhibitor once daily.

In another embodiment, described herein is a method of treating a gastrointestinal stromal tumor in a patient in need thereof, the method comprising orally administering to the patient 100 mg or 150 mg of ripretinib, or a pharmaceutically acceptable salt thereof, once or twice daily, wherein the ripretinib is administered to the patient with food or without food. In some embodiments, the food comprises a high-fat meal (e.g., a high-fat meal described herein).

In some embodiments, the therapeutic efficacy of ripretinib is determined by the progression-free survival of the patient after independent radiologic review using Response Evaluation Criteria in Solid Tumors (RECIST). In some embodiments, the therapeutic efficacy of ripretinib is determined by the progression-free survival of the patient after independent radiologic review using modified Response Evaluation Criteria in Solid Tumors (mRECIST). In some embodiments, the therapeutic efficacy of ripretinib is determined by the Objective Response Rate (ORR), Time to Tumor Progression (TTP) or Overall Survival (OS) of the patient after independent radiologic review using mRECIST. In some embodiments, the therapeutic efficacy of ripretinib is determined by the progression-free survival of the patient based on investigator assessment. In some embodiments, the therapeutic efficacy of ripretinib is determined by the quality of life of the patient in accordance with European Organisation for Research and Treatment of Cancer Quality of Life Questionnaire for Cancer 30-item (EORTC-QLQ-C30) and the EuroQol 5-Dimension 5-Level (EQ-5D-5L) questionnaires. In some embodiments, the therapeutic efficacy of ripretinib is determined by the disease control rate of the patient. In some embodiments, the therapeutic efficacy of ripretinib is determined by the duration of response of the patient.

After at least one month, two months, e.g., 42 days or more of treatment with ripretinib, the patient may have a progression-free survival as measured using mRECIST v1.1. As another example, the patient may have a least a 5 or 6 month progression-free survival as compared to placebo after at least 4 weeks of daily administration of ripretinib, and/or for example, after 4 weeks of daily administration of ripretinib, significantly reduced the risk of disease progression or death by 85%.

In some embodiments, the patient has at least one measurable tumor lesion according to modified RECIST Version 1.1 within 21 days prior to the first dose of ripretinib. In some embodiments, the patient has a non-nodal tumor lesion of greater than or equal to 1.0 cm in the long axis or greater than or equal to double the slide thickness in the long axis, within 21 days prior to the first dose of ripretinib.

In some embodiments, the patient's tumor has a KIT exon 9 mutation, a PDGFRA exon 18 mutation, a PDGFRA exon 12 mutation or a PDGFRA exon 18 activation loop mutation. For example, the patient's tumor mutation is a PDGFRA D842V mutation.

In some embodiments, the patient's tumor has an imatinib resistant, sunitinib resistant, and/or regorafenib resistant mutation selected from the group consisting of a KIT exon 17 activation loop mutation, a KIT exon 18 activation loop mutation, a KIT exon 13 mutation, a KIT exon 14 mutation, a KIT exon 18 mutation, a PDGFRA exon 12 mutation, a PDGFRA exon 14 mutation, a PDGRFA exon 15 mutation, and a PDGFRA exon 18 activation loop mutation. For example, the resistant mutation is a PDGFRA D842V mutation.

In some embodiments, the patient's tumor has a drug resistant mutation selected from the group consisting of KIT exon 13 or 14 mutation, PDGFRA exon 14 or 15 mutation, a KIT 17 or 18 activation loop mutation, and a PDGFRA 18 activation loop mutation. For example, the tumor has a drug resistant KIT exon 17 mutation.

Dose Modifications

Dose modifications may be made in the methods of administering ripretinib described herein as a result of adverse events experienced by the patient. In some embodiments, the dose modification is a dose interruption. In some embodiments, the dose modification is a permanent discontinuation in dosing. In some embodiments, the dose modification is a dose reduction. In some embodiments, the dose of ripretinib administered to the patient is reduced from 150 mg once daily, e.g., three tablets each comprising 50 mg of ripretinib, to 100 mg once daily, e.g., two tablets each comprising 50 mg of ripretinib. In some embodiments, the dose of ripretinib administered to the patient is reduced from 150 mg once daily, e.g., three tablets each comprising 50 mg of ripretinib, to 50 mg once daily, e.g., one tablet comprising 50 mg of ripretinib. In some embodiments, the adverse reaction is selected from the group consisting of a hand-foot skin reaction (e.g., palmar-plantar erythrodysesthesia syndrome), hypertension, arthralgia, and myalgia.

In some embodiments, the adverse event is graded in accordance with the National Cancer Institute Common Terminology Criteria for Adverse Events, version 4.03 (e.g., baseline, Grade 1, Grade 2, Grade 3, or Grade 4). In some embodiments, the dose modification is a dose interruption (e.g., a dose interruption of at least 7 days) as a result of a Grade 2 adverse event. In some embodiments, dosing resumes at the same dose level before the dose interruption if the adverse event is lowered to Grade 1 or baseline within a first time period (e.g., within 7 days). In some embodiments, dosing resumes at a reduced dose level before the dose interruption if the adverse event is lowered to Grade 1 or baseline after a first time period (e.g., after 7 days). In some embodiments, the reduced dose level is re-escalated to the dose level prior to the dose interruption if the adverse event is lowered to Grade 1 or baseline after a first time period but is maintained as a Grade 1 or baseline adverse event after a second time period (e.g., after 28 days). In some embodiments, the dose modification is a dose interruption (e.g., a dose interruption of at least 7 days up to a maximum of 28 days) as a result of a Grade 3 adverse event. In some embodiments, dosing is continued at a reduced level after the dose interruption. In some embodiments, the dose modification is a permanent discontinuation in dosing as a result of a Grade 4 adverse event (e.g., Grade 4 hypertension).

A patient can be administered an additional treatment in response to an adverse event or to prevent an adverse event from occurring. In some embodiments, a patient suffering from an adverse dermatologic reaction, e.g., a hand-foot skin reaction, e.g., palmar-plantar erythrodysesthesia syndrome, is administered a topical composition (e.g., an emollient) to treat the adverse dermatologic reaction. In some embodiments, the patient is administered the topical composition (e.g., an emollient) based on the severity of the adverse dermatologic reaction, e.g., a Grade 2, Grade 3 adverse dermatologic reaction, e.g., a Grade 1, Grade 2, or Grade 3 hand-foot skin reaction, e.g., a Grade 1, Grade 2 or Grade 3 palmar-plantar erythrodysesthesia syndrome. In some embodiments, the topical composition (e.g., an emollient) is administered to the patient during a dose interruption of ripretinib. In some embodiments, the topical composition (e.g., an emollient) is administered to the patient contemporaneously with a dose of ripretinib, e.g., a reduced dose of ripretinib.

A patient can also be administered an additional treatment prior to, or during administration of ripretinib in accordance with the methods described herein to prevent or ameliorate an adverse event. In some embodiments, the patient is administered a topical composition (e.g., an emollient) before and/or during ripretinib administration to prevent or ameliorate the onset of an adverse dermatologic reaction, e.g., a hand-foot skin reaction, e.g., palmar-plantar erythrodysesthesia syndrome.

EXAMPLES

Example 1

An Open-Label, Randomized Study to Compare the Efficacy of Ripretinib Versus Sunitinib in Patients with Advanced GIST with Prior Imatinib Therapy Study Design. Approximately 358 eligible patients will be randomized into two cohorts in a 1:1 ratio in which one cohort undergoes continuous 42-day cycles of receiving ripretinib dosed at 150 mg daily (179 patients) and the other cohort receives sunitinib dosed at 50 mg daily for 4 weeks and then 2 weeks off on 42-day cycles (179 patients).

Given the mutation-driven natural history of GIST and the well-described relationship between secondary mutations and emergence of resistance to first- and second-line TKIs, the results of this study will evaluate ripretinib compared with sunitinib as second-line therapy in patients with GIST following imatinib therapy.

The primary end point of the study is to assess the progression-free survival (PFS) of ripretinib by blinded independent central review (BICR) using modified Response Evaluation Criteria in Solid Tumors version 1.1 (mRECIST v1.1). The key secondary efficacy end points include the assessment of ORR by BICR using mRECIST v1.1 and OS.

Statistical Analysis. PFS is defined as the time from randomization to the date of the first documented progression of disease or death due to any cause and is based on BICR assessment of the primary end point. OS is defined as the time from randomization to the date of death due to any cause. OS and PFS with 95% CI will be summarized using Kaplan-Meier methodology; point estimates of hazard ratios will be obtained from a Cox regression model. Objective response is defined as a CR or PR by BICR assessment using mRECIST v1.1.

Example 2

A Randomized, Double-Blind, Placebo-Controlled, International, Multicenter Study to Evaluate the Safety, Tolerability, and Efficacy of Ripretinib Compared to Placebo in Patients with Advanced GIST Whose Previous Therapies Have Included Imatinib, Sunitinib, and Regorafenib This study was a randomized (2:1), double-blind, placebo-controlled, international, multicenter study to evaluate the safety, tolerability, and efficacy of ripretinib compared to placebo in 129 patients with advanced GIST whose previous therapies have included at least imatinib, sunitinib, and regorafenib. Patients were randomized 2:1 to either 150 mg of ripretinib or placebo once daily. The primary efficacy endpoint is progression-free survival (PFS) as determined by independent radiologic review using modified Response Evaluation Criteria in Solid Tumors (RECIST). Secondary endpoints as determined by independent radiologic review using modified RECIST include Objective Response Rate (ORR), Time to Tumor Progression (TTP) and Overall Survival (OS).

Results. This study achieved its primary endpoint of improved PFS as determined by blinded independent central radiologic review using modified Response Evaluation Criteria in Solid Tumors (RECIST) version 1.1.

Ripretinib demonstrated a median PFS of 6.3 months (27.6 weeks) compared to 1.0 month (4.1 weeks) in the placebo arm and significantly reduced the risk of disease progression or death by 85% (HR of 0.15, p<0.0001) compared to placebo. PFS rates at 6 months were 51% (95% CI: 39.4, 61.4) for ripretinib and 3.2% (95% CI: 0.2, 13.8) for placebo. Plots of survival probability with respect to PFS for patients on ripretinib and patients on placebo are shown in FIG. 1.

Figure 2:
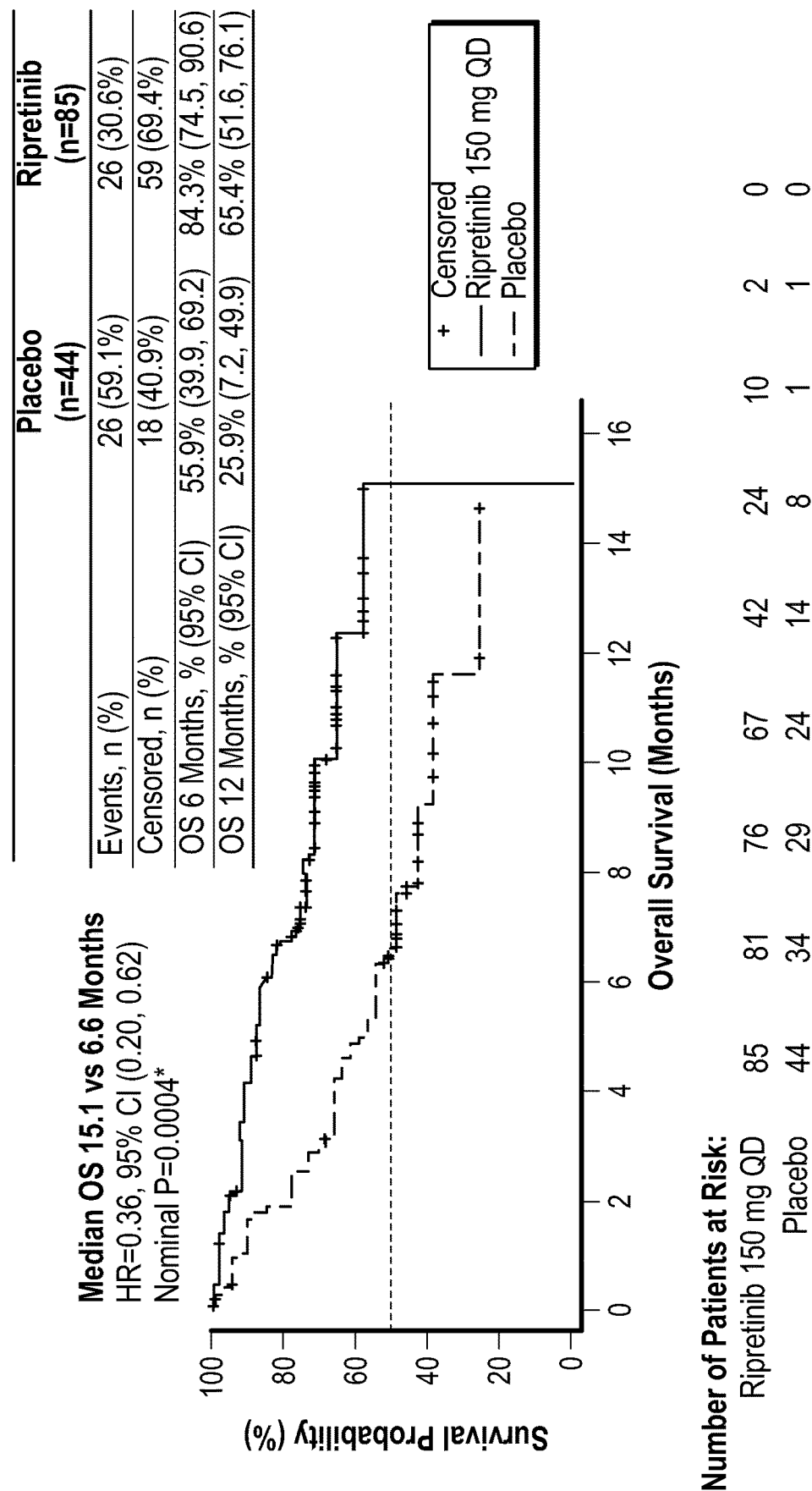
FIG. 2 depicts a plot of survival probability with respect to overall survival (OS) for patients on ripretinib and patients on placebo as described in Example 2.
Figure 3:
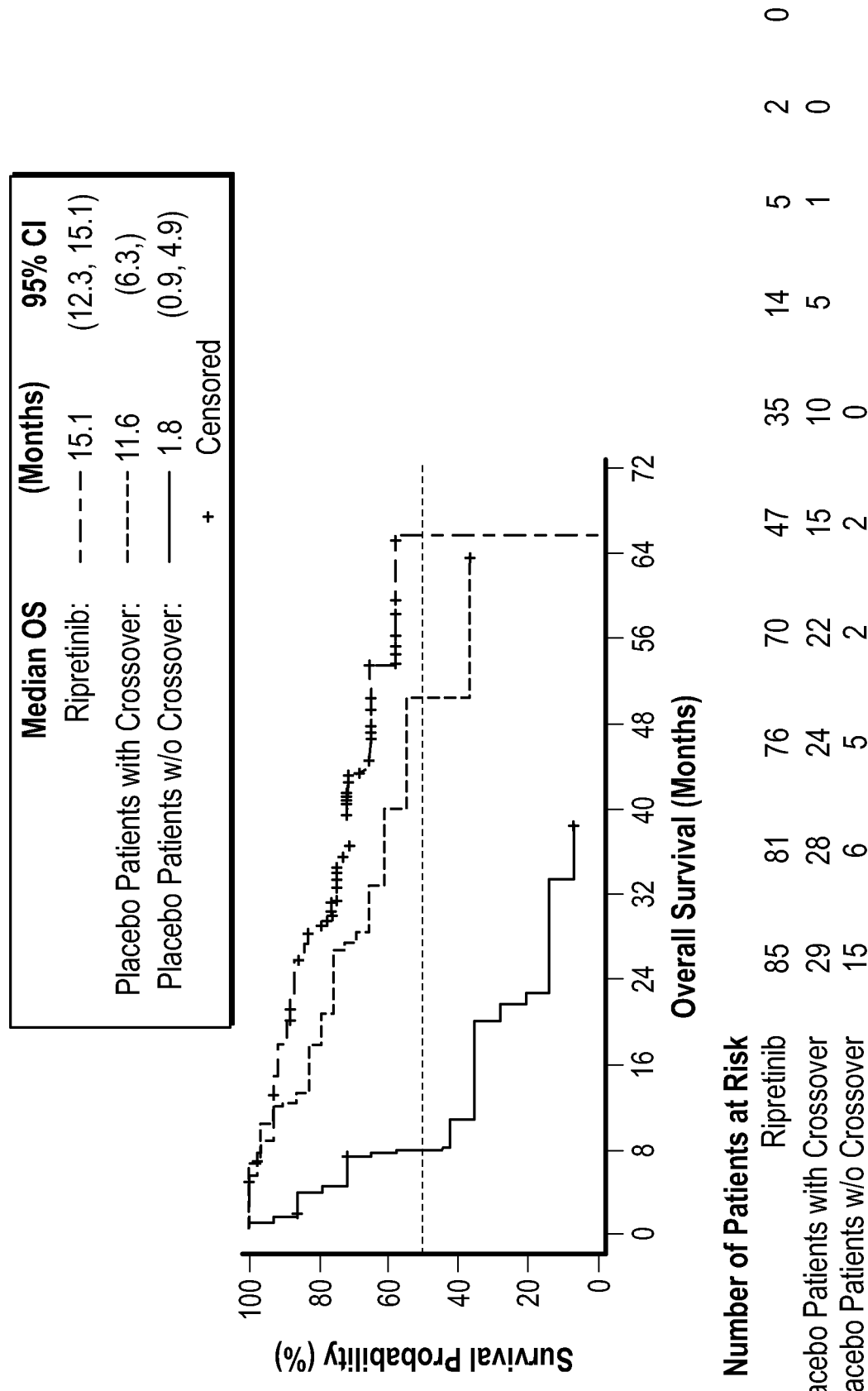
FIG. 3 depicts plots illustrating survival probability with respect to OS in patients on ripretinib, crossed over from placebo to ripretinib, and patients without cross-over.
Figure 13:
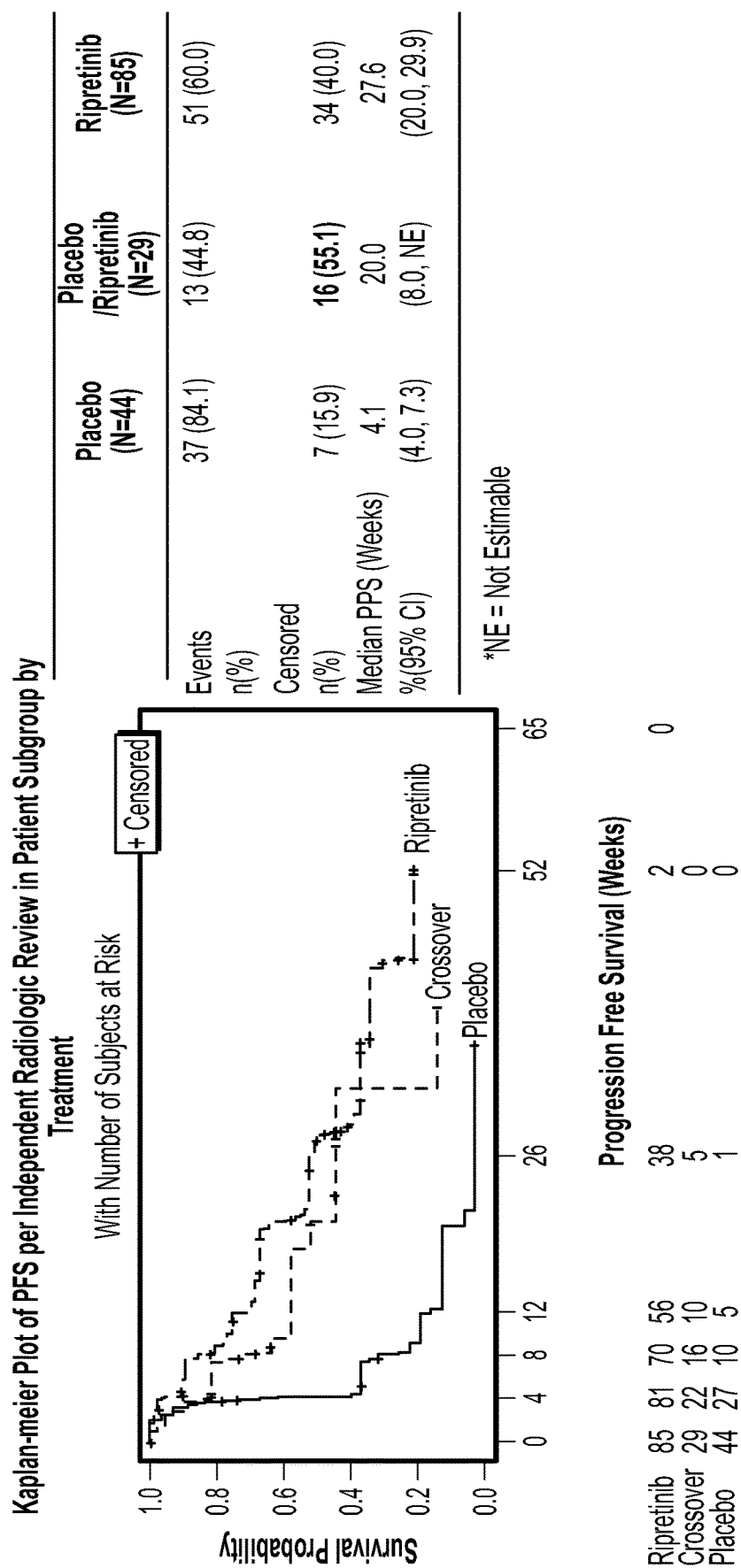
FIG. 13 depicts exemplary PFS data for patients who crossed over from placebo to ripretinib in the study described in Example 2 at 150 mg ripretinib QD.

For the key secondary endpoint of objective response rate (ORR), as determined by blinded independent central radiologic review using modified RECIST version 1.1, ripretinib demonstrated an ORR of 9.4% compared with 0% for placebo (p-value=0.0504), which was not statistically significant. Ripretinib in this study also showed a clinically meaningful improvement over placebo in terms of the secondary endpoint overall survival (OS) (median OS 15.1 months vs. 6.6 months, HR=0.36, nominal p-value=0.0004; OS rates at 12 months were 65.4% (95% CI: 51.6, 76.1) for ripretinib and 25.9% (95% CI: 7.2, 49.9) for placebo); however, because statistical significance was not achieved for ORR, the hypothesis testing of OS was not formally performed. Plots of survival probability with respect to OS of patients on ripretinib and patients on placebo are shown in FIG. 2. According to the pre-specified hierarchical testing procedure of the endpoints, the hypothesis testing of OS cannot be formally conducted unless the test of ORR is statistically significant. The OS data for the placebo arm includes patients taking placebo who, following progression, were crossed-over to ripretinib treatment. Plots illustrating survival probability with respect to OS in patients on ripretinib, crossed over from placebo to ripretinib, and patients without cross-over are shown in FIG. 3. Plots and additional data illustrating survival probability with respect to PFS in patients on ripretinib, crossed over from placebo to ripretinib, and patients without cross-over are shown in FIG. 13. Additionally, more patients receiving ripretinib had stable disease (SD) for 12 weeks (40 [47·1%] vs 2 [4·5%], respectively) and less PD (16 [18·8%] vs 28 [63·6%], respectively) than patients on placebo. The large percentage of patients receiving ripretinib with stable disease (SD) is notable as the absence of progression is considered an important marker of therapeutic benefit in GIST. Unlike many other advanced solid tumors, the absence of progression (whether a partial response (PR) or SD) is predictive of PFS and OS benefit in patients with advanced GIST.

Patients that successfully crossed over from placebo had smaller tumors vs those that did not crossover (median sum of longest diameter of target lesions 119.4 mm vs 183.3 mm). In addition, the median age of those who crossed over was higher than those who did not cross over (68.0 vs 58.0 years) and none had a baseline Eastern Cooperative Oncology Group (ECOG) score of 2, while 3 patients in the group that did not cross over had an ECOG score of 2. Patients that crossed over had a median PFS of 20.0 weeks [95% CI, 8.0–NE] vs 27.6 weeks seen in the initial ripretinib arm and 4.1 weeks seen in the initial placebo arm, respectively. Median OS in patients who crossed over was 11.6 months, vs. 15.1 months in patients initially randomized to ripretinib and 1.8 months in patients on placebo who did not crossover. TEAEs during the crossover period suggest no safety concerns when compared to the safety profile of patients initially assigned to ripretinib.

Ripretinib was generally well tolerated and the adverse event results were consistent with data from previously presented Phase 1 study results. Grade 3 or 4 treatment-emergent adverse events (TEAEs) occurred in 42 (49%) patients on the ripretinib arm compared to 19 (44%) on the placebo arm. Grade 3 or 4 TEAEs>5% of patients in the ripretinib arm were anemia (9%; n=8), abdominal pain (7%; n=6) and hypertension (7%; n=6). Grade 3 or 4 TEAEs>5% of patients in the placebo arm were anemia (14%; n=6). Table 1 lists TEAEs>15% in the ripretinib arm compared to placebo.

TABLE 1

Treatment-emergent adverse events for patients administered with either ripretinib or placebo.

| Treatment Emergent Adverse Event | Placebo (N = 43)[1] | Ripretinib 150 mg Daily (N = 85)[1] |
|---|---|---|
| Any event | 42 (98%) | 84 (99%) |
| Alopecia | 2 (5%) | 44 (52%) |
| Fatigue | 10 (23%) | 36 (42%) |
| Nausea | 5 (12%) | 33 (39%) |
| Abdominal pain | 13 (30%) | 31 (36%) |
| Constipation | 8 (19%) | 29 (34%) |
| Myalgia | 5 (12%) | 27 (32%) |
| Diarrhea | 6 (14%) | 24 (28%) |
| Decreased appetite | 9 (21%) | 23 (27%) |
| Palmar-plantar erythrodysesthesia syndrome | 0 | 18 (21%) |
| Vomiting | 3 (7%) | 18 (21%) |
| Headache | 2 (5%) | 16 (19%) |
| Weight decreased | 5 (12%) | 16 (19%) |
| Arthralgia | 2 (5%) | 15 (18%) |
| Blood bilirubin increased | 0 | 14 (16%) |
| Oedema peripheral | 3 (7%) | 14 (16%) |
| Muscle spasms | 2 (5%) | 13 (15%) |

In table 1, (1) indicates that the safety population includes 128 patients. One patient was randomized to placebo but did not receive study drug.

Patient Reported Outcomes

Patient reported outcomes were assessed by EQ-5D-5L, which provides a visual analogue scale (VAS), and EORTC QLQ-C30, which provides physical function and role function scales. The EQ-5D-5L VAS (or EQ-VAS) records the respondent's overall current health on a vertical visual analogue scale and provides a quantitative measure of the patient's perception of overall health. These patient outcomes were reported across 28-day cycles of receiving 150 mg QD ripretinib or placebo.

Figures 5A, 5B, 5C:
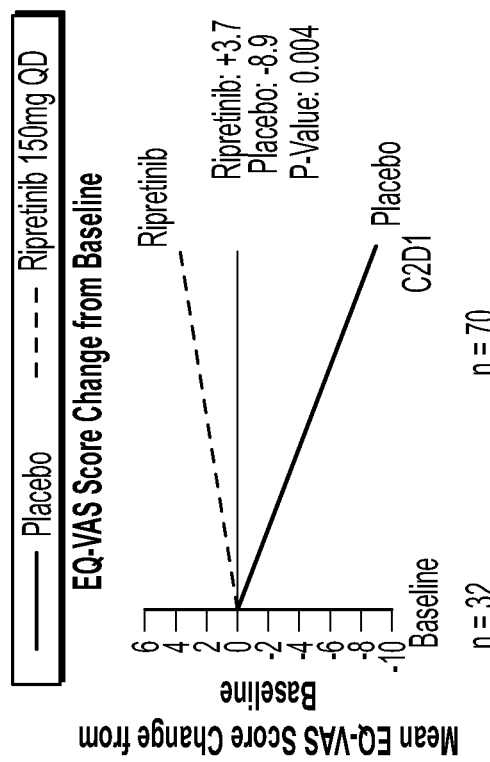
FIG. 5A, FIG. 5B, and FIG. 5C depict patient report outcome by EQ-VAS visual scale (FIG. 5A) and score changes from baseline (FIG. 5B) used to assess these scores and corresponding patient percentage distributions (FIG. 5C) used in the study of Example 2 at 150 mg ripretinib QD. In the study, 70 patients were receiving ripretinib and 32 were receiving placebo.

FIG. 5A, FIG. 5B, and FIG. 5C depict patient report outcome by EQ-VAS showing the visual scale used to assess scores (FIG. 5A), score changes from baseline (FIG. 5B) and corresponding patient percentage distributions (FIG. 5C). The EQ-VAS score improved on average 3.7 from baseline to Cycle 2, Day 1 (C2D1) among patients taking ripretinib in contrast to placebo patients who saw on average, a decline from baseline to C2D1 of 8.9 (p=0.004). 70 patients were receiving ripretinib and 32 were receiving placebo.

The EORTC QLQ-C30 is an assessment of function and symptoms of therapy by cancer patient, and is not specific to any cancer. The EORTC QLQ-C30 is a 30-question plus one global health status, including 5 functional scales, 3 symptom scales and a global health status.

FIG. 6A, FIG. 6B, and FIG. 6C depict EORTC QLQ-C30 physical function questions (FIG. 6A), patient score changes from baseline in response (FIG. 6B) and corresponding patient percentage distributions (FIG. 6C). Physical function scores improved on average 1.6 from baseline to C2D1 among patients taking ripretinib in contrast to placebo patients who saw on average, a decline from baseline to C2D1 of 8.9 (p=0.004). 71 patients were receiving ripretinib and 32 were receiving placebo.

Figures 7A, 7B, 7C:
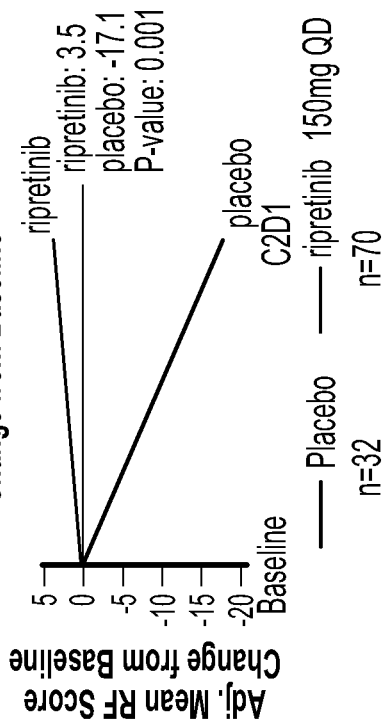
FIG. 7A, FIG. 7B, and FIG. 7C depict EORTC QLQ-C30 role function questions (FIG. 7A) and patient score changes (FIG. 7B) from baseline in response and corresponding patient percentage distributions (FIG. 7C) used in the study of Example 2 at 150 mg ripretinib QD. In the study, 70 patients were receiving ripretinib and 32 were receiving placebo.

FIG. 7A, FIG. 7B, and FIG. 7C depict EORTC QLQ-C30 role function questions (FIG. 7A) and patient score changes from baseline in response (FIG. 7B) and corresponding patient percentage distributions (FIG. 7C). Role function score improved on average 3.5 from baseline to C2D1 among patients taking ripretinib in contrast to placebo patients who saw on average, a decline from baseline to C2D1 of 17.1 (p=0.001). 70 patients were receiving ripretinib and 32 were receiving placebo.

Figures 8A, 8B:
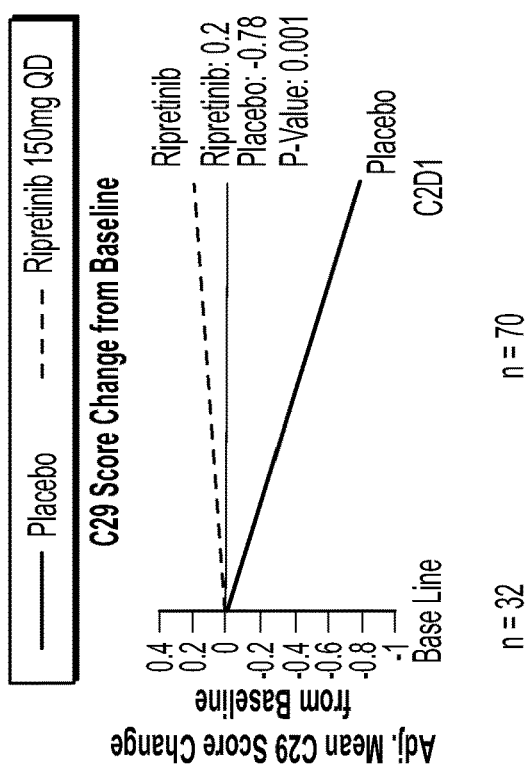
FIG. 8A and FIG. 8B depict patient score changes from baseline (FIG. 8A) and percentage distributions (FIG. 8B) in response to Question C29 of EORTC QLQ-C30 ("How would you rate your overall health during the past week?") from a scale of 1 ("Very poor") to 7 ("Excellent") in the study of Example 2 at 150 mg ripretinib QD. In the study, 70 patients were receiving ripretinib and 32 were receiving placebo.

FIG. 8A and FIG. 8B depict patient score changes from baseline (FIG. 8A) and corresponding patient percentage distributions (FIG. 8B) in response to Question C29 of EORTC QLQ-C30 ("How would you rate your overall health during the past week?") from a scale of 1 ("Very poor") to 7 ("Excellent"). There was a 0.20 improvement in C29 score in the ripretinib group compared to a 0.78 decrease in the placebo group (p=0.001). 70 patients were receiving ripretinib and 32 were receiving placebo.

Figures 9A, 9B:
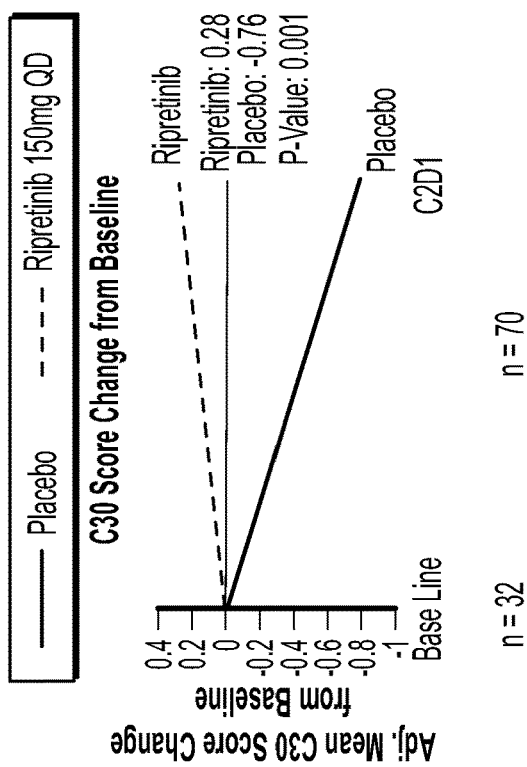
FIG. 9A and FIG. 9B depict patient score changes from baseline (FIG. 9A) and corresponding patient percentage distributions (FIG. 9B) in response to Question C30 of EORTC QLQ-C30 ("How would you rate your overall quality of life during the past week?") from a scale of 1 ("Very poor") to 7 ("Excellent") in the study of Example 2 at 150 mg ripretinib QD. In the study, 70 patients were receiving ripretinib and 32 were receiving placebo.

FIG. 9A and FIG. 9B depict patient score changes from baseline (FIG. 9A) and corresponding patient percentage distributions (FIG. 9B) in response to Question C30 of EORTC QLQ-C30 ("How would you rate your overall quality of life during the past week?") from a scale of 1 ("Very poor") to 7 ("Excellent"). There was a 0.28 improvement in score in the ripretinib group compared to a 0.76 decrease in the placebo group (p=0.001). 70 patients were receiving ripretinib and 32 were receiving placebo.

Figure 10:
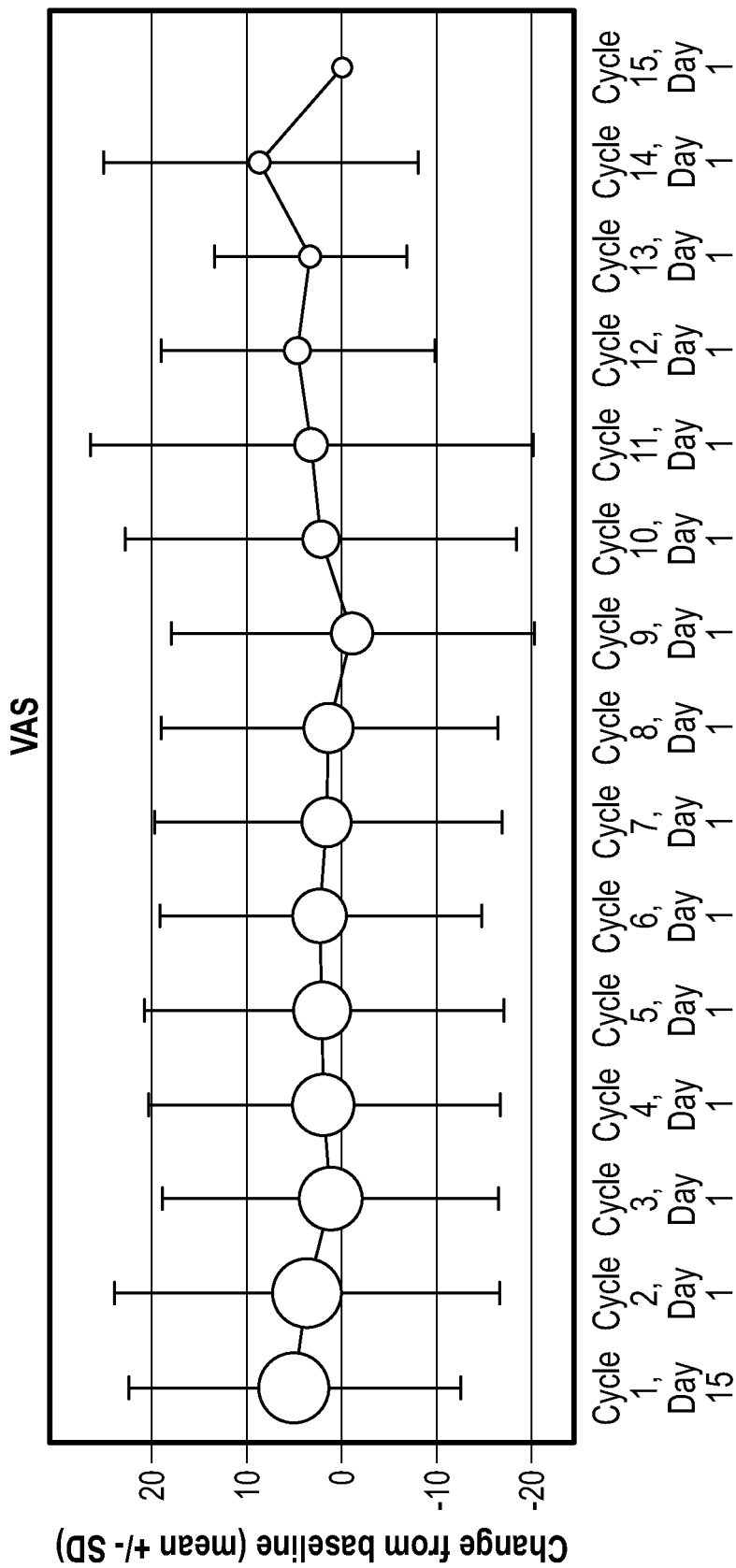
FIG. 10 depicts mean changes in baseline scores in EQ-VAS across various time points, from Cycle 1, Day 15 up to Cycle 15, Day 1 of the intention-to-treat population in the study of Example 2 at 150 mg ripretinib QD.
Figure 11A:
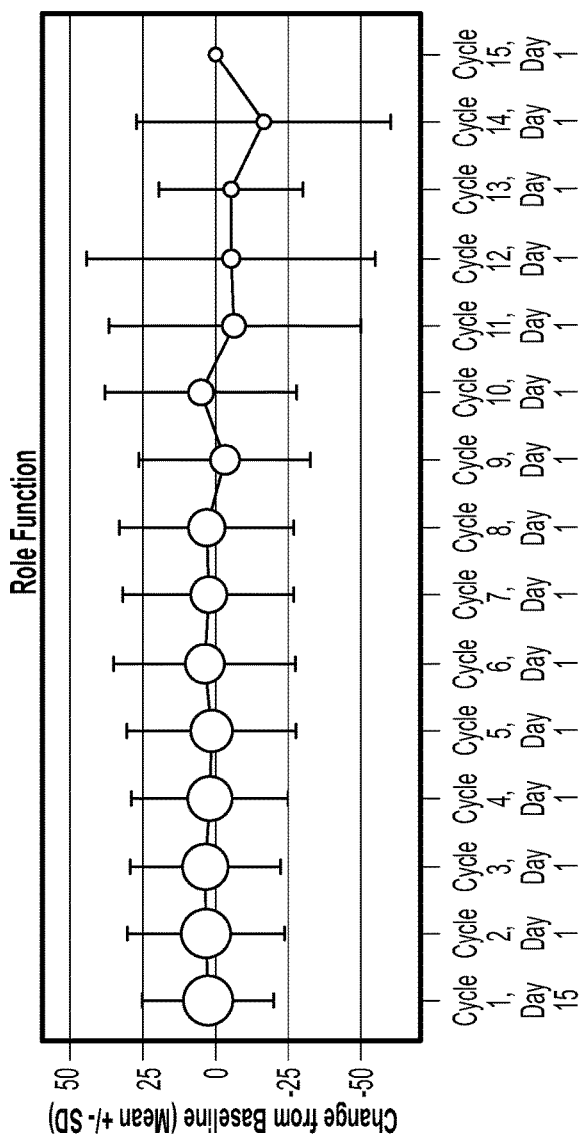
FIG. 11A and FIG. 11B depict mean changes in baseline scores in EORTC QLQ-C30 role function and EORTC QLQ-C30 physical function, respectively, across various time points, from Cycle 1, Day 15 up to Cycle 15, Day 1 of the intention-to-treat population in the study of Example 2 at 150 mg ripretinib QD.
Figure 11B:
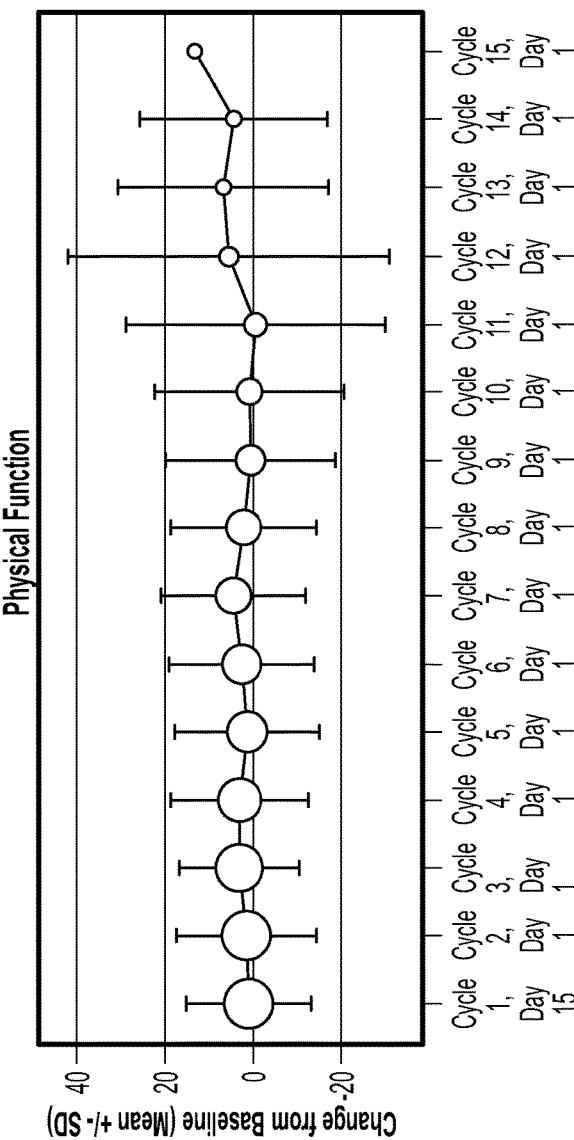
Figure 12A:
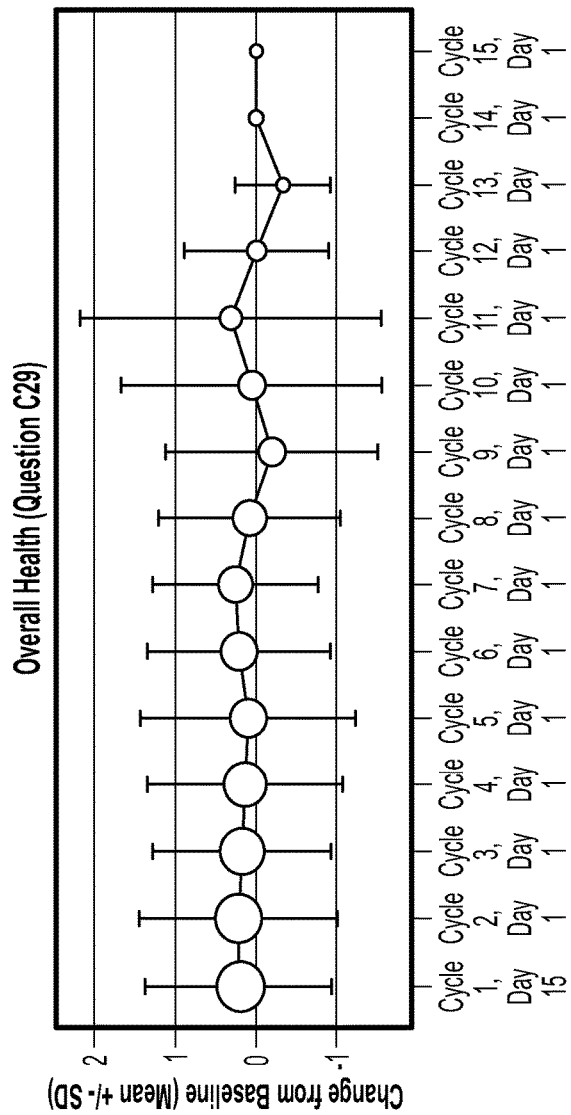
FIG. 12A and FIG. 12B depict mean changes in baseline scores in EORTC QLQ-C30 question C29 response and EORTC QLQ-C30 question C30 response, respectively, across various time points, from Cycle 1, Day 15 up to Cycle 15, Day 1 of the intention-to-treat population in the study of Example 2 at 150 mg ripretinib QD.
Figure 12B:
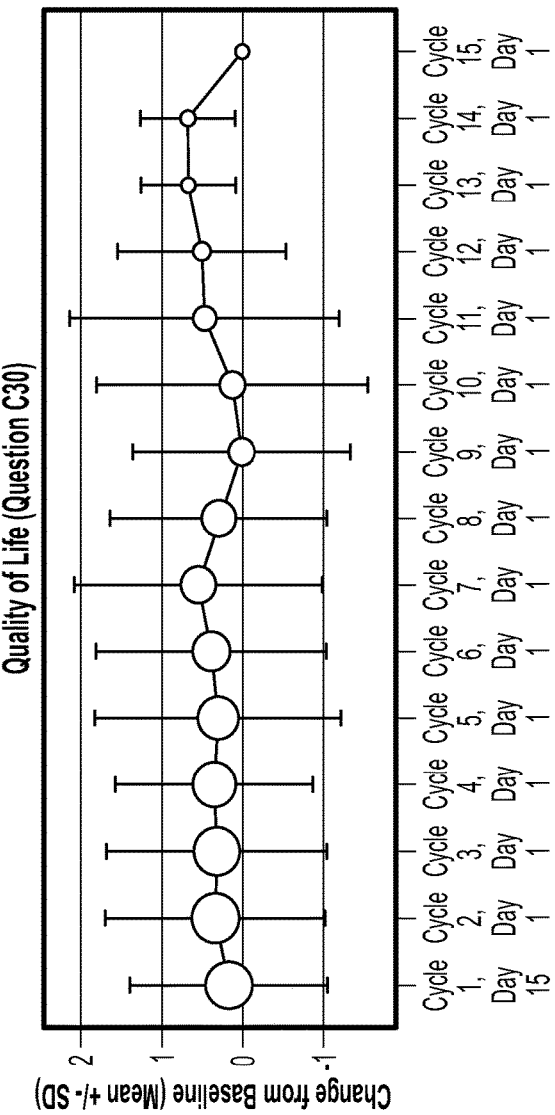

FIG. 10 depicts mean changes in baseline scores in EQ-VAS across various time points, from Cycle 1, Day 15 up to Cycle 15, Day 1 of the intention-to-treat population. FIG. 11A and FIG. 11B depict mean changes in baseline scores in EORTC QLQ-C30 role function and EORTC QLQ-C30 physical function, respectively, across various time points, from Cycle 1, Day 15 up to Cycle 15, Day 1 of the intention-to-treat population. FIG. 12A and FIG. 12B depict mean changes in baseline scores in EORTC QLQ-C30 question C29 response and EORTC QLQ-C30 question C30 response, respectively, across various time points, from Cycle 1, Day 15 up to Cycle 15, Day 1 of the intention-to-treat population.

Open-Label Phase and Dose Escalation

Patients whose disease progressed during the double blind phase of the study were escalated to 150 mg BID ripretinib, continued at the 150 mg QD dose, or discontinued in an open label-phase of the study. Table 8 shows a comparison of patients that received 150 mg QD ripretinib at the data cutoff time point of the double blind phase and the data cutoff time point of the open-label phase. The data in Table 8 suggest that data cut 9 months after the primary double-blind analysis has shown improvement in mOS and a similar mPFS in the ripretinib arm.

Figure 14A:
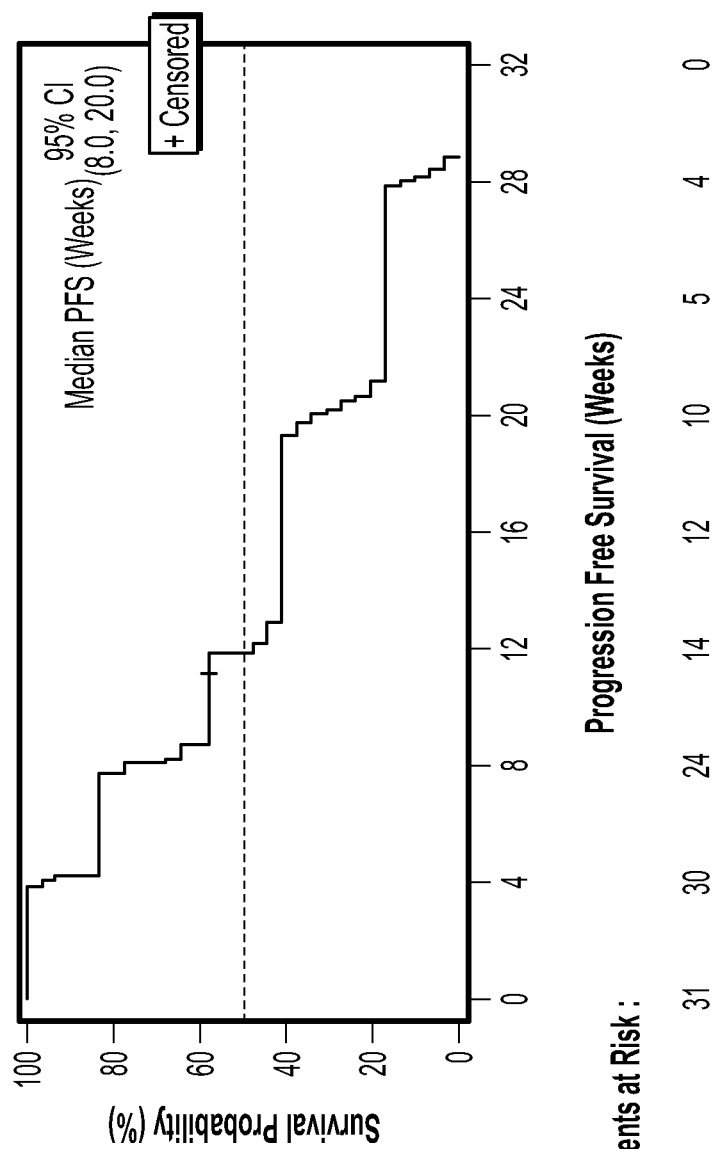

In the study, at least 31 patients dose escalated to 150 mg BID ripretinib in an open-label phase upon disease progression. PFS studies in the double-blind and open-label periods for these patients are depicted in FIG. 14A and FIG. 14B, respectively, with FIG. 14C depicting median PFS data.

Wild Type (KIT and PDGFRA) Mutations

PFS data among patients with wild-type KIT or PDGFRA mutations were further evaluated at 150 mg ripretinib QD. PFS data of patients with these wild-type KIT and PDGFRA mutations are shown in FIG. 15.

Additional Mutational Analyses

Figures 16A, 16B:
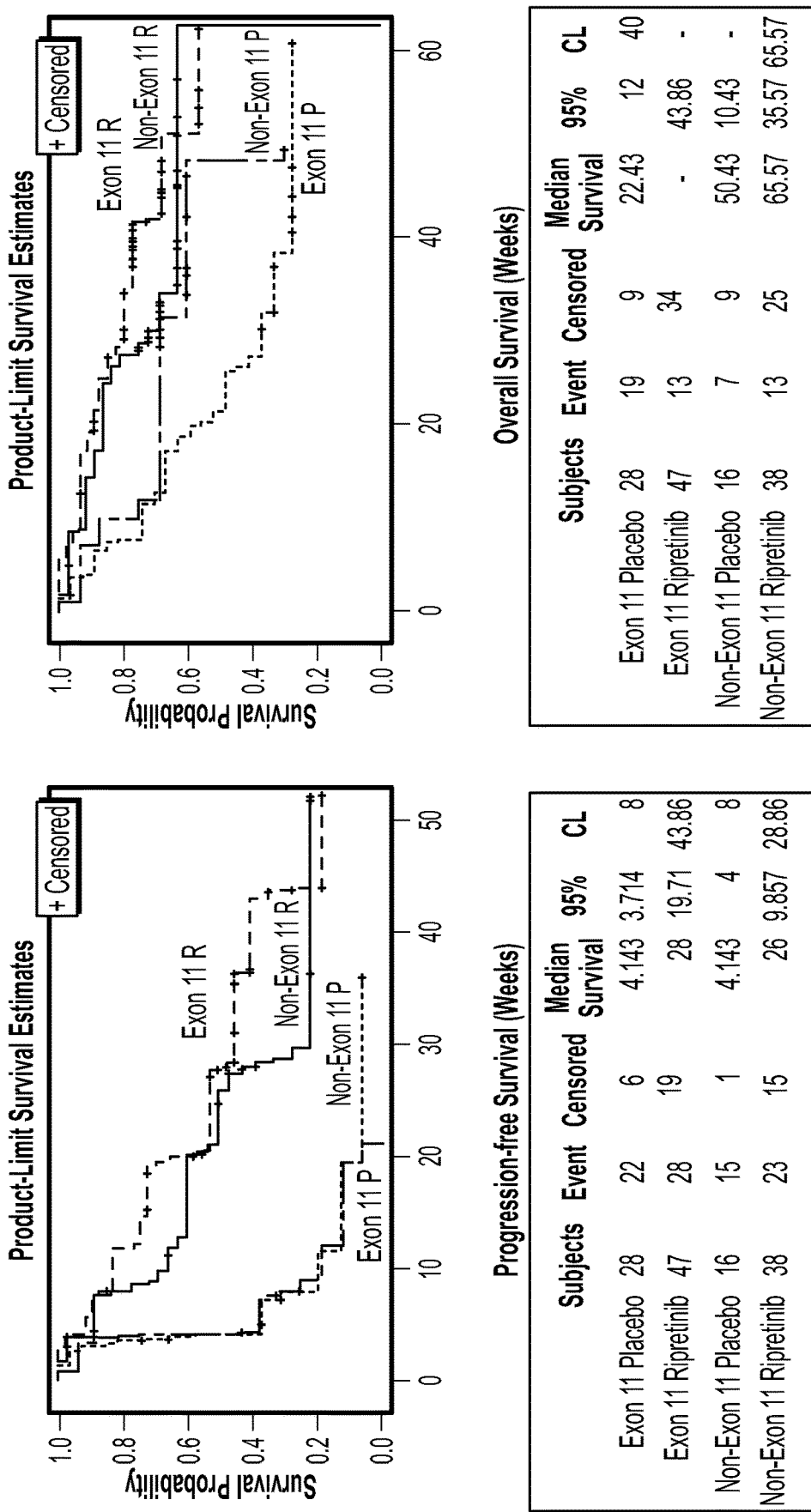
FIGS. 16A and 16B depict Progression free survival (PFS) and overall survival (OS) data based on patients with a primary Exon 11 mutation or those with a non-Exon 11 mutation in the study of Example 2 at 150 mg ripretinib QD.

Progression free survival PFS and overall survival (OS) data based on patients with a primary Exon 11 mutation or patients with a non-Exon 11 mutation are shown in FIGS. 16A (PFS) and 16B (OS) at 150 mg ripretinib QD. The data show that, regardless of primary mutation, whether a primary Exon 11 or a non-Exon 11 primary mutation, GIST patients derive similar benefit from ripretinib over placebo.

Figure 17B:
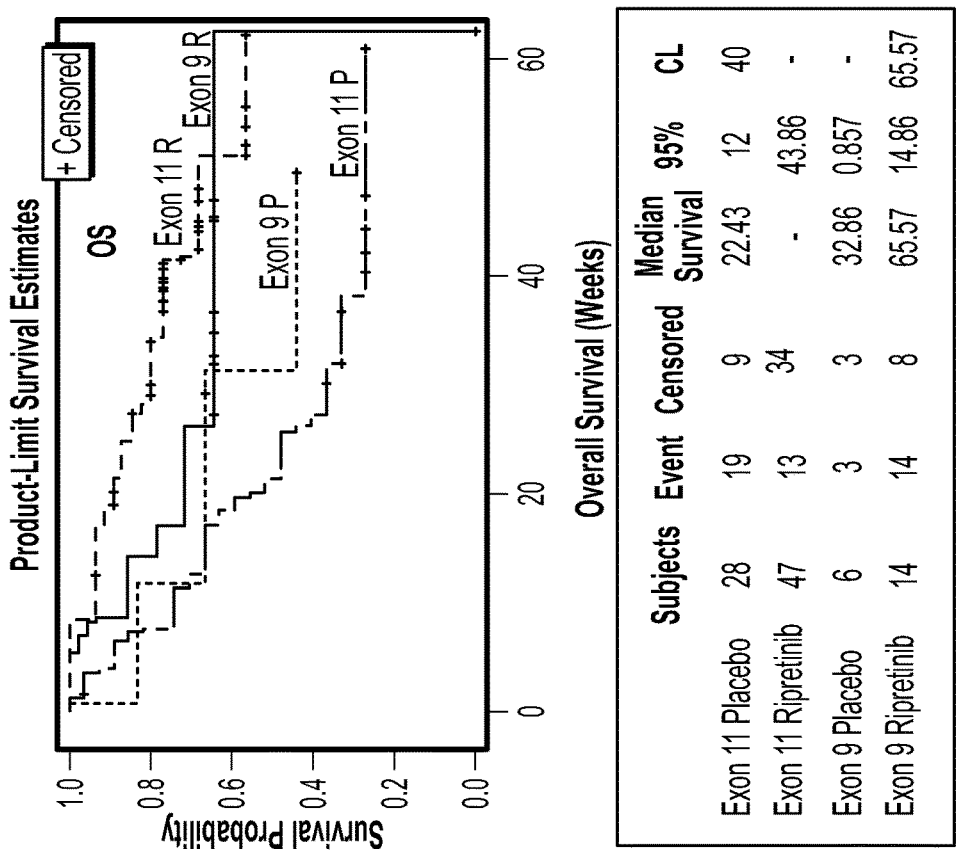
FIGS. 17A and 17B depicts progression free survival (PFS) and overall survival (OS) data based on patients with a primary Exon 11 mutation or a primary Exon 9 mutation in the study of Example 2 at 150 mg ripretinib QD.
Figure 17A:
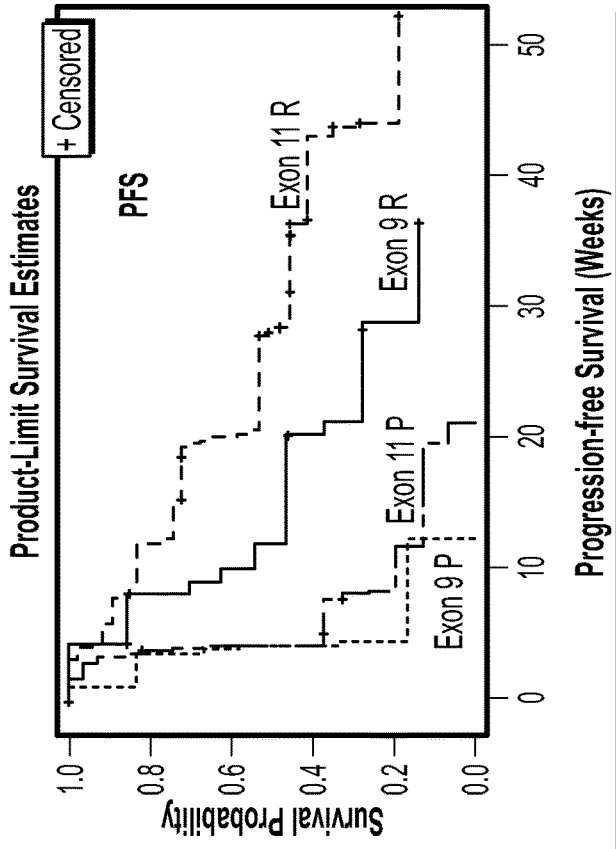

Progression free survival PFS and overall survival (OS) data based on patients with a primary Exon 11 mutation or those with a primary Exon 9 mutation are shown in FIGS. 17A (PFS) and 17B (OS) at 150 mg ripretinib QD. The data show that, Regardless of primary mutation, both Exon 11 and Exon 9 GIST patients derive a benefit from ripretinib over placebo.

Figure 18B:
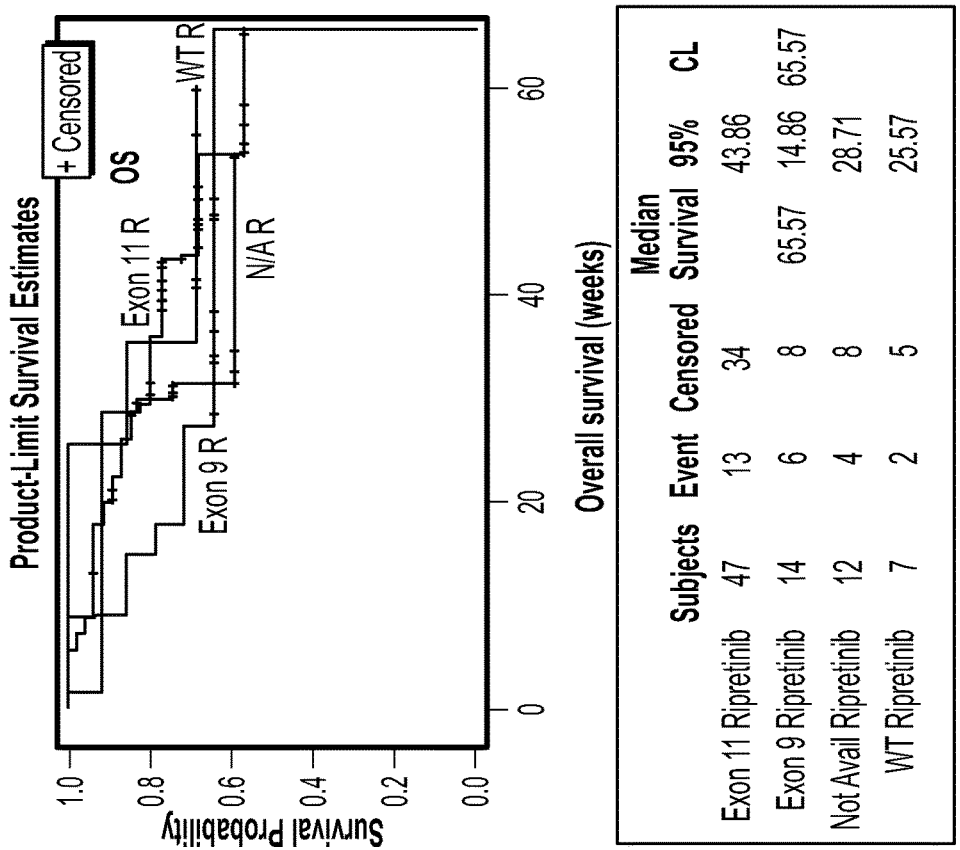
FIGS. 18A and 18B depicts progression free survival (PFS) and overall survival (OS) data based on patients with a primary Exon 11 mutation, or a primary Exon 9 mutation, or another mutation, or wild type (KIT and PDGFRA) in the study of Example 2 at 150 mg ripretinib QD.
Figure 18A:
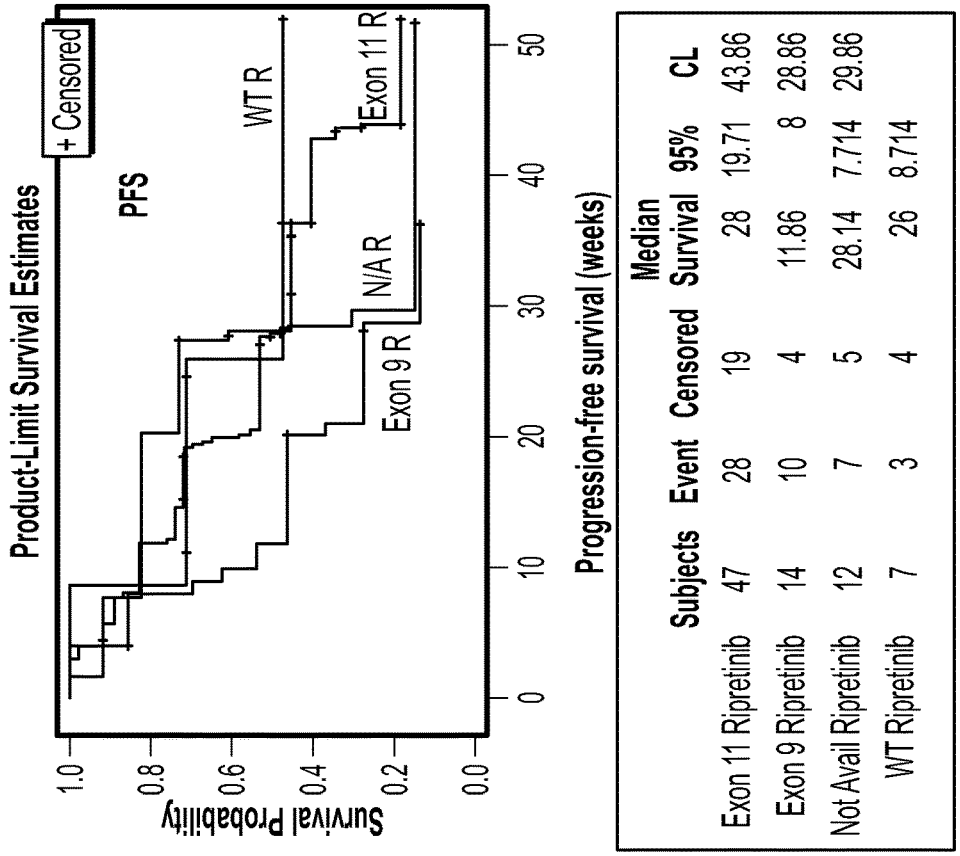

Furthermore, progression free survival PFS and overall survival (OS) data based on patients with a primary Exon 11 mutation, or a primary Exon 9 mutation, or other mutations, and wild type (KIT and PDGFRA) are shown in FIGS. 18A (PFS) and 19B (OS) at 150 mg ripretinib QD.

Figure 19A:
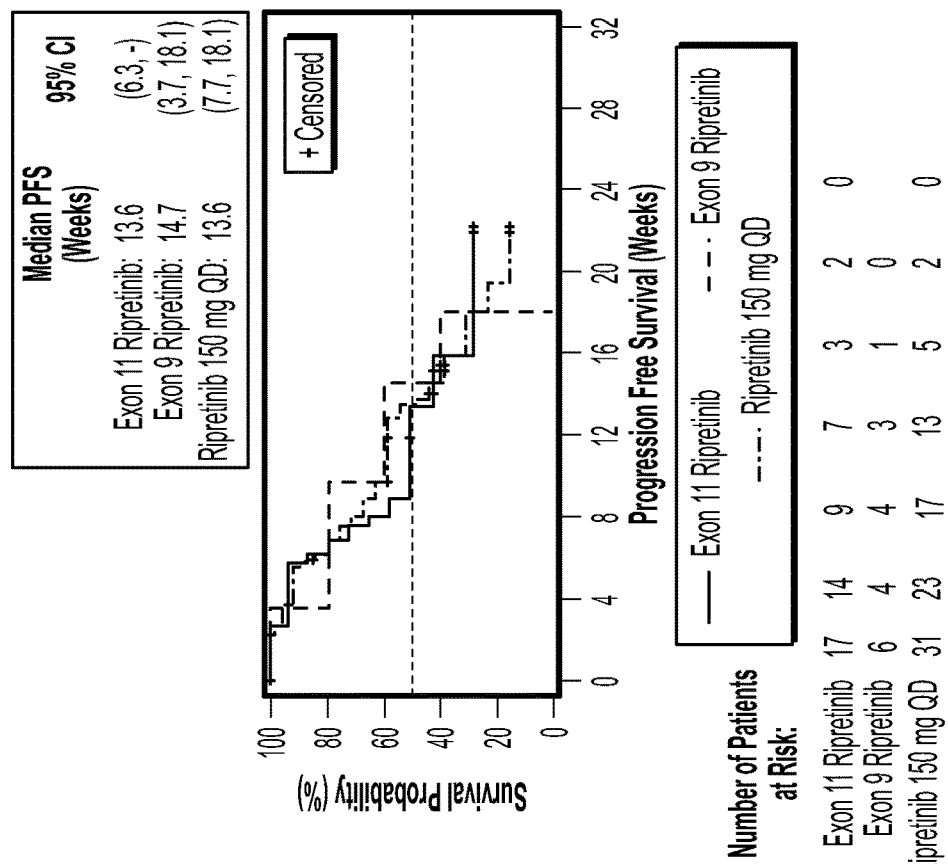
FIGS. 19A and 19B depicts progression free survival (PFS) studies for patients with certain primary mutations (Exon 9 or Exon 11) who dose escalated from 150 mg QD ripretinib to 150 mg BID ripretinib for the double-blind and open-label periods, respectively, in the study of Example 2.
Figure 19B:
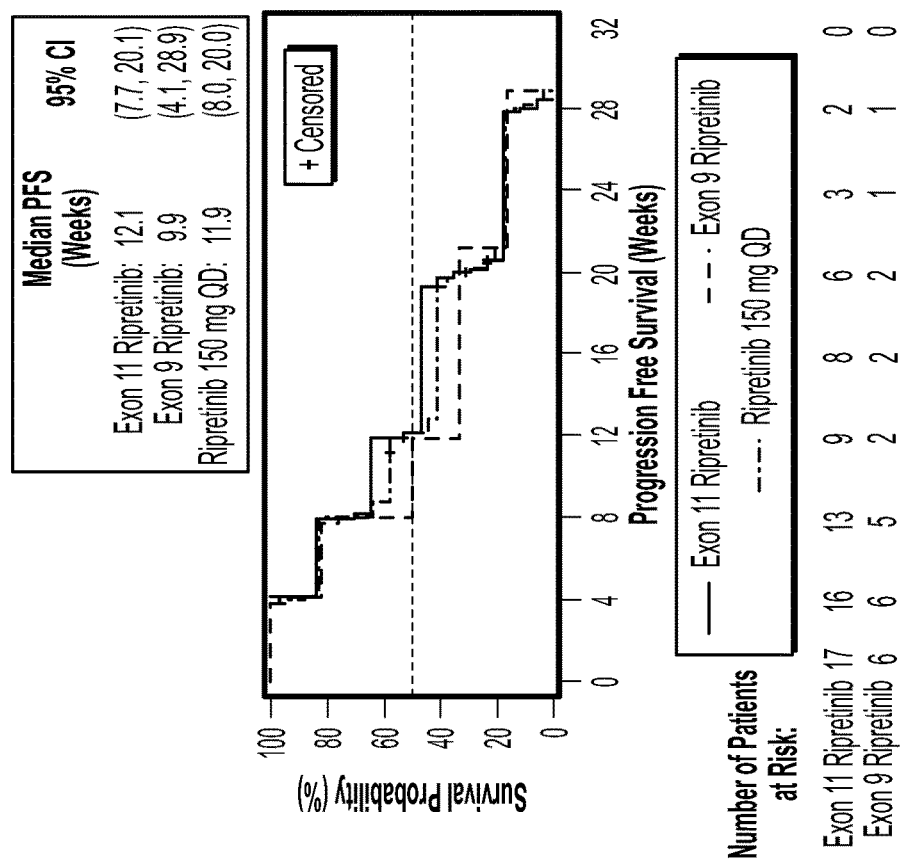

PFS studies for patients with certain primary mutations (Exon 9 or Exon 11) who dose escalated to 150 mg BID ripretinib are shown in FIGS. 19A and 19B for the double-blind and open-label periods, respectively.

Additionally, FIG. 20 shows exemplary progression free survival data for patients with other KIT mutations and PGDFR mutations in the study of Example 2 at 150 mg ripretinib QD.

FIGS. 26A-D depicts an exemplary comparison of PFS of patient subgroups with Exon 9 (FIG. 26A), Exon 11 (FIG. 26B), Exon 13 (FIG. 26C), or Exon 17 (FIG. 26D) KIT mutations. This exemplary data show that ripretinib showed PFS benefit in all assessed patient subgroups compared to placebo.

Example 3

Results for a Clinical Study of Ripretinib in Patients with Second-Line Through Fourth-Line Plus GIST Results. Data from 178 GIST patients receiving ripretinib at doses of ≥100 mg daily are noted in Table 2. The table includes investigator-assessed objective response rate (ORR) by best response, disease control rate (DCR) and median progression free survival (mPFS), all of which were determined by Response Evaluation Criteria in Solid Tumors (RECIST) version 1.1.

TABLE 2

Results/clinical study of ripretinib

| Line of Therapy[1] | Objective Response Rate by Best Response Includes Unconfirmed (Confirmed Only) | Disease Control Rate at 3 Months | Median Progression Free Survival (mPFS) | Censored Patients for mPFS | Mean Treatment Duration[2][3] |
|---|---|---|---|---|---|
| Second-Line (n = 37) | 30% (22%) | 81% | 42 weeks | 38% | 43 weeks |
| Third-Line (n = 31) | 23% (13%) | 80% | 40 weeks | 32% | 48 weeks |
| Fourth-Line (n = 60) | 15% (8%) | 73% | 30 weeks | 30% | 49 weeks |
| ≥Fourth-Line (n = 110)[4] | 11% (7%) | 66% | 24 weeks | 22% | 41 weeks |

In Table 2, (1) indicates overall number of patients (n=178) remains the same as prior data presented at ESMO 2018; based on additional data cleaning, one patient from each of $2^{nd}$ line and $4^{th}/≥4^{th}$ line were reclassified as $3^{rd}$ line patients; (2) refers to median treatment durations were: $2^{nd}$ line=44 weeks, $3^{rd}$ line=48 weeks, $4^{th}$ line=46 weeks and $≥4^{th}$ line=29 weeks; (3) refers to including 60 patients who elected for intra-patient dose escalation from 150 mg QD to 150 mg BID; and (4) refers to the number of patients including 60 patients from $4^{th}$ line.

Ripretinib was generally well tolerated and the updated adverse events were consistent with previously presented Phase 1 data in patients with GIST. Grade 3 or 4 treatment-emergent adverse events (TEAEs) in >5% of patients were lipase increased (18%; n=33), anemia (11%; n=20), hypertension (7%; n=13) and abdominal pain (6%; n=11). 13% of patients (n=24) experienced TEAEs leading to study treatment discontinuation, 17% of patients (n=31) experienced TEAEs leading to dose reduction and 49% of patients (n=88) had TEAEs leading to study drug interruption. Table 3 lists TEAEs>10% for GIST patients treated with ≥100 mg of ripretinib daily.

TABLE 3

Treatment-emergent adverse events for patients administered with 100 mg of ripretinib daily.
GIST PATIENTS @ ≥ 100 MG DAILY
Treatment Emergent Adverse Events (TEAEs) > 10%

| | | | |
|---|---|---|---|
| Alopecia | 102 (57%) | 0 (0%) | 102 (57%) |
| Fatigue | 94 (53%) | 4 (2%) | 98 (55%) |
| Myalgia | 79 (44%) | 0 (0%) | 79 (44%) |
| Nausea | 77 (43%) | 1 (1%) | 78 (44%) |
| Palmar-plantar erythrodysaesthesia syndrome | 71 (40%) | 1 (1%) | 72 (40%) |
| Constipation | 67 (37%) | 0 (0%) | 67 (37%) |
| Decreased appetite | 60 (34%) | 2 (1%) | 62 (35%) |
| Diarrhea | 50 (28%) | 3 (2%) | 53 (30%) |
| Weight decreased | 51 (29%) | 1 (1%) | 52 (29%) |
| Lipase increased | 18 (10%) | 33 (18%) | 51 (29%) |
| Muscle spasms | 47 (26%) | 0 (0%) | 47 (26%) |
| Abdominal pain | 33 (18%) | 11 (6%) | 44 (25%) |
| Vomiting | 42 (24%) | 2 (1%) | 44 (25%) |
| Arthralgia | 40 (22%) | 0 (0%) | 40 (22%) |
| Anemia | 18 (10%) | 20 (11%) | 38 (21%) |
| Hypertension | 25 (14%) | 13 (7%) | 38 (21%) |
| Cough | 37 (21%) | 0 (0%) | 37 (21%) |
| Dry skin | 37 (21%) | 0 (0%) | 37 (21%) |
| Dyspnea | 32 (18%) | 4 (2%) | 36 (20%) |
| Headache | 33 (18%) | 1 (1%) | 34 (19%) |
| Back Pain | 30 (17%) | 2 (1%) | 32 (18%) |
| Dizziness | 29 (16%) | 0 (0%) | 29 (16%) |
| Rash | 27 (15%) | 0 (0%) | 27 (15%) |
| Hypokalaemia | 21 (12%) | 5 (3%) | 26 (15%) |
| Hypophosphataemia | 17 (10%) | 8 (5%) | 25 (14%) |
| Actinic keratosis | 25 (14%) | 0 (0%) | 25 (14%) |

TABLE 3-continued

Treatment-emergent adverse events for patients administered with 100 mg of ripretinib daily.
GIST PATIENTS @ ≥ 100 MG DAILY
Treatment Emergent Adverse Events (TEAEs) > 10%

| | | | |
|---|---|---|---|
| Blood bilirubin increase | 16 (9%) | 5 (3%) | 21 (12%) |
| Amylase increased | 19 (11%) | 2 (1%) | 21 (12%) |
| Insomnia | 21 (12%) | 0 (0%) | 21 (12%) |
| Seborrhoeic keratosis[2] | 21 (12%) | 0 (0%) | 21 (12%) |
| Urinary tract infection | 16 (9%) | 4 (2%) | 20 (11%) |
| Dysgeusia | 20 (11%) | 0 (0%) | 20 (11%) |
| Pain in extremity | 18 (10%) | 1 (1%) | 19 (11%) |
| Blood creatine phosphokinase increased | 13 (7%) | 5 (3%) | 18 (10%) |
| Upper respiratory tract infection | 18 (10%) | 0 (0%) | 18 (10%) |
| Rash maculo-papular | 18 (10%) | 0 (0%) | 18 (10%) |

TABLE 3-continued

Treatment-emergent adverse events for patients administered with
100 mg of ripretinib daily.
GIST PATIENTS @ ≥ 100 MG DAILY
Treatment Emergent Adverse Events (TEAEs) > 10%

| | | | |
|---|---|---|---|
| Hypomagnesaemia | 18 (10%) | 0 (0%) | 18 (10%) |
| Pruritus | 18 (10%) | 0 (0%) | 18 (10%) |
| Skin papilloma[(2)] | 17 (10%) | 0 (0%) | 17 (10%) |
| Vision blurred | 17 (10%) | 0 (0%) | 17 (10%) |

In table 3, (1) refers to including one patient that only participated in the food effect portion of the Phase 1 study; and (2) indicates that dermatology skin exams were implemented to better evaluate skin lesions.

Example 4

Results for a Clinical Study of 150 mg QD Ripretinib Administered to Patients with Second-Line Through Fourth-Line Plus GIST Efficacy and safety results from the escalation and expansion phases of a phase 1 study for patients with GIST treated at ripretinib 150 mg QD as the starting dose in 28-day cycles are presented. Local, investigator-assessed Response Evaluation Criteria in Solid Tumors (RECIST 1.1) response assessments were performed every 2 cycles, and patients in the expansion cohorts who progressed per RECIST 1.1 were allowed to dose escalate to 150 mg BID.

142 patients with GIST in the escalation and expansion phases were treated at 150 mg QD dose. Number of patients by line of therapy were as follows: 31 $2^{nd}$ line, 28 $3^{rd}$ line, and 83≥$4^{th}$ line patients. 135 patients (95.1%) had KIT-mutant GIST, and 7 patients (4.9%) had PDGFRA-mutant GIST.

Figure 4:
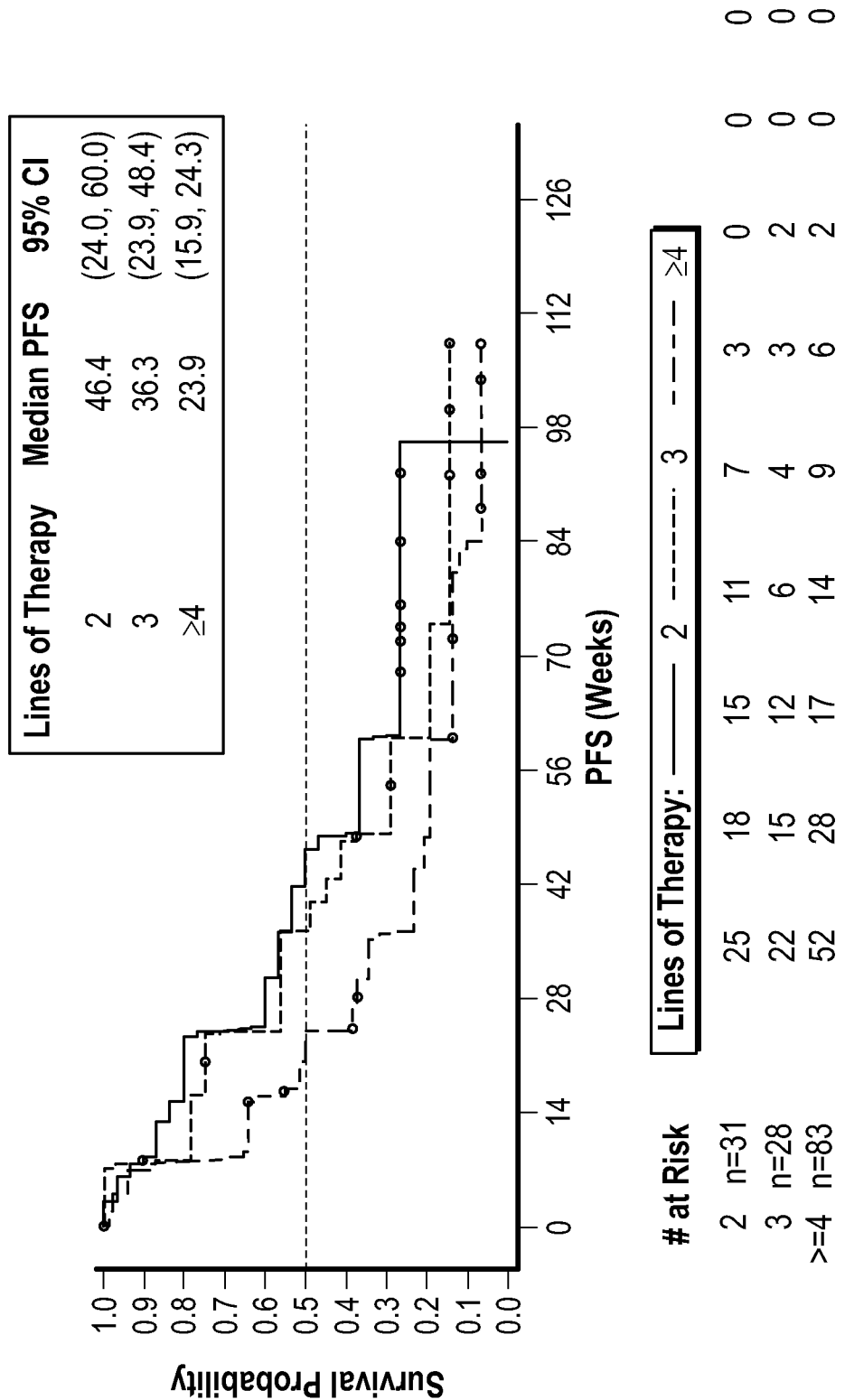
FIG. 4 depicts PFS by line of therapy for patients with GIST treated with 150 mg once daily of ripretinib.

Results on the efficacy by line of therapy in patients with GIST receiving ripretinib 150 mg QD are presented in Table 4. For example, the confirmed-only complete response (CR), partial response (PR), stable disease, and progressive disease are presented in Table 4. The objective response rate data in Table 4 relates to the proportion of patients with CR+PR. The median PFS data in Table 4 refers to progression-free survival per investigator assessment, by line of therapy. PFS plots by line of therapy are also shown in FIG. 4.

TABLE 4

Efficacy by line of therapy in patients with GIST receiving ripretinib 150 mg QD.

| Parameters | $2^{nd}$ Line (n = 31) | $3^{rd}$ Line (n = 28) | ≥$4^{th}$ Line (n = 83) |
|---|---|---|---|
| Best response (confirmed only), n (%) | | | |
| CR | 0 | 0 | 0 |
| PR | 6 (19.4) | 4 (14.3) | 6 (7.2) |
| Stable disease | 21 (67.7) | 18 (64.3) | 49 (59.0) |
| Progressive disease | 4 (12.9) | 6 (21.4) | 22 (26.5) |
| Not evaluable | 0 | 0 | 1 (1.2) |
| No response assessment | 0 | 0 | 5 (6.0) |
| ORR, n (95% CI) | 19.4 (7.5, 37.5) | 14.3 (4.0, 32.7) | 7.2 (2.7, 15.1) |
| Duration of treatment[a] | | | |
| Mean, weeks (SD) | 56.1 (34.24) | 57.5 (32.95) | 44.9 (36.58) |
| Median, weeks | 64 | 51 | 29 |
| Min, Max | 4, 132 | 8, 124 | 0.1, 140 |
| Duration of response | | | |
| n | 6 | 4 | 6 |
| Number of events | 3 | 1 | 3 |
| Median, weeks | 80 | NE | 76.1 |
| 95% CI | 24.7, 80.0 | 52.1, NE | 24.1, NE |
| PFS | | | |
| Number of censored patients | 8 | 6 | 12 |
| Median, weeks | 46.4 | 36.3 | 23.9 |
| 95% CI | 24.0, 60.0 | 23.9, 48.4 | 15.9, 24.3 |

In Table 4: [a]64 subjects escalated to 150 mg BID among patients with GIST in the 150 mg QD dose group. CI, confidence interval; CR, complete response; NE, not estimable; ORR, objective response rate; PFS, progression-free survival; PR, partial response; SD, standard deviation. Local (investigator) response assessment.

Figure 25A:
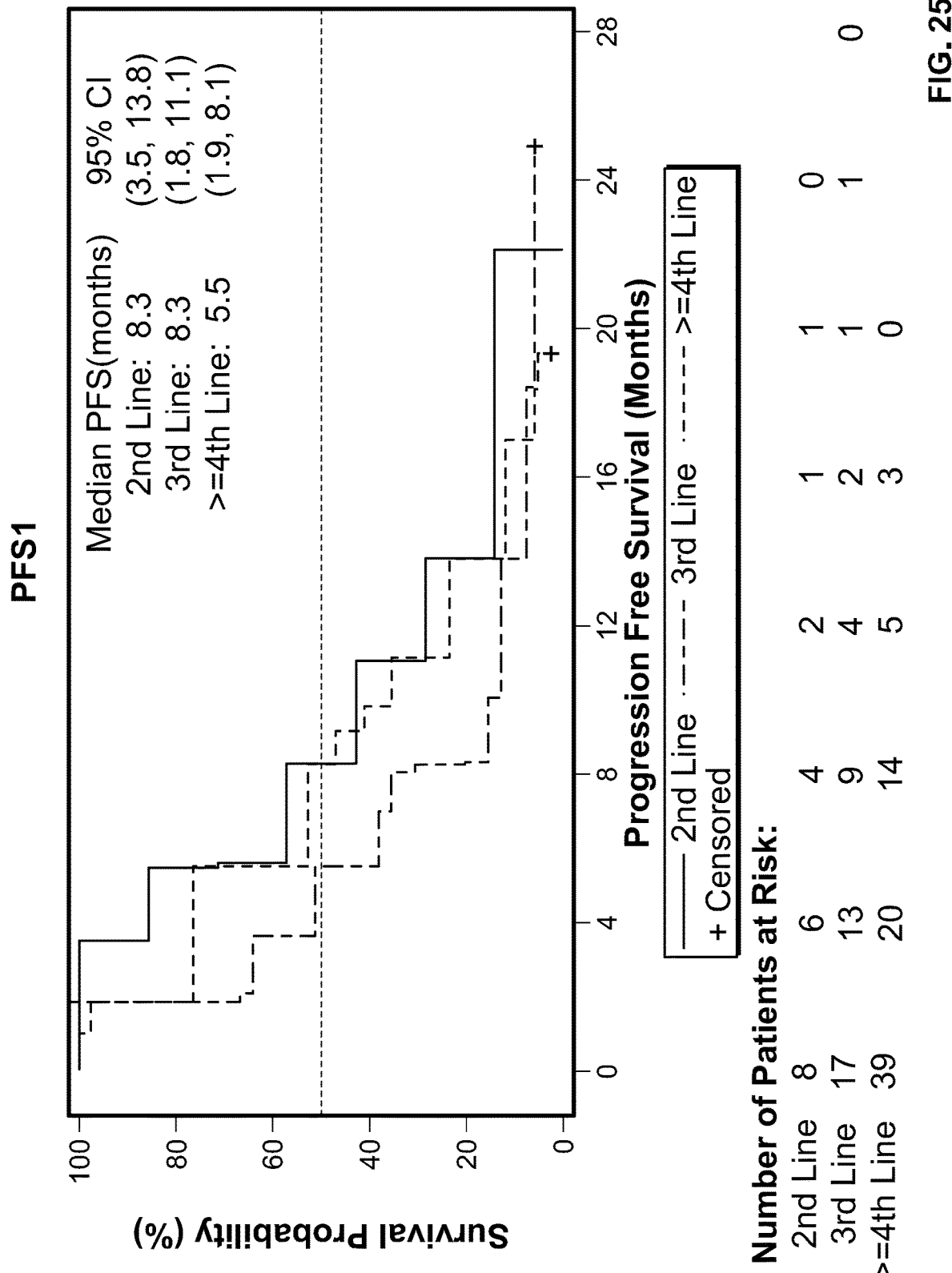
FIG. 25A and FIG. 25B depict exemplary PFS of subjects who dose escalated to 150 mg BID, PFS before (PFS1) and after (PFS2) dose escalation.
Figure 25B:
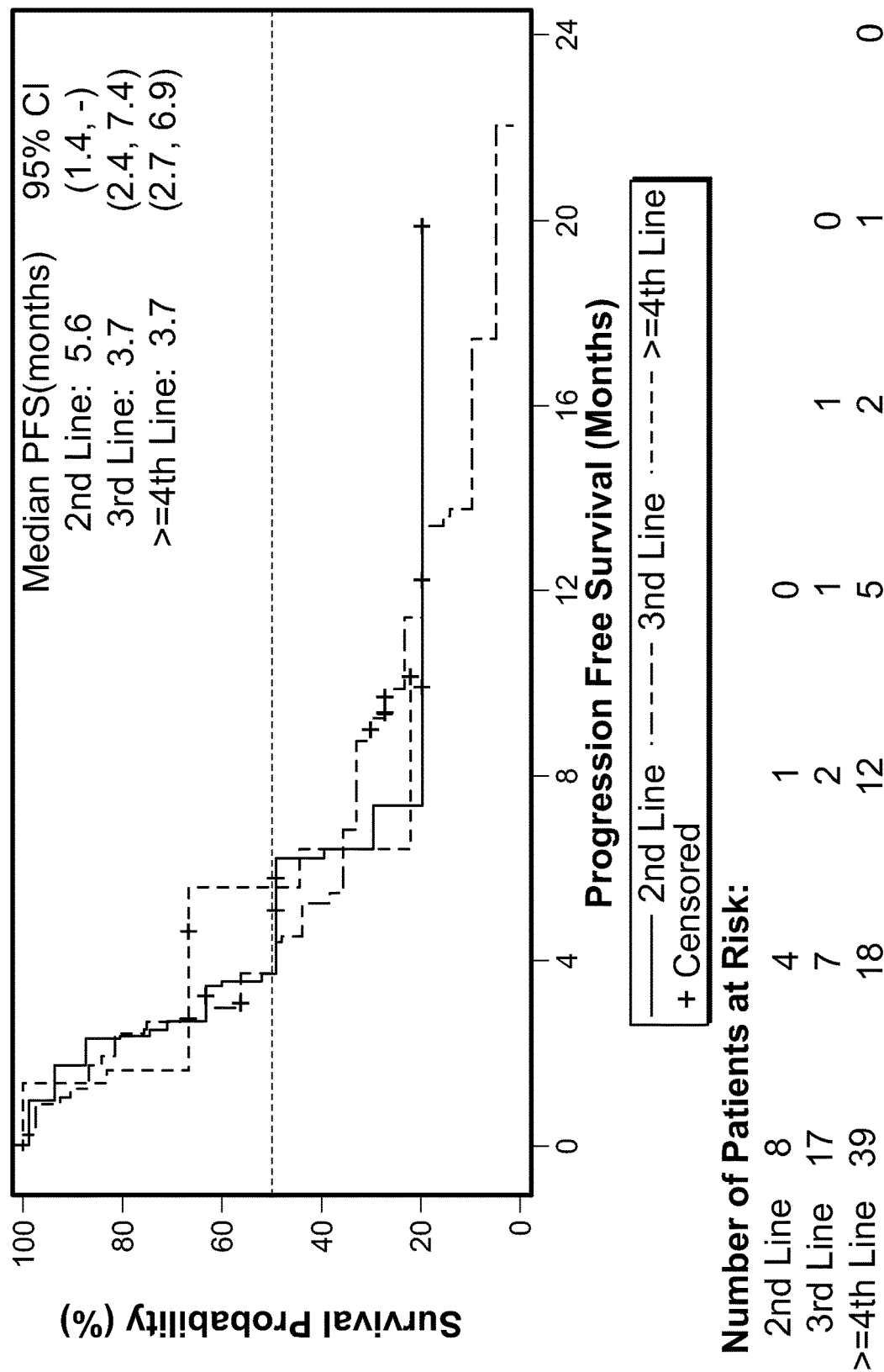

In subjects dose escalated to 150 mg BID, PFS before (PFS1) and after (PFS2) dose escalation was evaluated and is shown in FIGS. 25A and 25B, respectively. The data support that, regardless of line of therapy, patients received additional clinical benefit by investigator assessment after dose escalation to 150 mg BID.

Mutational Analysis

Figure 27:
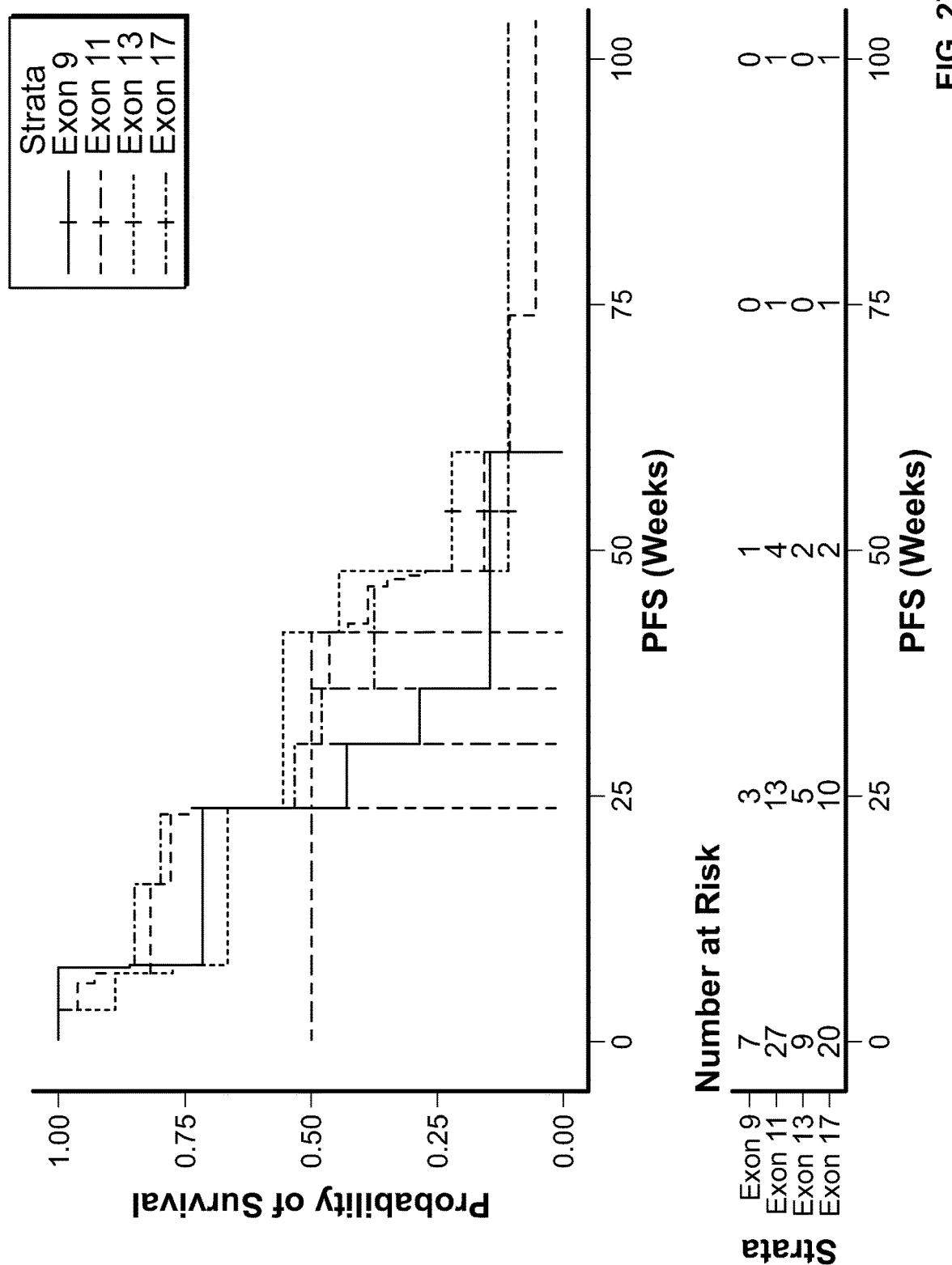
FIG. 27 shows PFS data of exemplary second and third-line patients with Exons 9, 11, 13, or 17 KIT mutations. The data show that, in second and third line populations, patients with such various KIT mutations have comparable PFS.

FIG. 27 shows PFS data of exemplary second and third-line patients with Exons 9, 11, 13, or 17 KIT mutations. The data show that, in second and third line populations, patients with such various KIT mutations have comparable PFS.

Example 5

Protocol for Dose Modification of Ripretinib as a Result of Adverse Reactions

If dose modifications of ripretinib are required due to adverse reactions, the following protocol will be applied: reduce the dose in 50 mg (one tablet) increments; the lowest recommended dose of ripretinib is 50 mg once daily. Ripretinib dosage reductions for adverse reactions are summarized in Table 5.

TABLE 5

Recommended Dose Reduction for Adverse Reactions

| Dose Level | Dose |
| --- | --- |
| Recommended starting dose | 150 mg once daily |
| First dose reduction | Reduce to 100 mg once daily |
| Second dose reduction (lowest recommended dose) | Reduce to 50 mg once daily |

Dosing will be reduced, interrupted, or discontinued for certain toxicities. See Table 6 for dose modification guidelines.

TABLE 6

Recommended Dose Modifications for ripretinib

| Adverse Reaction | Severity[a] | Dosage Modifications |
| --- | --- | --- |
| Hand-foot skin reaction (HFSR) [palmar-plantar erythrodysesthesia syndrome (PPES)] | Grade 2 | Interrupt ripretinib for at least 7 days. If the event returns to Grade 1 or baseline within 7 days, resume ripretinib at the same dose level. If the event returns to Grade 1 or baseline after 7 days, resume ripretinib at a reduced dose level (see Table 5). If after a dose reduction, the event is maintained at Grade 1 or baseline for at least 28 days, consider re-escalating ripretinib by 1 dose level (see Table 5). If this is a recurrence, after event returns to Grade 1 or baseline, resume ripretinib at a reduced dose level (see Table 5) regardless of time to improvement. |
| | Grade 3 | Interrupt ripretinib for at least 7 days or until the event returns to Grade 1 or baseline (maximum 28 days). Resume ripretinib at a reduced dose level (see Table 5). If after a dose reduction the event is maintained at Grade 1 or baseline for at least 28 days of dosing, consider re-escalating ripretinib by 1 dose level (see Table 5). |
| Hypertension | Grade 3 | Medically manage hypertension to achieve normal blood pressure. If symptomatic hypertension, withhold ripretinib and treat hypertension. Resume ripretinib at the same dose level after symptoms have resolved. If blood pressure is not controlled with medical management, reduce ripretinib to the next dose level (see Table 5). If Grade 3 hypertension recurs despite ripretinib dose reduction and medical management, reduce ripretinib to the lowest recommended dose of 50 mg once daily. |
| | Grade 4 Life-threatening consequences (e.g., malignant hypertension, transient or permanent neurologic deficit, hypertensive crisis) | Discontinue ripretinib permanently. |

TABLE 6-continued

Recommended Dose Modifications for ripretinib

| Adverse Reaction | Severity[a] | Dosage Modifications |
|---|---|---|
| Arthralgia/Myalgia | Grade 2 | Interrupt ripretinib for at least 7 days. If the event returns to Grade 1 or baseline within 7 days, resume ripretinib at the same dose level. If the event returns to Grade 1 or baseline after 7 days, resume ripretinib at a reduced dose level (see Table 5). If after a dose reduction, the event is maintained at Grade 1 or baseline for at least 28 days of dosing, consider re-escalating ripretinib by 1 dose level (see Table 5). If this is a recurrence, after event returns to Grade 1 or baseline, resume ripretinib at a reduced dose level (see Table 5) regardless of time to improvement. |
| | Grade 3 | Interrupt ripretinib for at least 7 days or until the event returns to Grade 1 or baseline (maximum 28 days). Resume ripretinib at a reduced dose level (see Table 5). If after a dose reduction the event is maintained at Grade 1 or baseline for at least 28 days of dosing, consider re-escalating ripretinib by 1 dose level (see Table 5). |
| Other adverse reactions | Grade 3 or higher toxicity considered related to treatment | Interrupt ripretinib until toxicity resolves to Grade 1 or baseline (maximum 28 days). If the event returns to Grade 1 or baseline, resume ripretinib at a reduced dose level (see Table 5). If the reduced dose is tolerated without recurrence of the event for at least 28 days, consider re-escalating ripretinib to the prior dose level (see Table 5). If Grade 3 or higher toxicity recurs, discontinue ripretinib. |

BP = blood pressure; DBP = diastolic blood pressure; SBP = systolic blood pressure
[a]Graded per National Cancer Institute Common Terminology Criteria for Adverse Events (NCI CTCAE) version 4.03

Example 6

Safety of Ripretinib and Impact of Alopecia and Palmar-Plantar Erythrodysesthesia (PPES) on Patient-Reported Outcomes The safety of ripretinib and the impact of alopecia and palmar-plantar erythrodysesthesia (PPES) on patient-reported outcomes (PROs) of patients treated in the study described in Example 2 herein are described. Ripretinib had a favorable overall safety and tolerability profile in the trial of Example 2. When stratified by alopecia and PPES, patient reported assessments of function, overall health, and overall quality of life were maintained over time. For both alopecia and PPES, onset and maximum severity occurred almost simultaneously, indicating that these events generally did not progressively worsen. Overall, these results suggest that alopecia and PPES are manageable and that ripretinib treatment offsets any negative impact associated with these AEs.

Patient reported outcomes (PROs) were assessed with questions from the EuroQol 5D (EQ 5D 5L) and the European Organization for the Research and Treatment of Cancer Quality of Life Questionnaire (EORTC QLQ C30).

Generalized estimating equation (GEE) models were used in statistical analyses in which: Repeated measures models across visits where the outcome was 1 of the 5 PROs; models were built only for ripretinib patients; for alopecia patients, cycles 1 and 2 were excluded to account for median time of alopecia onset; covariates were sex, alopecia/PPES (yes/no), and Eastern Cooperative Oncology Group (ECOG) score at baseline; and when there was no end date for the AE, it was coded conservatively as having extended to the last visit of the double blind period.

Figure 21:
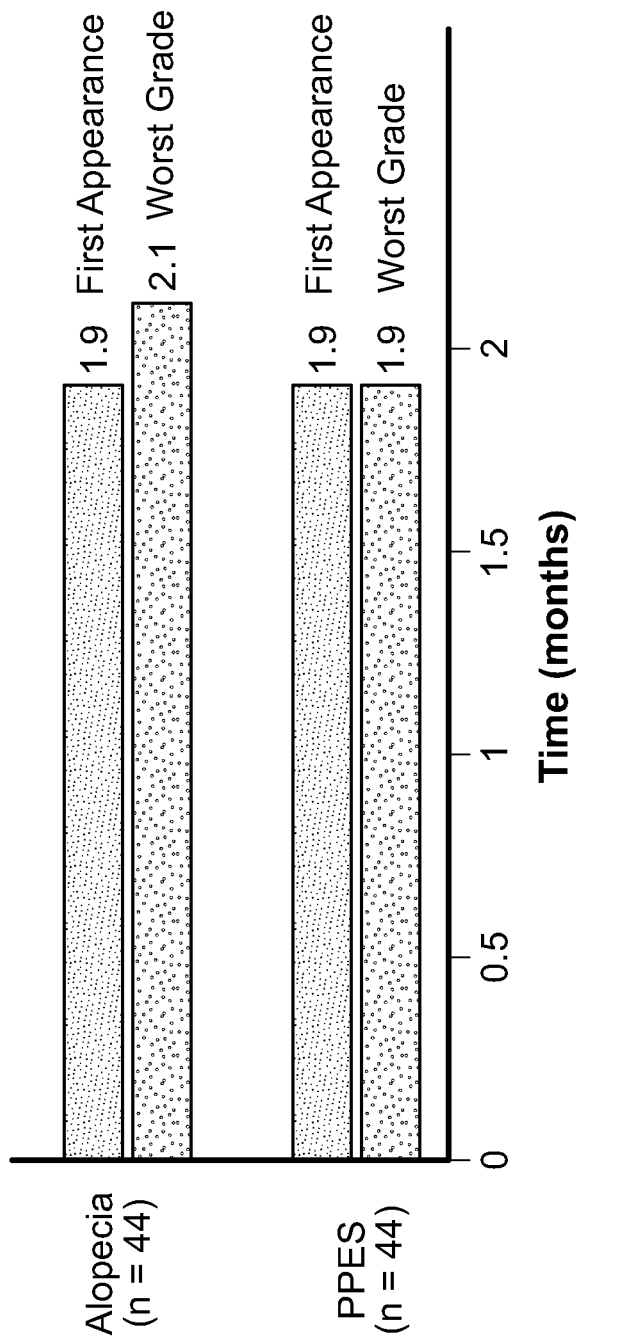
FIG. 21 depicts the median first appearance and worst grade of alopecia and PPES in corresponding patients receiving ripretinib in the study described in Example 2.
Figure 22A:
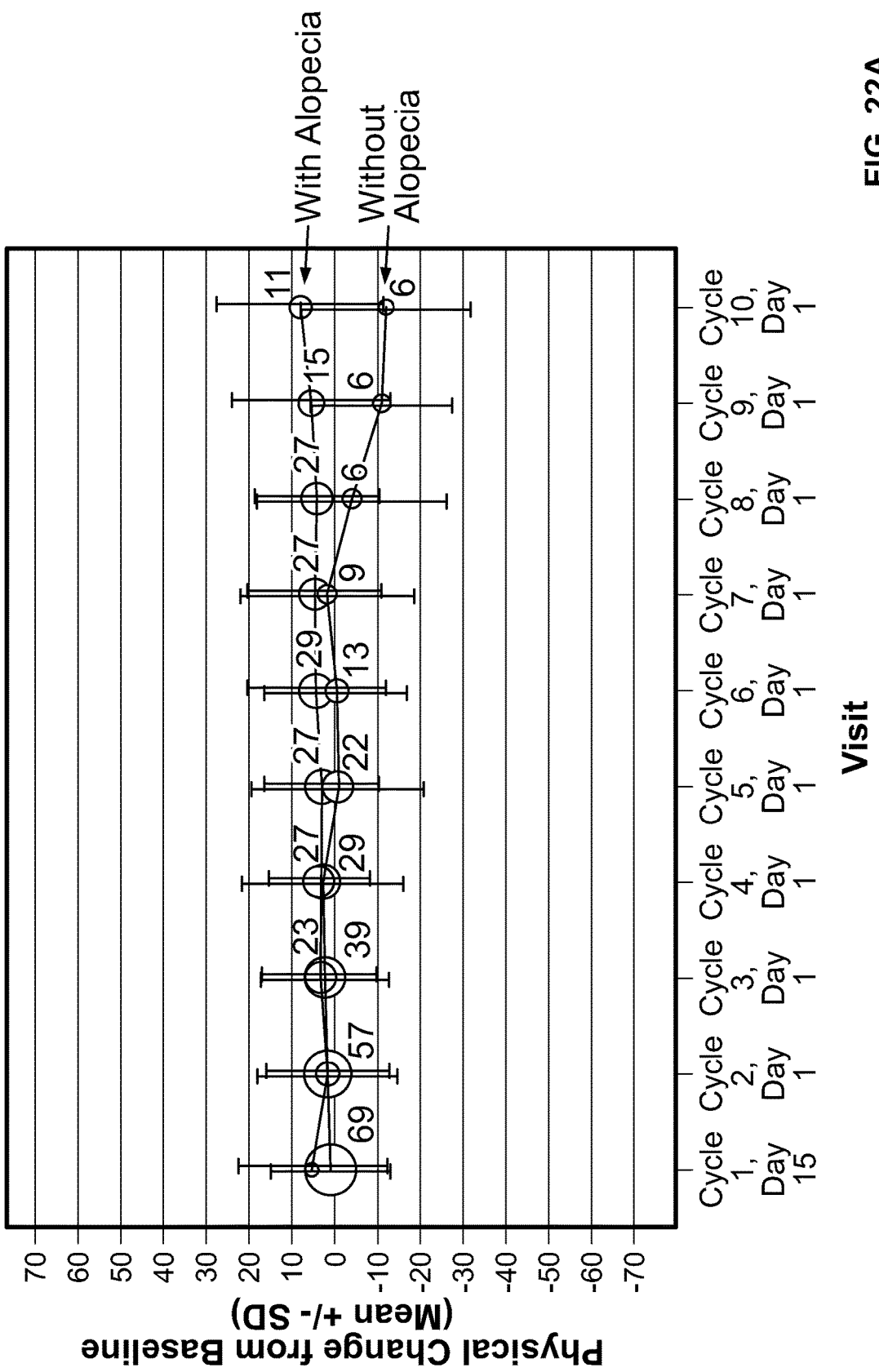
FIG. 22A depicts a mean change from baseline for physical function patient reported outcome of the EORTC-QLQ-C30 in patients receiving ripretinib, with and without alopecia, in the study described in Example 2.
Figure 22B:
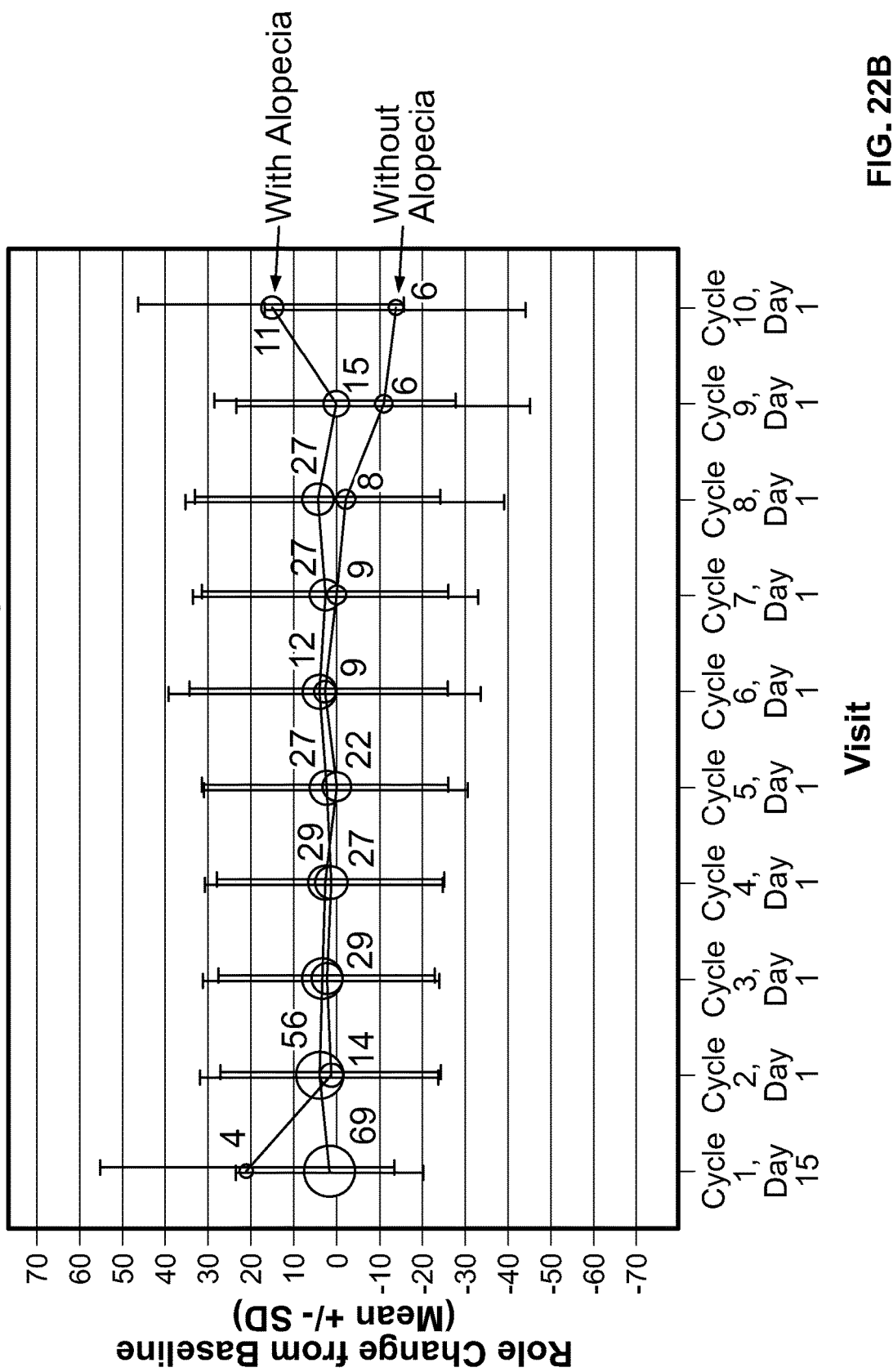
FIG. 22B depicts a mean change from baseline for role function patient reported outcome of the EORTC-QLQ-C30 in patients receiving ripretinib, with and without alopecia, in the study described in Example 2.
Figure 22C:
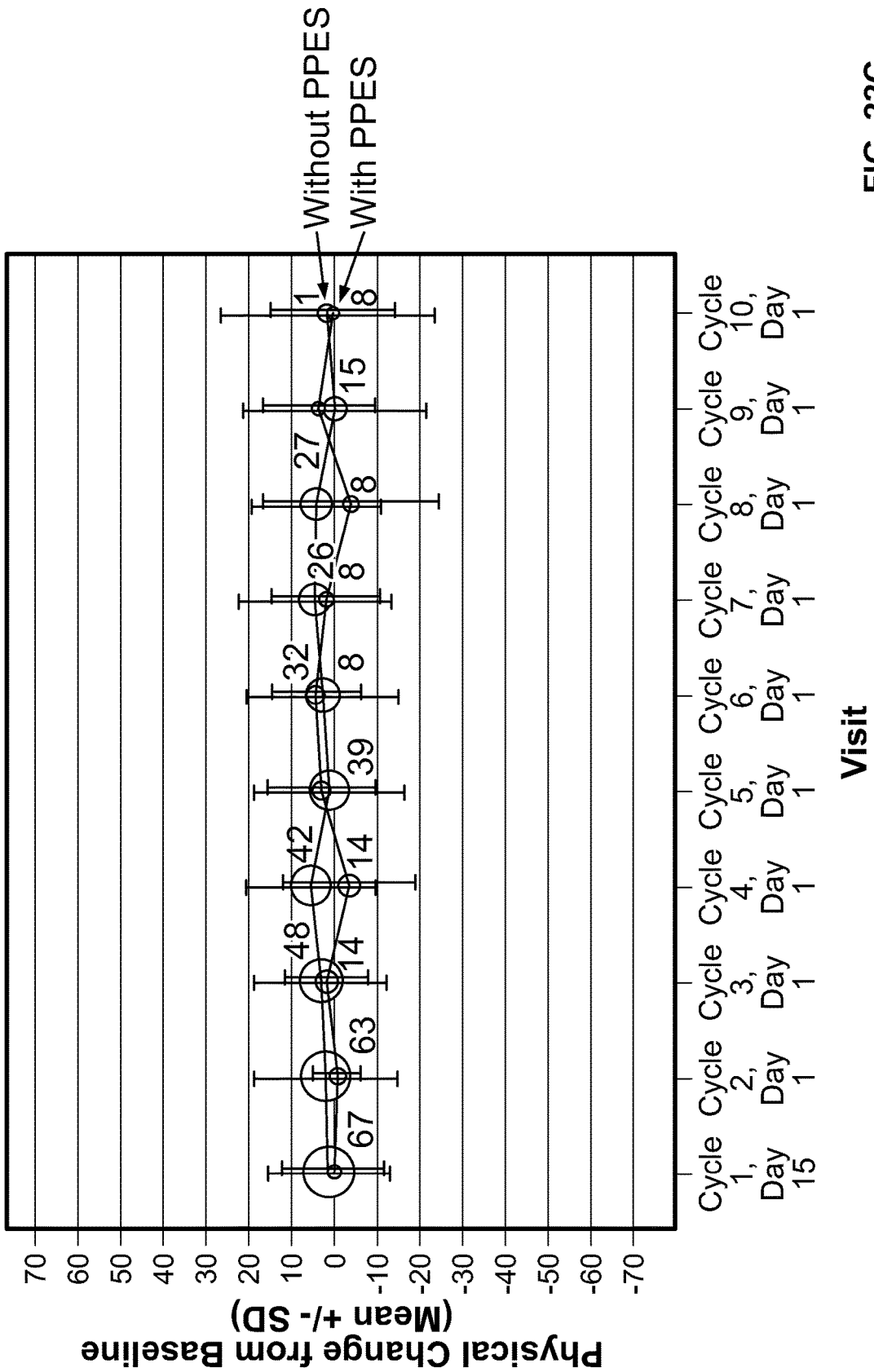
FIG. 22C depicts a mean change from baseline for physical function patient reported outcome of the EORTC-QLQ-C30 in patients receiving ripretinib, with and without palmar-plantar erythrodysesthesia syndrome (PPES), in the study described in Example 2.
Figure 22D:
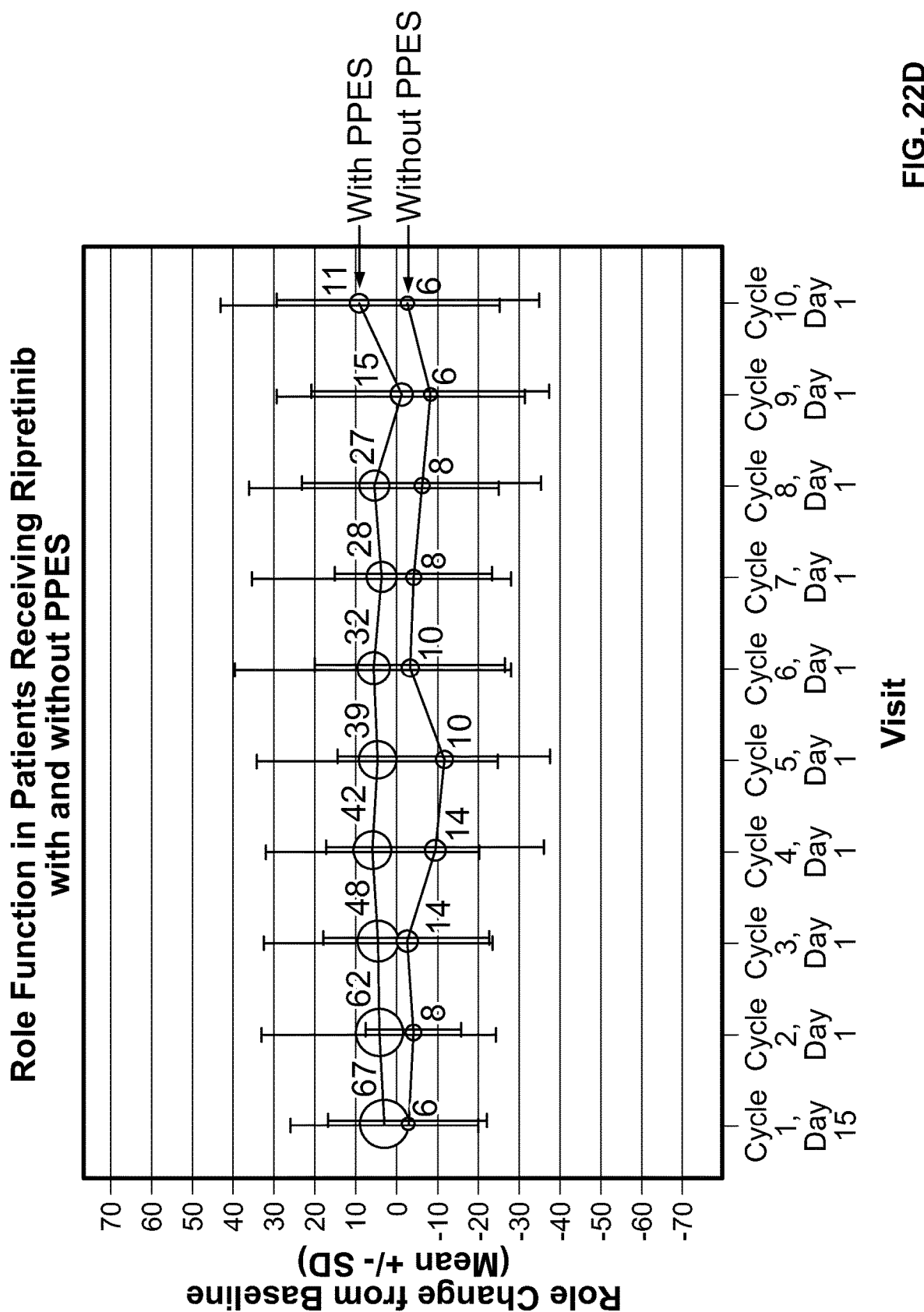
FIG. 22D depicts a mean change from baseline for role function patient reported outcome of the EORTC-QLQ-C30 in patients receiving ripretinib, with and without palmar-plantar erythrodysesthesia syndrome (PPES), in the study described in Example 2.
Figure 23A:
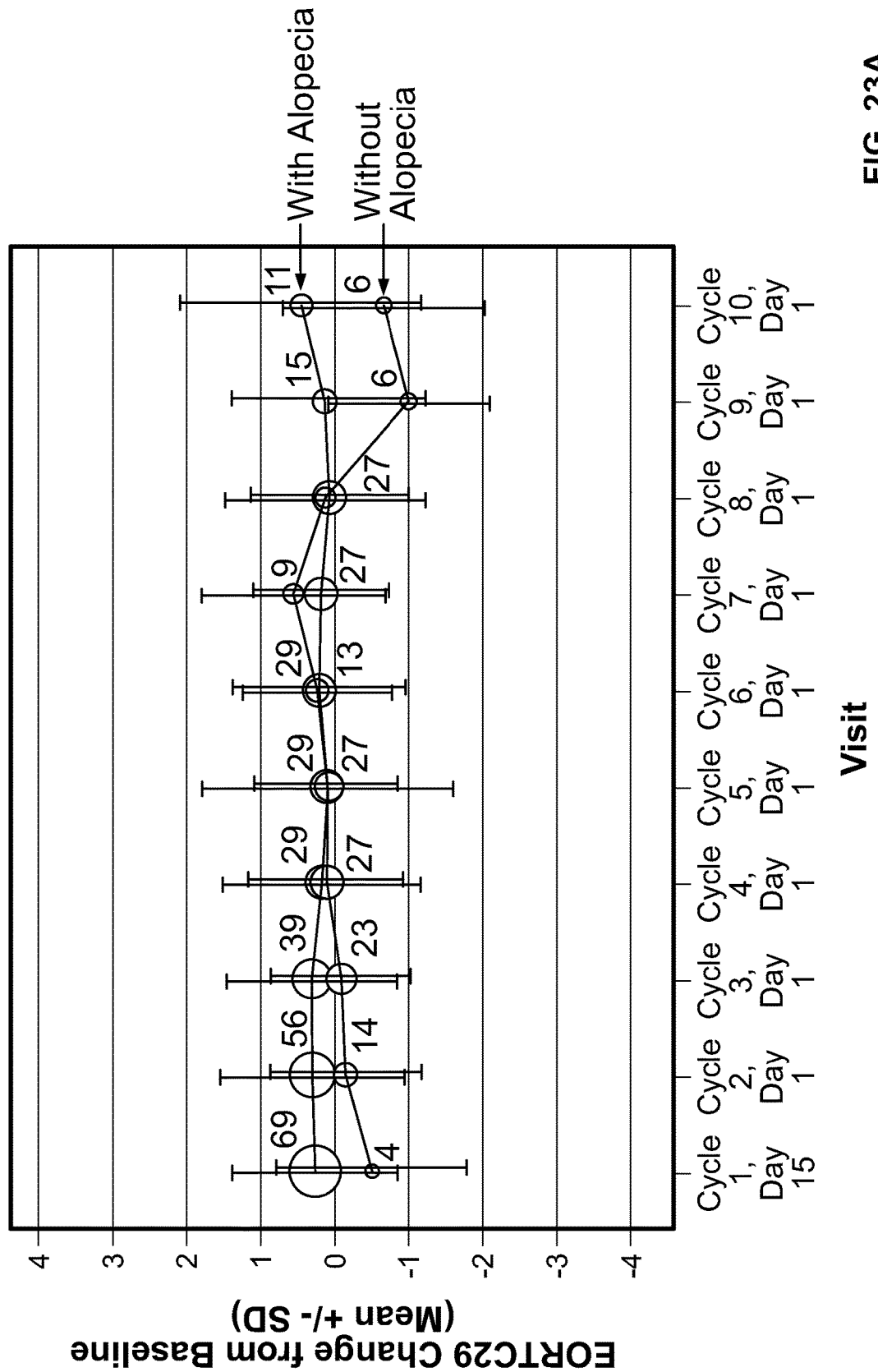
FIG. 23A depicts a mean change from baseline for overall health patient reported outcome of the EORTC-QLQ-C30 in patients receiving ripretinib, with and without alopecia, in the study described in Example 2.
Figure 23B:
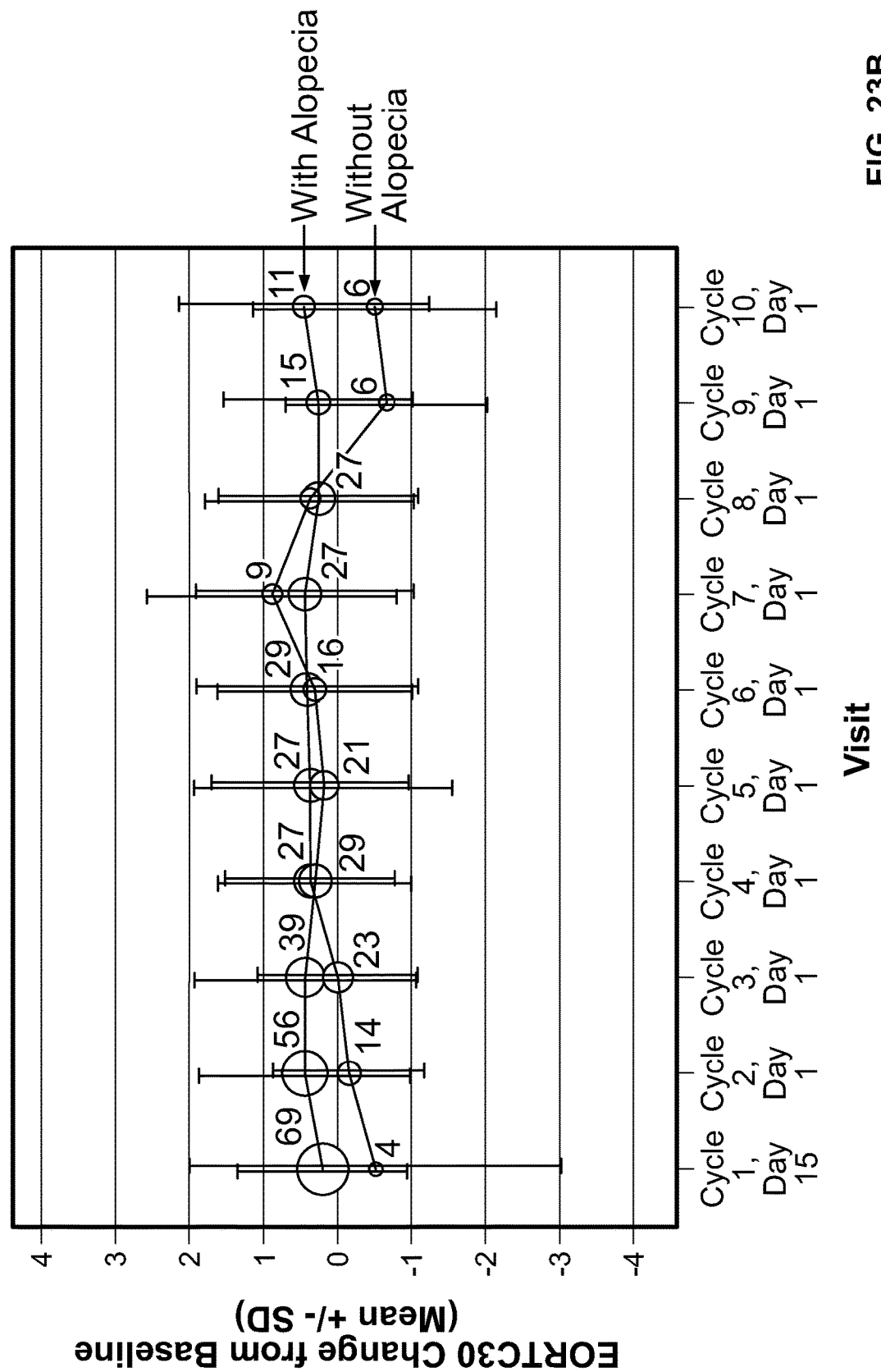
FIG. 23B depicts a mean change from baseline for overall quality of life patient reported outcome of the EORTC-QLQ-C30 in patients receiving ripretinib, with and without alopecia, in the study described in Example 2.
Figure 23C:
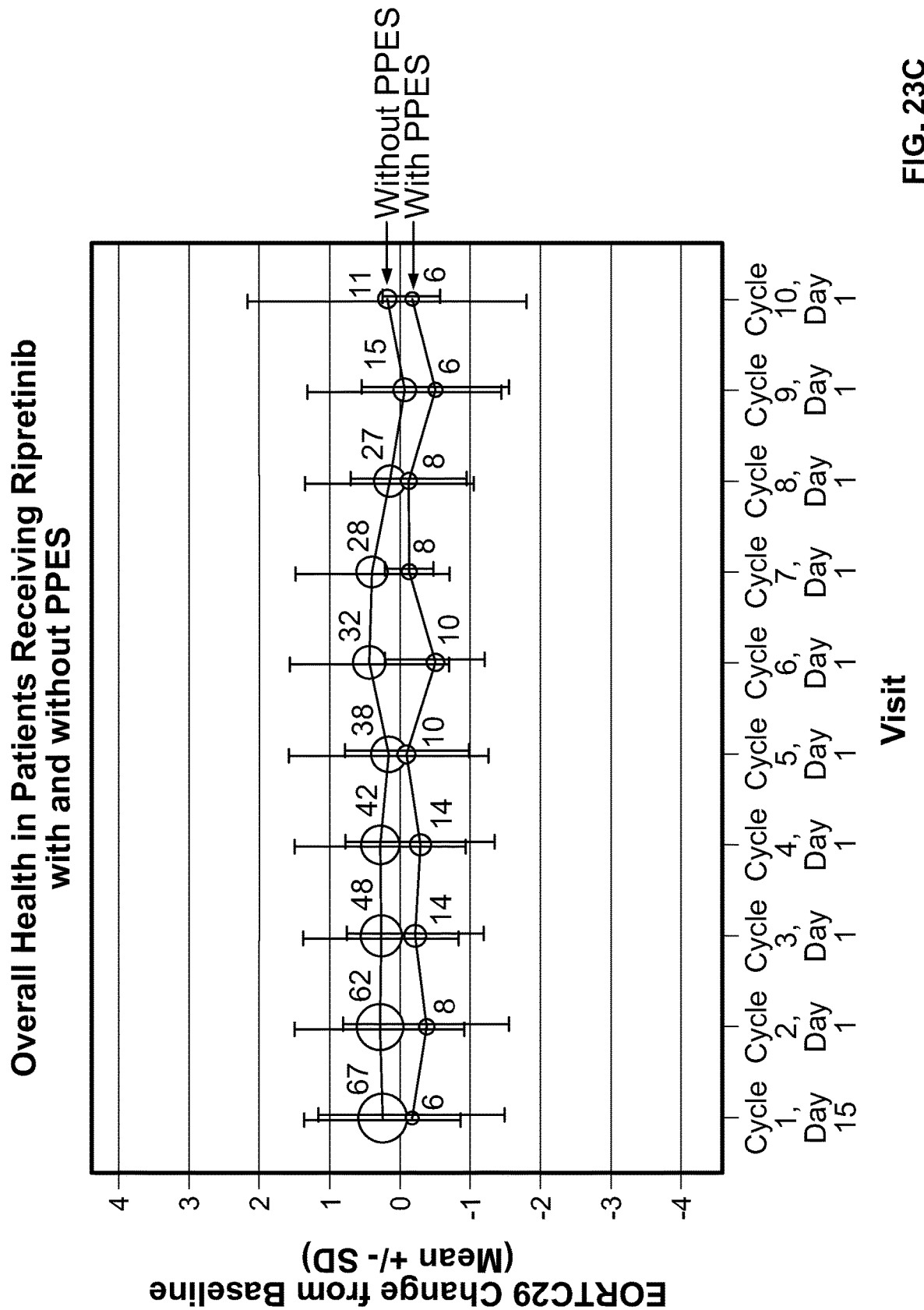
FIG. 23C depicts a mean change from baseline for overall health patient reported outcome of the EORTC-QLQ-C30 in patients receiving ripretinib, with and without palmar-plantar erythrodysesthesia syndrome (PPES), in the study described in Example 2.
Figure 23D:
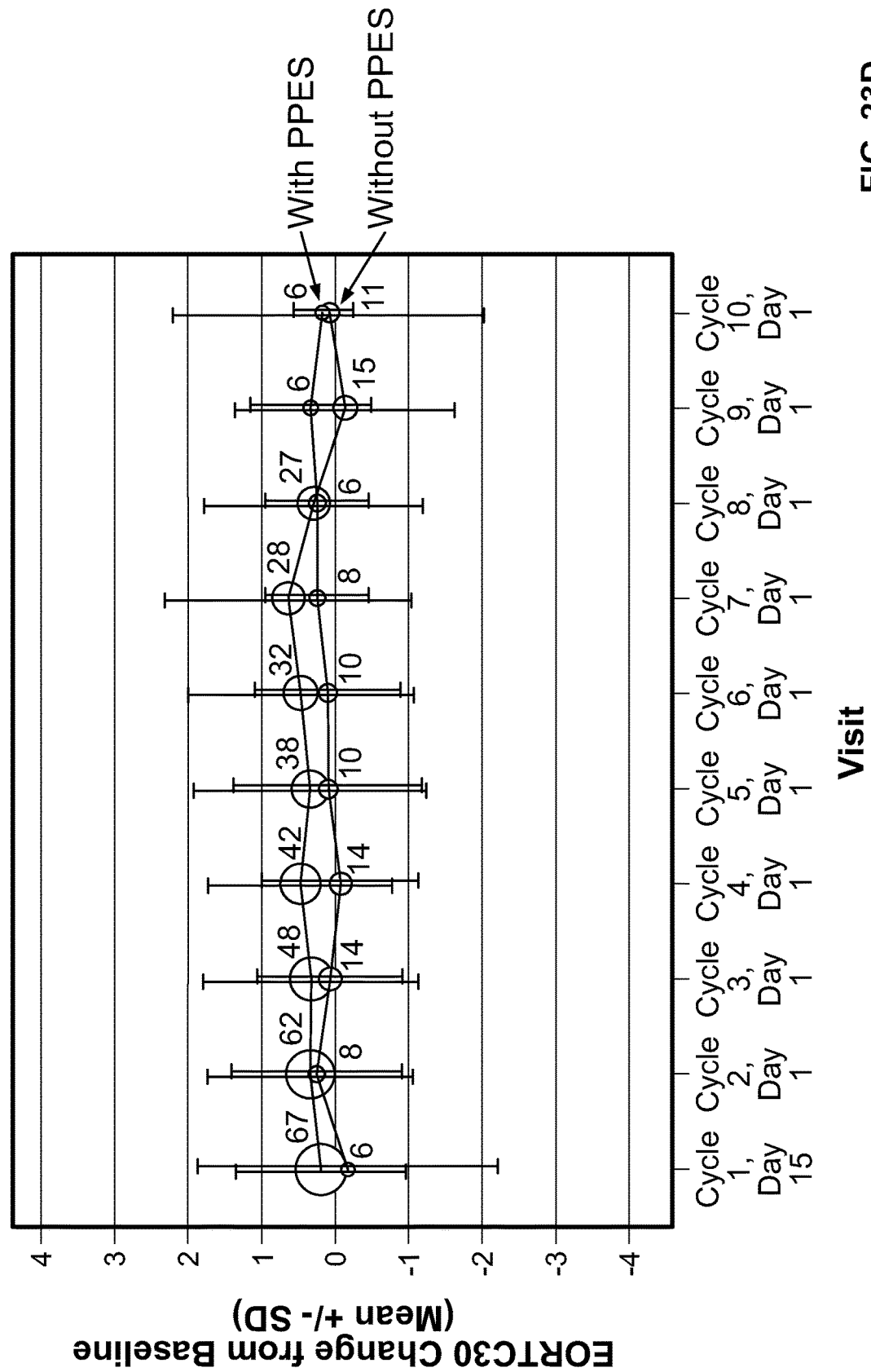
FIG. 23D depicts a mean change from baseline for overall quality of life patient reported outcome of the EORTC-QLQ-C30 in patients receiving ripretinib, with and without palmar-plantar erythrodysesthesia syndrome (PPES), in the study described in Example 2.
Figure 24A:
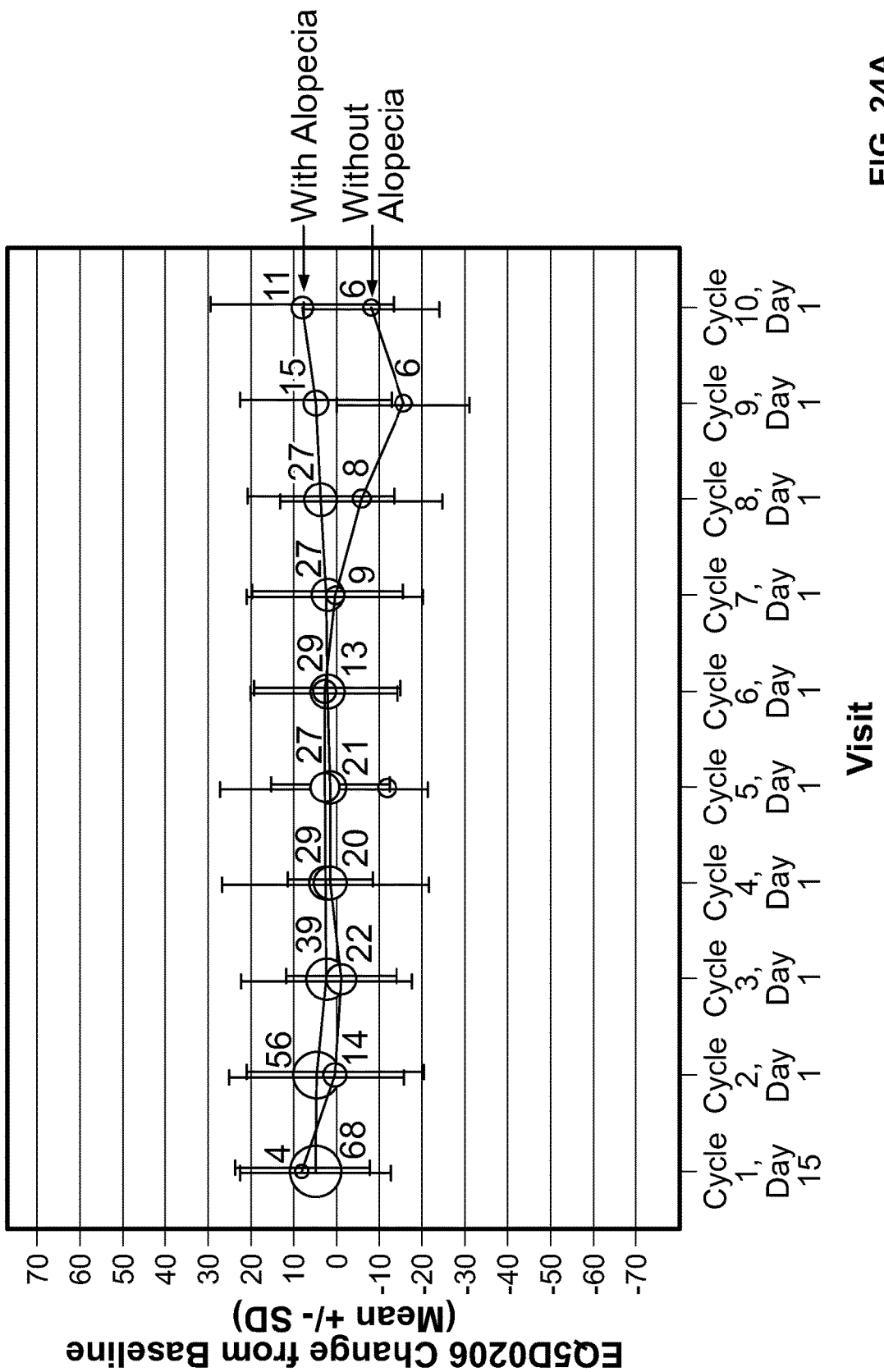
FIG. 24A depicts a mean change from baseline for state of health (VAS) patient reported outcome of the EORTC-QLQ-C30 in patients receiving ripretinib, with and without alopecia, in the study described in Example 2.
Figure 24B:
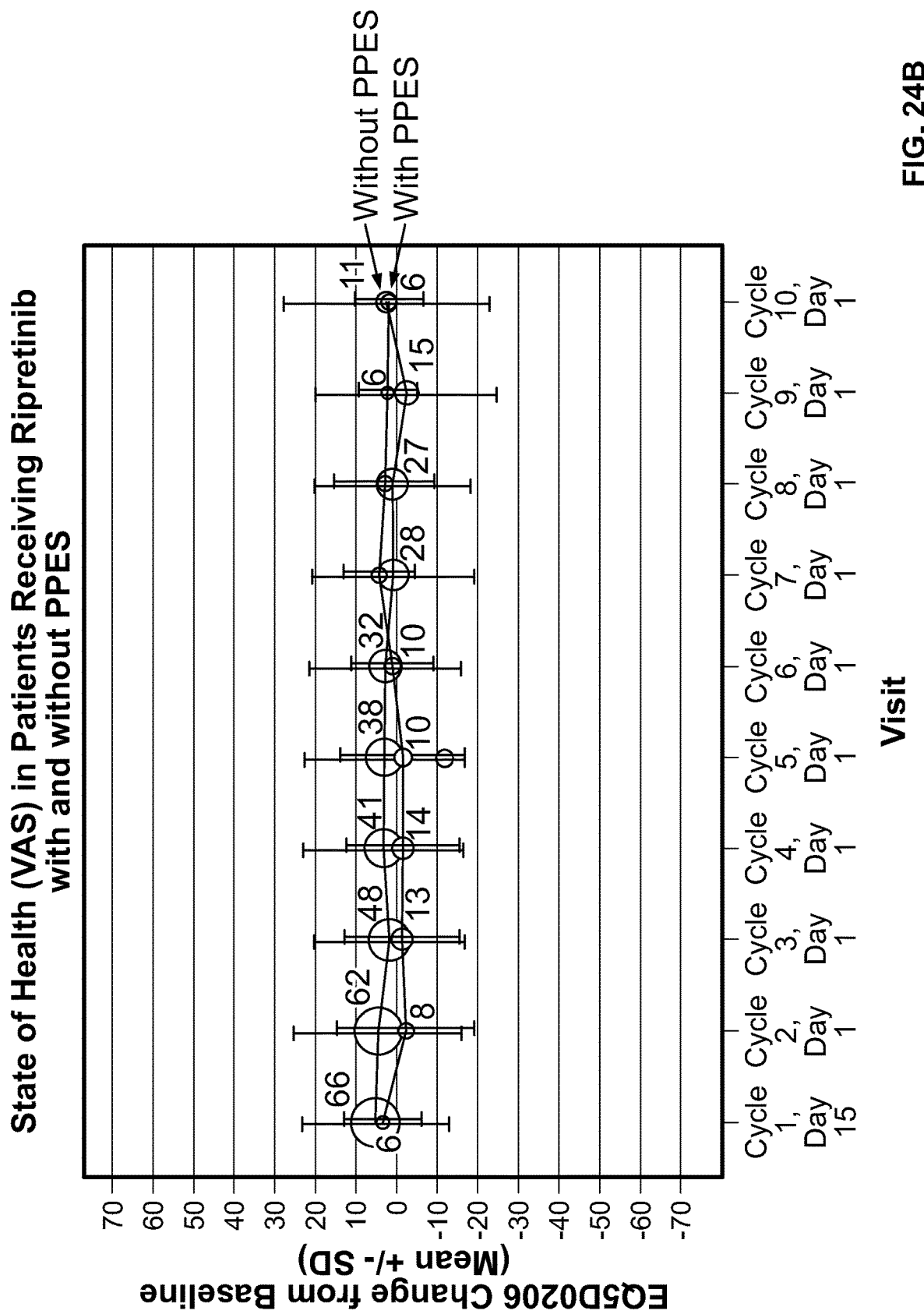
FIG. 24B depicts a mean change from baseline for state of health (VAS) patient reported outcome of the EORTC-QLQ-C30 in patients receiving ripretinib, with and without palmar-plantar erythrodysesthesia syndrome (PPES), in the study described in Example 2.

In the ripretinib arm, the most common treatment-emergent adverse event (TEAE) was alopecia (51.8%) and the most common grade 3/4 TEAE was anemia (9.4%). The highest severity classification for alopecia is grade 2; therefore, no patients in either arm had grade 3/4 alopecia. Alopecia was slightly more common in femalesvs males in the ripretinib arm (56.8% vs 43.2%). In the ripretinib arm, 21.2% of patients reported PPES; no patients had grade 3 PPES (grade 3 is the highest severity classification for PPES). There were no serious adverse events of alopecia or PPES reported. Within the ripretinib arm, 7.1%, 23.5%, and 5.9% of patients experienced a TEAE leading to dose reduction, dose interruption, or death, respectively, compared with 2.3%, 20.9%, and 23.3% in the placebo arm. In patients receiving ripretinib, the median worst grade of alopecia occurred very shortly after the median first appearance (FIG. 21). The median first appearance and worst grade of PPES occurred simultaneously in patients receiving ripretinib (FIG. 21).

Table 7 shows a GEE analysis summary of the association between alopecia and PPES with the 5 PRO measures in patients taking ripretinib. In a repeated measures analysis, there was a trend toward an improvement of the 5 PROs among patients with alopecia (Table 7). The presence of alopecia was associated with better self-reported overall quality of life (Table 7). This was statistically significant at P<0.01, but did not exceed the threshold for meaningful change. There was no association between PPES and the 5 PRO measures (Table 7).

TABLE 7

GEE analysis summary of the association between alopecia and PPES with the 5 PRO measures in patients taking ripretinib.

|  | Mean Estimate | Mean Confidence Limit | P-value from ChiSq |
|---|---|---|---|
| Alopecia EORTC-QLQ-C30 |  |  |  |
| Overall health | 0.17 | (−0.10, 0.44) | 0.2222 |
| Overall quality of life | 0.35 | (0.03, 0.67) | 0.0313 |
| Physical function | 3.17 | (−0.29, 6.64) | 0.0729 |
| Role function | 4.50 | (−2.87, 11.87) | 0.2310 |
| EQ-5D-5L |  |  |  |
| VAS | 3.01 | (−0.64, 6.67) | 0.1062 |
| PPES EORTC-QLQ-C30 |  |  |  |
| Overall health | 0.06 | (−0.29, 0.41) | 0.7457 |
| Overall quality of life | 0.12 | (−0.26, 0.50) | 0.5368 |
| Physical function | 3.03 | (−0.92, 6.99) | 0.1325 |
| Role function | 2.83 | (−5.52, 11.17) | 0.5070 |
| EQ-5D-5L |  |  |  |
| VAS | 1.65 | (−2.11, 5.41) | 0.3903 |

Longitudinal graphs out to Cycle 10, Day 1 demonstrate similar trends in mean change from baseline for the 5 PROs for patients receiving ripretinib that developed alopecia or PPES and those that did not (FIGS. 22A, 22B, 22C, 22D, 23A, 23B, 23C, 23D, 24A, and 24B).

TABLE 8

Comparison of double blind and open label data cut time periods.

|  | Ripretinib (N = 85) Double-blind cut | Ripretinib (N = 85) Open-label cut |
|---|---|---|
| Progression-Free Survival by BICR |  |  |
| Number of events (%) | 51 (60) | 64 (75) |
| Progressive disease | 46 (54) | 58 (68) |
| Deaths | 5 (6) | 6 (7) |
| Median PFS (months) (95% CI) | 6.3 (4.6, 6.9) | 6.3 (4.6, 8.1) |
| Hazard ratio (95% CI) | 0.15 (0.09, 0.25) | 0.16 (0.10, 0.27) |
| p-value | <0.0001 | <0.0001* |
| Overall Response Rate by BICR |  |  |
| Overall Response Rate (%) | 9 | 12 |
| (95% CI) | (4.2, 18) | (5.8, 20.6) |
| p-value | 0.0504 | 0.0156* |
| Overall Survival |  |  |
| Number of deaths (%) | 26 (31) | 38 (45) |
| Median OS (months) (95% CI) | 15 (12, 15) | Not Reached (13, NE) |
| Hazard ratio (95% CI)/p-value | 0.36 (0.21, 0.62)/ 0.0004* | 0.43 (0.26, 0.69)/ 0.0014* |
| Exposure |  |  |
| Mean in the double blind period (months) | 5.6 | 7.6 |

Example 7

Studies of Ripretinib and Compound A with Strong CYP3A Inhibitors

Coadministration of 150 mg QD ripretinib with a strong CYP3A inhibitor increased the exposure of ripretinib and its active metabolite (Compound A), which may increase the risk of adverse reactions. Coadministration of ripretinib with itraconazole (a strong CYP3A inhibitor and also a P-gp inhibitor) increased ripretinib $C_{max}$ by 36% and $AUC_{0-inf}$ by 99% and also increased Compound A $AUC_{0-inf}$ by 99% with no change in its $C_{max}$.

Example 8

Studies of Ripretinib with a Proton-Pump Inhibitor

The effect of a proton-pump inhibitor on the exposure of ripretinib was evaluated. No clinically significant differences in the plasma exposure to ripretinib and Compound A were observed when ripretinib was coadministered with pantoprazole, a proton-pump inhibitor. Although ripretinib has pH-dependent solubility, concomitant administration of 40 mg QD pantoprazole with 150 mg QD ripretinib did not affect ripretinib exposure.

Example 9

Studies of Food Effect on Ripretinib and Compound A Exposure

The effect of a high-fat breakfast on ripretinib and Compound A exposure was evaluated. A high fat meal consisted of approximately 150, 250, and 500-600 calories from protein, carbohydrate, and fat, respectively. Following administration of ripretinib with a high-fat meal at a 150 mg dose, ripretinib $AUC_{0-24\,h}$ and $C_{max}$ were higher by 30% and 22%, respectively. For the metabolite Compound A, $AUC_{0-24\,h}$ and $C_{max}$ were higher by 47% and 66%, respectively. The food effect is not considered to be clinically significant based on exposure-response analysis. Therefore, ripretinib may be taken with or without food at approximately same time each day.

EQUIVALENTS

Those skilled in the art will recognize, or be able to ascertain, using no more than routine experimentation,

The invention claimed is:

1. A method of treating a patient suffering from an advanced gastrointestinal stromal tumor, and where the patient is being treated concurrently with a CYP3A4 inhibitor, comprising orally administering to the patient a 150 mg daily dose of ripretinib, wherein the administration of the CYP3A4 inhibitor and the ripretinib to the patient increases ripretinib area under the plasma concentration curve ($AUC_{0\text{-}inf}$) by 80% or more in the patient as compared to administration of ripretinib without concurrent treatment of the CYP3A4 inhibitor, and therefore the patient is at higher risk of an adverse event; and monitoring the patient for the adverse event due to the ripretinib and CY3A4 inhibitor administration.

2. The method of claim 1, wherein if the patient suffers from an adverse event upon administration of the ripretinib and the CY3A4 inhibitor, the method further comprises administering to the patient a reduced dose of 100 mg daily of the ripretinib.

3. The method of claim 1, wherein if the patient suffers from a Grade 3 adverse event selected from the group consisting of arthralgia, myalgia and palmer-plantar erythrodysesthia syndrome after administration of the ripretinib and the CYP3A4 inhibitor, the method further comprises: a) withholding administration of the ripretinib for at least 7 days or until the patient has less than or equal to grade 1 of the adverse event, then b) administering to the patient 100 mg daily of the ripretinib for at least 28 days.

4. The method of claim 1, wherein if the patient suffers from a Grade 3 adverse event after the administration of the ripretinib and the CYP3A4 inhibitor, the method further comprises: a) withholding administration of the ripretinib for at least 7 days or until the patient has less than or equal to grade 1 of the adverse event, then b) administering to the patient 100 mg daily of the ripretinib for at least 28 days.

5. The method of claim 1, wherein the adverse event is one or more of: nausea, vomiting, anemia or abdominal pain.

6. The method of claim 1, wherein the CYP3A4 inhibitor is selected from the group consisting of itraconazole, ketoconazole, clarithromycin, and indinavir.

* * * * *

UNITED STATES PATENT AND TRADEMARK OFFICE
CERTIFICATE OF CORRECTION

PATENT NO. : 11,426,390 B2
APPLICATION NO. : 17/583977
DATED : August 30, 2022
INVENTOR(S) : Rodrigo Ruiz Soto et al.

It is certified that error appears in the above-identified patent and that said Letters Patent is hereby corrected as shown below:

In the Claims

In Claim 3, at Column 38, Lines 3-4, replace "erythrodysesthia" with --erythrodysesthesia--.

Signed and Sealed this
Eleventh Day of October, 2022

Katherine Kelly Vidal
*Director of the United States Patent and Trademark Office*